United States Patent
Heywood et al.

(10) Patent No.: US 10,829,565 B2
(45) Date of Patent: Nov. 10, 2020

(54) METHOD FOR INCREASING THE PERCENTAGE OF MONOMERIC ANTIBODY FAB-DSFV MULTIMERIC SPECIES

(71) Applicant: UCB BIOPHARMA SPRL, Brussels (BE)

(72) Inventors: Sam Philip Heywood, Slough (GB); Gavin Barry Wild, Slough (GB); Christopher John Le Page, Slough (GB); Razwan Hanif, Slough (GB)

(73) Assignee: UCB BIOPHARMA SPRL, Brussels (BE)

( * ) Notice: Subject to any disclaimer, the term of this patent is extended or adjusted under 35 U.S.C. 154(b) by 0 days.

(21) Appl. No.: 15/568,018

(22) PCT Filed: Apr. 22, 2016

(86) PCT No.: PCT/EP2016/059050
§ 371 (c)(1),
(2) Date: Oct. 20, 2017

(87) PCT Pub. No.: WO2016/170137
PCT Pub. Date: Oct. 27, 2016

(65) Prior Publication Data
US 2018/0142039 A1 May 24, 2018

(30) Foreign Application Priority Data

Apr. 22, 2015 (GB) .................................. 1506869.5

(51) Int. Cl.
| | | |
|---|---|---|
| *C07K 16/28* | (2006.01) | |
| *C07K 16/46* | (2006.01) | |
| *C07K 16/00* | (2006.01) | |
| *C07K 1/22* | (2006.01) | |
| *C07K 16/18* | (2006.01) | |

(52) U.S. Cl.
CPC ............ *C07K 16/468* (2013.01); *C07K 16/18* (2013.01); *C07K 16/2878* (2013.01); *C07K 2317/14* (2013.01); *C07K 2317/31* (2013.01); *C07K 2317/52* (2013.01); *C07K 2317/55* (2013.01); *C07K 2317/565* (2013.01); *C07K 2317/624* (2013.01); *C07K 2317/66* (2013.01)

(58) Field of Classification Search
CPC .. C07K 16/468; C07K 16/18; C07K 16/2878; C07K 2317/565; C07K 2317/55; C07K 2317/14; C07K 2317/31; C07K 2317/624; C07K 2317/66
See application file for complete search history.

(56) References Cited

U.S. PATENT DOCUMENTS

| | | |
|---|---|---|
| 4,741,900 A | 5/1988 | Alvarez et al. |
| 4,816,397 A | 3/1989 | Boss et al. |
| 5,219,996 A | 6/1993 | Bodmer et al. |
| 5,223,409 A | 6/1993 | Ladner et al. |
| 5,403,484 A | 4/1995 | Ladner et al. |
| 5,427,908 A | 6/1995 | Dower et al. |
| 5,516,637 A | 5/1996 | Huang et al. |
| 5,545,806 A | 8/1996 | Lonberg et al. |
| 5,569,825 A | 10/1996 | Lonberg et al. |
| 5,571,698 A | 11/1996 | Ladner et al. |
| 5,580,717 A | 12/1996 | Dower et al. |
| 5,585,089 A | 12/1996 | Queen et al. |
| 5,625,126 A | 4/1997 | Lonberg et al. |
| 5,633,425 A | 5/1997 | Lonberg et al. |
| 5,658,727 A | 8/1997 | Barbas et al. |
| 5,661,016 A | 8/1997 | Lonberg et al. |
| 5,667,425 A | 9/1997 | Pineau et al. |
| 5,698,426 A | 12/1997 | Huse |
| 5,733,743 A | 3/1998 | Johnson et al. |
| 5,750,753 A | 5/1998 | Kimae et al. |
| 5,770,429 A | 6/1998 | Lonberg et al. |
| 5,780,225 A | 7/1998 | Wigler et al. |
| 5,821,047 A | 10/1998 | Garrard et al. |
| 5,969,108 A | 10/1999 | McCafferty et al. |
| 6,331,415 B1 | 12/2001 | Cabilly et al. |

(Continued)

FOREIGN PATENT DOCUMENTS

| | | |
|---|---|---|
| EP | 0392745 | 11/1994 |
| EP | 0438474 | 5/1996 |

(Continued)

OTHER PUBLICATIONS

Stancovski et al., PNAS 88: 8691-8695 (Year: 1991).*
Golay et al., Archives of Biochemistry and Biophysics 526: 146-153 (Year: 2012).*
Yu et al., Investigative Ophthalmology & Visual Science 49(2): 522-527 (Year: 2008).*

(Continued)

*Primary Examiner* — Phuong Huynh
(74) *Attorney, Agent, or Firm* — Saliwanchik, Lloyd & Eisenschenk

(57) ABSTRACT

The present invention provides method for increasing the percentage of monomer in a composition of recombinantly expressed antibody molecules characterised in that the antibody molecule comprises at least one Fv with specificity for an antigen of interest comprising one VH and one VL wherein said VH and VL are connected directly or indirectly via one or more linkers and are stabilised by a disulfide bond therebetween, said method comprises a) a thermal conversion step of holding the composition comprising the antibody molecule at a temperature in the range 30 to 60° C. for a period of at least 1 hour, wherein step a) is performed in the presence of a reducing agent or after treatment with a reducing agent.

22 Claims, 29 Drawing Sheets
Specification includes a Sequence Listing.

(56) References Cited

U.S. PATENT DOCUMENTS

| | | | |
|---|---|---|---|
| 2007/0191272 A1 | 8/2007 | Stemmer et al. | |
| 2011/0229933 A1* | 9/2011 | Krishnan | C07K 16/2863 435/69.6 |
| 2013/0022598 A1 | 1/2013 | Bigner et al. | |
| 2013/0039913 A1* | 2/2013 | Labrijn | C07K 16/1063 424/136.1 |
| 2013/0066054 A1* | 3/2013 | Humphreys | C07K 16/00 530/391.1 |
| 2018/0100007 A1 | 4/2018 | Heywood et al. | |
| 2018/0117153 A1 | 5/2018 | Heywood et al. | |

FOREIGN PATENT DOCUMENTS

| | | | |
|---|---|---|---|
| EP | 0463151 | 6/1996 | |
| EP | 0546073 | 9/1997 | |
| WO | WO 86/01533 | 3/1986 | |
| WO | WO 89/00195 | 1/1989 | |
| WO | WO 89/01476 | 2/1989 | |
| WO | WO 90/02809 | 3/1990 | |
| WO | WO 91/09967 | 7/1991 | |
| WO | WO 91/10737 | 7/1991 | |
| WO | WO 92/01047 | 1/1992 | |
| WO | WO 92/02551 | 2/1992 | |
| WO | WO 92/18619 | 10/1992 | |
| WO | WO 92/22583 | 12/1992 | |
| WO | WO 93/06231 | 4/1993 | |
| WO | WO 93/11236 | 6/1993 | |
| WO | WO 95/15982 | 6/1995 | |
| WO | WO 95/20401 | 8/1995 | |
| WO | WO 98/20734 | 5/1998 | |
| WO | WO 98/25971 | 6/1998 | |
| WO | WO 03/031581 | 4/2003 | |
| WO | WO 2004/051268 | 6/2004 | |
| WO | WO 2004/106377 | 12/2004 | |
| WO | WO 2005/003169 | 1/2005 | |
| WO | WO 2005/003171 | 1/2005 | |
| WO | WO-2005003170 A2 * | 1/2005 | C07K 16/244 |
| WO | WO 2005/117984 | 12/2005 | |
| WO | WO 2006/047340 | 5/2006 | |
| WO | WO 2008/038024 | 4/2008 | |
| WO | WO 2009/007124 | 1/2009 | |
| WO | WO 2009/040562 | 4/2009 | |
| WO | WO 2010/019493 | 2/2010 | |
| WO | WO 2010/035012 | 4/2010 | |
| WO | WO 2011/030107 | 3/2011 | |
| WO | WO 2011/036460 | 3/2011 | |
| WO | WO 2011/061492 | 5/2011 | |
| WO | WO 2011/086091 | 7/2011 | |
| WO | WO 2011/117648 | 9/2011 | |
| WO | WO 2011/117653 | 9/2011 | |
| WO | WO 2012/140214 | 10/2012 | |
| WO | WO 2013/055958 | 4/2013 | |
| WO | WO 2013/068563 | 5/2013 | |
| WO | WO 2013/068571 | 5/2013 | |
| WO | WO 2013/132268 | 9/2013 | |
| WO | WO 2014/019727 | 2/2014 | |
| WO | WO 2015/197772 | 12/2015 | |
| WO | WO 2016/169992 | 10/2016 | |
| WO | WO 2016/170138 | 10/2016 | |
| WO | WO 2017/029620 | 2/2017 | |

OTHER PUBLICATIONS

Reed et al., Biotechnol. Prog. vol. 29, No. 3: 745-753 (Year: 2013).*
Written Opinion in International Application No. PCT/EP2016/059050, dated Sep. 15, 2016, pp. 1-5.
Ditzel, H. et al. "Preparation of antigen-binding monomeric and half-monomeric fragments from human monoclonal IgM antibodies against colorectal cancer-associated antigens" *Hum. Antibod. Hybridomas*, Apr. 1993, pp. 86-93, vol. 4.
Olichon, A. et al. "Heating as a rapid purification method for recovering correctly-folded thermotolerant VH and VHH domains" *BMC Biotechnology*, Jan. 26, 2007, pp. 1-8, vol. 7, No. 7.
International Search Report for International Application No. PCT/EP2012/072335, dated Apr. 22, 2013, pp. 1-5.
Rousseaux-Prevost, R. et al. "Differential Reduction of the Inter-Chain Disulfide Bonds of Rat Immunoglobulin E: Relation to Biological Activity" *Molecular Immunology*, 1984, pp. 233-241, vol. 21, No. 3.
Search Report for Application No. GB1506869.5, dated Jan. 18, 2016, pp. 1-4.
Williams, A. J. et al. "Improved Assembly of Bispecific Antibodies from Knob and Hole Half-Antibodies" *Biotechnol Prog.*, 2015, pp. 1315-1322, vol. 31, No. 5.
Adair, J. R. et al. "Therapeutic Antibodies" *Drug Design Reviews*, 2005, pp. 1-11.
Ames, R. S. et al. "Conversion of murine Fabs isolated from a combinatorial phage display library to full length immunoglobulins" *Journal of Immunological Methods*, 1995, pp. 177-186, vol. 184.
Babcook, J. S. et al. "A novel strategy for generating monoclonal antibodies from single, isolated lymphocytes producing antibodies of defined specificities" *Proc. Natl. Acad. Sci. USA*, Jul. 1996, pp. 7843-7848, vol. 93.
Bird, R. E. et al. "Single-Chain Antigen-Binding Proteins" *Science*, Oct. 21, 1988, pp. 423-426, vol. 242.
Brinkmann, U. et al. "A recombinant immunotoxin containing a disulfide-stabilized Fv fragment" *Proc. Natl. Acad. Sci. USA*, Aug. 1993, pp. 7538-7542, vol. 90.
Brinkmann, U. et al. "Phage display of disulfide-stabilized Fv fragments" *Journal of Immunological Methods*, 1995, pp. 41-50, vol. 182.
Burton, D. R. et al. "Human Antibodies from Combinatorial Libraries" *Advances in Immunology*, 1994, pp. 191-280, vol. 57.
Chapman, A. P. "PEGylated antibodies and antibody fragments for improved therapy: a review" *Advanced Drug Delivery Reviews*, 2002, pp. 531-545, vol. 54.
Chothia, C. et al. "Canonical Structures for the Hypervariable Regions of Immunoglobulins" *J. Mol. Biol.*, 1987, pp. 901-917, vol. 196.
Dubowchik, G. M. et al. "Receptor-mediated and enzyme-dependent targeting of cytotoxic anticancer drugs" *Pharmacology & Therapeutics*, 1999, pp. 67-123, vol. 83.
Glockshuber, R. et al. "A Comparison of Strategies to Stabilize Immunoglobulin Fv-Fragments" *Biochemistry*, 1990, pp. 1362-1367, vol. 29, No. 6.
Harris, R. J. "Processing of C-terminal lysine and arginine residues of proteins isolated from mammalian cell culture" *Journal of Chromatography A*, 1995, pp. 129-134, vol. 705.
Hellstrom, K. E. et al. "Antibodies for Drug Delivery" *Controlled Drug Delivery*, 2nd Ed., 1987, pp. 623-653.
Jung, S.-H. et al. "Design of Interchain Disulfide Bonds in the Framework Region of the Fv Fragment of the Monoclonal Antibody B3" *Proteins: Structure, Function, and Genetics*, 1994, pp. 35-47, vol. 19.
Kettleborough, C. A. et al. "Isolation of tumor cell-specific single-chain Fv from immunized mice using phage-antibody libraries and the re-construction of whole antibodies from these antibody fragments" *Eur. J. Immunol.*, 1994, pp. 952-958, vol. 24.
Kohler, G. et al. "Continuous cultures of fused cells secreting antibody of predefined specificity" *Nature*, Aug. 7, 1975, pp. 495-497, vol. 256.
Kozbor, D. et al. "The production of monoclonal antibodies from human lymphocytes" *Immunology Today*, 1983, pp. 72-79, vol. 4, No. 3.
Luo, D. et al. "Vl-Linker-Vh Orientation-Dependent Expression of Single Chain Fv Containing an Engineered Disulfide-Stabilized Bond in the Framework Regions" *J. Biochem.*, 1995, pp. 825-831, vol. 118.
Mountain, A. et al. "Engineering Antibodies for Therapy" *Biotechnology and Genetic Engineering Reviews*, 1992, pp. 1-143, vol. 10. No. 1.
Orlandi, R. et al. "Cloning immunoglobulin variable domains for expression by the polymerase chain reaction" *Proc. Natl. Acad. Sci. USA.*, May 1989, pp. 3833-3837, vol. 86.

(56) References Cited

OTHER PUBLICATIONS

Persic, L. et al. "An integrated vector system for the eukaryotic expression of antibodies or their fragments after selection from phage display libraries" *Gene*, 1997, pp. 9-18, vol. 187.

Rajagopal, V. et al. "A form of anti-Tac(Fv) which is both single-chain and disulfide stabilized: comparison with its single-chain and disulfide-stabilized homologs" *Protein Engineering*, 1997, pp. 1453-1459, vol. 10, No. 12.

Reiter, Y. et al. "Stabilization of the Fv Fragments in Recombinant Immunotoxins by Disulfide Bonds Engineered into Conserved Framework Regions" *Biochemistry*, 1994, pp. 5451-5459, vol. 33.

Reiter, Y. et al. "Improved Binding and Antitumor Activity of a Recombinant Anti-erbB2 Immunotoxin by Disulfide Stabilization of the Fv Fragment" *The Journal of Biological Chemistry*, Jul. 15, 1994, pp. 18327-18331, vol. 269, No. 28.

Riechmann, L. et al. "Reshaping human antibodies for therapy" *Nature*, Mar. 24, 1988, pp. 1-6, vol. 332.

Thorpe, P. E. et al. "The Preparation and Cytotoxic Properties of Antibody-Toxin Conjugates" *Immunological Rev.*, 1982, pp. 119-158, vol. 62.

Verma, R. et al. "Antibody engineering: Comparison of bacterial, yeast, insect and mammalian expression systems" *Journal of Immunological Methods*, 1998, pp. 165-181, vol. 216.

Ward, E. S. et al. "Binding activities of a repertoire of single immunoglobulin variable domains secreted from *Escherichia coli*" *Nature*, Oct. 12, 1989, pp. 544-546, vol. 341.

Wells, J. A. et al. "Cassette mutagenesis: an efficient method for generation of multiple mutations at defined sites" *Gene*, 1985, pp. 315-323, vol. 34.

Young, N. M. et al. "Thermal stabilization of a single-chain Fv antibody fragment by introduction of a disulphide bond" *FEBS Letters*, 1995, pp. 135-139, vol. 377.

Zhu, Z. et al. "Remodeling domain interfaces to enhance heterodimer formation" *Protein Science*, 1997, pp. 781-788, vol. 6.

\* cited by examiner

Figure 1

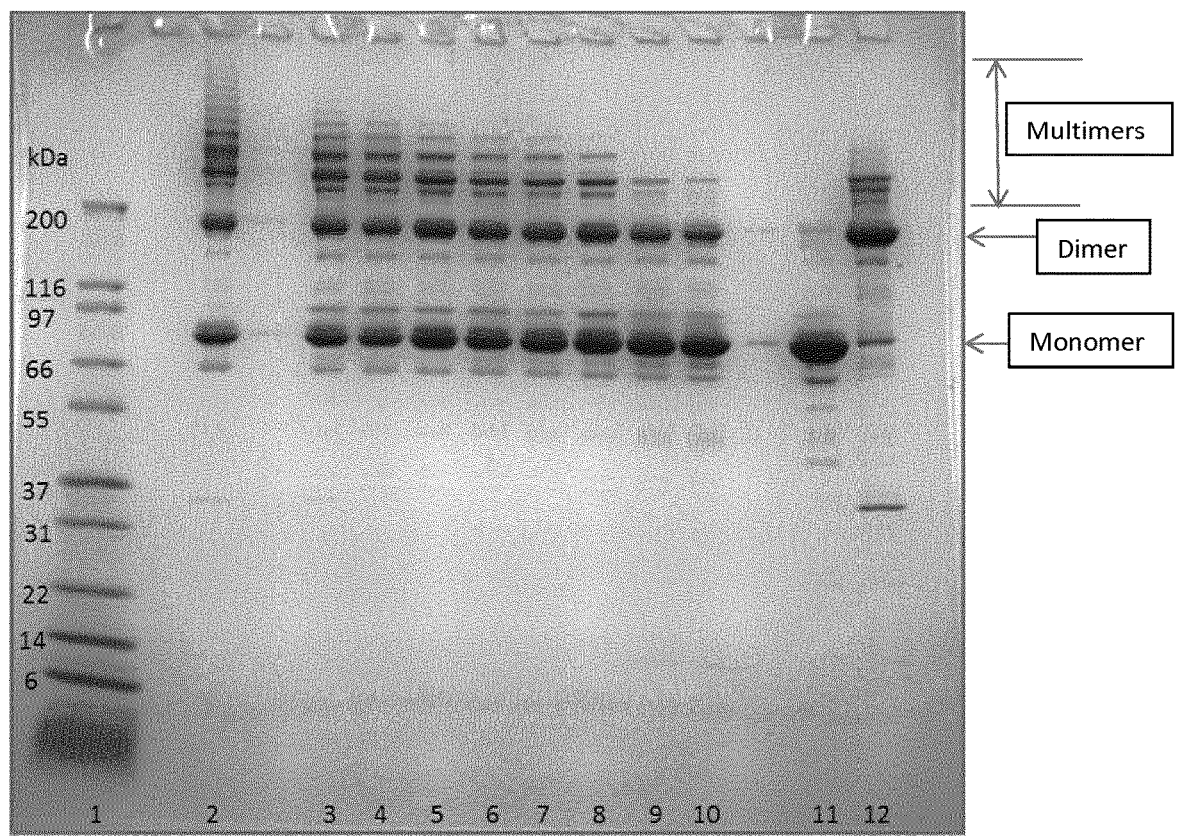

| Lane | Sample |
|---|---|
| 1 | Novex Mark 12 Molecular Weight Markers |
| 2 | A26Fab-645dsFv Post Protein-A Purification |
| 3 | A26Fab-645dsFv Conversion @ Time 00:30 |
| 4 | A26Fab-645dsFv Conversion @ Time 01:00 |
| 5 | A26Fab-645dsFv Conversion @ Time 02:00 |
| 6 | A26Fab-645dsFv Conversion @ Time 03:00 |
| 7 | A26Fab-645dsFv Conversion @ Time 04:00 |
| 8 | A26Fab-645dsFv Conversion @ Time 05:00 |
| 9 | A26Fab-645dsFv Conversion @ Time 20:20 |
| 10 | A26Fab-645dsFv Conversion @ Time 44:14 |
| 11 | A26Fab-645dsFv Monomer Reference Material |
| 12 | A26Fab-645dsFv Multimer Reference Material |

Figure 2

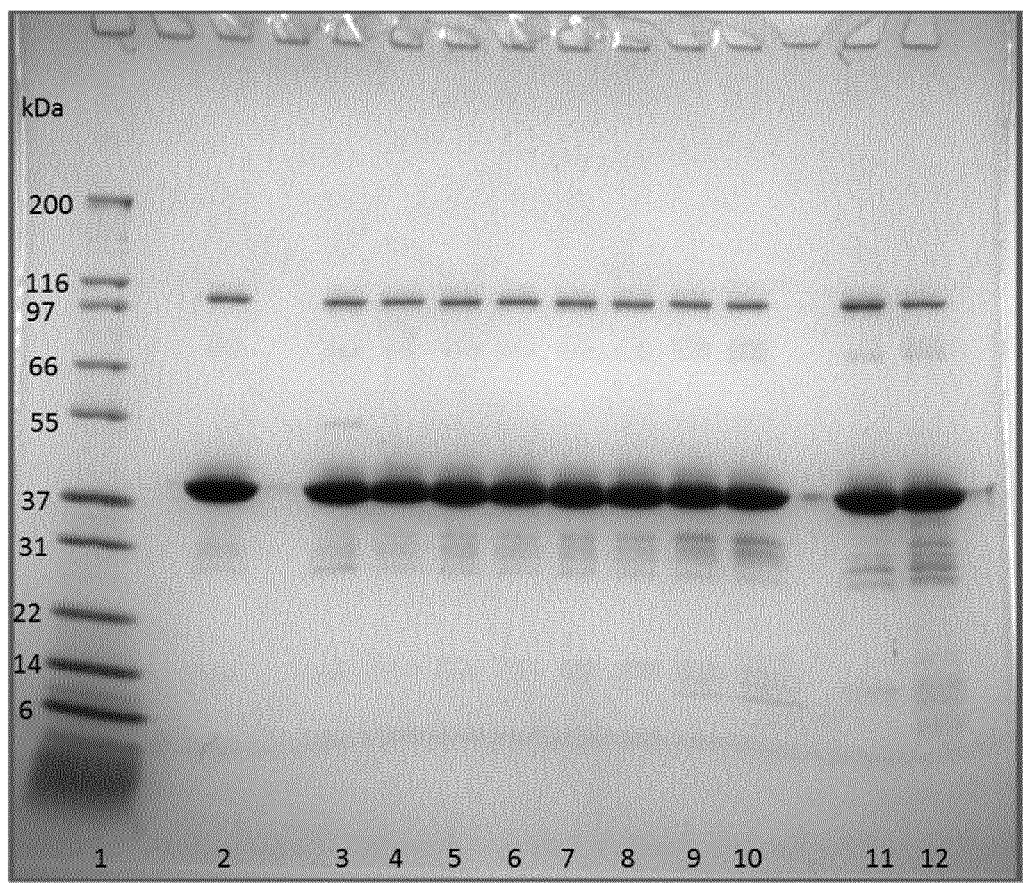

| Lane | Sample |
|---|---|
| 1 | Novex Mark 12 Molecular Weight Markers |
| 2 | A26Fab-645dsFv Post Protein-A Purification |
| 3 | A26Fab-645dsFv Conversion @ Time 00:30 |
| 4 | A26Fab-645dsFv Conversion @ Time 01:00 |
| 5 | A26Fab-645dsFv Conversion @ Time 02:00 |
| 6 | A26Fab-645dsFv Conversion @ Time 03:00 |
| 7 | A26Fab-645dsFv Conversion @ Time 04:00 |
| 8 | A26Fab-645dsFv Conversion @ Time 05:00 |
| 9 | A26Fab-645dsFv Conversion @ Time 20:20 |
| 10 | A26Fab-645dsFv Conversion @ Time 44:14 |
| 11 | A26Fab-645dsFv Monomer Reference Material |
| 12 | A26Fab-645dsFv Multimer Reference Material |

| Lane | Sample |
|---|---|
| 1 | Novex Mark 12 Molecular Weight Markers |
| 2 | A26Fab-645dsFv Clarified Cell Culture Supernatant |
| 3 | A26Fab-645dsFv MabSelect Elution @ pH 3.5 (No conversion) |
| 4 | A26Fab-645dsFv MabSelect Elution @ pH 3.5 (Supernatant conversion) |
| 5 | A26Fab-645dsFv Monomer Reference |
| 6 | A26FabFv-645Fv Multimer Reference |

| Lane | Sample |
|------|--------|
| 1 | Novex Mark 12 Molecular Weight Markers |
| 2 | A26Fab-645dsFv Clarified Cell Culture Supernatant |
| 3 | A26Fab-645dsFv MabSelect Elution @ pH 3.5 (No conversion) |
| 4 | A26Fab-645dsFv MabSelect Elution @ pH 3.5 (Supernatant conversion) |
| 5 | A26Fab-645dsFv Monomer Reference |
| 6 | A26Fab-645dsFv Multimer Reference |

Figure 19

(a) Light chain variable region of antibody A26 specific to OX40 (SEQ ID NO:7)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKR (b) Heavy chain variable region of antibody A26 specific to OX40 (SEQ ID NO:8)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS (c)
| | |
|---|---|
| CDRH1: | NYGIH (SEQ ID NO:1) |
| CDRH2: | SISPSGGLTYYRDSVKG (SEQ ID NO:2) |
| CDRH3: | GGEGIFDY (SEQ ID NO:3) |
| CDRL1: | RATQSIYNALA (SEQ ID NO:4) |
| CDRL2: | NANTLHT (SEQ ID NO:5) |
| CDRL3: | QQYYDYPLT (SEQ ID NO:6) |

(d) Light chain of anti-OX40 antibody Fab component (SEQ ID NO:9)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGEC (e) Heavy chain of anti-OX40 antibody Fab component (SEQ ID NO:10)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSC

Figure 20

(a) Heavy chain of anti-albumin Fv component (SEQ ID NO:11)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS (b) Light chain of anti-albumin Fv component (SEQ ID NO:12)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGCGTKVEIKRT (c) Linker 1 (SEQ ID NO:13)
SGGGGSGGGGTGGGGS (d) Linker 2 (SEQ ID NO:14)
GGGGSGGGGSGGGGS (e) A26 Fab Heavy-(G4S,G4T,G4S)-645dsFv(gH5) (SEQ ID NO:15)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCSGGGGSGGGGTGGGGS
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS (f) A26 Fab Light-(3xG4S)-645dsFv(gL4) (SEQ ID NO:16)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECGGGGSGGGGSGGGGSDIQMTQSP
SSVSASVGDRVTITCQSSPSVWSNFLSWYQQKPGKAPKLLIYEASKLTSGVPSRFSGSGS
GTDFTLTISSLQPEDFATYYCGGGYSSISDTTFGCGTKVEIKRT

Figure 21

(a)     645gH1 heavy chain variable domain (SEQ ID NO:17)
EVQLLESGGGLVQPGGSLRLSCAVSGIDLSNYAINWVRQAPGKCLEWIGIIWASGTTFYA
TWAKGRFTISRDSTTVYLQMNSLRAEDTAVYYCARTVPGYSTAPYFDLWGQGTLVTVS
S (b)     645gL1 light chain variable domain (SEQ ID NO:18)
DIVMTQSPSSVSASVGDRVTITCQSSPSVWSNFLSWYQQKPGKAPKLLIYEASKLTSGVP
SRFKGSGSGTDFTLTISSLQPEDFATYYCGGGYSSISDTTFGCGTKVEIK (c)     A26 Fab Heavy-( 3xG4S)-645dsFv(gH1) (SEQ ID NO:19)
EVQLVESGGGLVQPGGSLRLSCAASGFTFTNYGIHWIRQAPGKGLEWVASISPSGGLTY
YRDSVKGRFTISRDDAKNSPYLQMNSLRAEDTAVYYCATGGEGIFDYWGQGTLVTVSS
ASTKGPSVFPLAPSSKSTSGGTAALGCLVKDYFPEPVTVSWNSGALTSGVHTFPAVLQSS
GLYSLSSVVTVPSSSLGTQTYICNVNHKPSNTKVDKKVEPKSCSGGGGSGGGGSGGGGS
EVQLLESGGGLVQPGGSLRLSCAVSGIDLSNYAINWVRQAPGKCLEWIGIIWASGTTFYA
TWAKGRFTISRDSTTVYLQMNSLRAEDTAVYYCARTVPGYSTAPYFDLWGQGTLVTVS
S (d)     A26 Fab Light-(3xG4S)-645dsFv(gL1) (SEQ ID NO:20)
DIQMTQSPSSLSASVGDRVTITCRATQSIYNALAWYQQKPGKAPKLLIYNANTLHTGVPS
RFSASGSGTDSTLTISSLQPEDFATYYCQQYYDYPLTFGGGTKVEIKRTVAAPSVFIFPPS
DEQLKSGTASVVCLLNNFYPREAKVQWKVDNALQSGNSQESVTEQDSKDSTYSLSSTL
TLSKADYEKHKVYACEVTHQGLSSPVTKSFNRGECSGGGGSGGGGSGGGGSDIVMTQS
PSSVSASVGDRVTITCQSSPSVWSNFLSWYQQKPGKAPKLLIYEASKLTSGVPSRFKGSG
SGTDFTLTISSLQPEDFATYYCGGGYSSISDTTFGCGTKVEIK

Figure 22
a) DNA encoding Heavy chain A26-645(gH5) including *E.coli* OmpA leader (SEQ ID NO:21)
<u>ATGAAGAAGACTGCTATAGCGATCGCAGTGGCGCTAGCTGGTTTCGCCACCGTGGC</u>
<u>GCAAGCT</u>GAAGTTCAGCTGGTCGAGTCTGGAGGCGGGCTTGTCCAGCCTGGAGGGA
GCCTGCGTCTCTCTTGTGCAGCAAGCGGTTTCACGTTCACCAACTACGGTATCCACT
GGATTCGTCAGGCACCAGGTAAAGGTCTGGAATGGGTAGCCTCTATCTCTCCGTCTG
GTGGTCTGACGTACTACCGTGACTCTGTCAAAGGTCGTTTCACCATCTCTCGTGATG
ACGCGAAAAACTCTCCGTACCTGCAAATGAACTCTCTGCGTGCAGAAGATACCGCA
GTGTACTACTGCGCTACTGGTGGTGAAGGTATCTTCGACTACTGGGGTCAGGGTACC
CTGGTAACTGTCTCGAGCGCTTCTACAAAGGGCCCAAGCGTTTTCCCACTGGCTCCG
TCCTCTAAATCCACCTCTGGTGGTACGGCTGCACTGGGTTGCCTGGTGAAAGACTAC
TTCCCAGAACCAGTTACCGTGTCTTGGAACTCTGGTGCACTGACCTCTGGTGTTCAC
ACCTTTCCAGCAGTTCTCCAGTCTTCTGGTCTGTACTCCCTGTCTAGCGTGGTTACCG
TTCCGTCTTCTTCTCTGGGTACTCAGACCTACATCTGCAACGTCAACCACAAACCGTC
CAACACCAAGGTCGACAAAAAGTCGAGCCGAAATCCTGTAGTGGAGGTGGGGGCT
CAGGTGGAGGCGGGACCGGTGGAGGTGGCAGCGAGGTTCAACTGCTTGAGTCTGGA
GGAGGCCTAGTCCAGCCTGGAGGGAGCCTGCGTCTCTCTTGTGCAGTAAGCGGCATC
GACCTGAGCAATTACGCCATCAACTGGGTGAGACAAGCTCCGGGGAAGTGTTTAGA
ATGGATCGGTATAATATGGGCCAGTGGGACGACCTTTTATGCTACATGGGCGAAAG
GAAGGTTTACAATTAGCCGGGACAATAGCAAAAACACCGTGTATCTCCAAATGAAC
TCCTTGCGAGCAGAGGACACGGCGGTGTACTATTGTGCTCGCACTGTCCCAGGTTAT
AGCACTGCACCCTACTTCGATCTGTGGGGACAAGGGACCCTGGTGACTGTTTCAAGT
TAA b) DNA encoding Heavy chain A26-645(gH5) (SEQ ID NO:22)
GAAGTTCAGCTGGTCGAGTCTGGAGGCGGGCTTGTCCAGCCTGGAGGGAGCCTGCG
TCTCTCTTGTGCAGCAAGCGGTTTCACGTTCACCAACTACGGTATCCACTGGATTCGT
CAGGCACCAGGTAAAGGTCTGGAATGGGTAGCCTCTATCTCTCCGTCTGGTGGTCTG
ACGTACTACCGTGACTCTGTCAAAGGTCGTTTCACCATCTCTCGTGATGACGCGAAA
AACTCTCCGTACCTGCAAATGAACTCTCTGCGTGCAGAAGATACCGCAGTGTACTAC
TGCGCTACTGGTGGTGAAGGTATCTTCGACTACTGGGGTCAGGGTACCCTGGTAACT
GTCTCGAGCGCTTCTACAAAGGGCCCAAGCGTTTTCCCACTGGCTCCGTCCTCTAAA
TCCACCTCTGGTGGTACGGCTGCACTGGGTTGCCTGGTGAAAGACTACTTCCCAGAA
CCAGTTACCGTGTCTTGGAACTCTGGTGCACTGACCTCTGGTGTTCACACCTTTCCAG
CAGTTCTCCAGTCTTCTGGTCTGTACTCCCTGTCTAGCGTGGTTACCGTTCCGTCTTCT
TCTCTGGGTACTCAGACCTACATCTGCAACGTCAACCACAAACCGTCCAACACCAAG
GTCGACAAAAAGTCGAGCCGAAATCCTGTAGTGGAGGTGGGGGCTCAGGTGGAGG
CGGGACCGGTGGAGGTGGCAGCGAGGTTCAACTGCTTGAGTCTGGAGGAGGCCTAG
TCCAGCCTGGAGGGAGCCTGCGTCTCTCTTGTGCAGTAAGCGGCATCGACCTGAGCA
ATTACGCCATCAACTGGGTGAGACAAGCTCCGGGGAAGTGTTTAGAATGGATCGGT

Figure 22 (continued)

ATAATATGGGCCAGTGGGACGACCTTTTATGCTACATGGGCGAAAGGAAGGTTTAC
AATTAGCCGGGACAATAGCAAAAACACCGTGTATCTCCAAATGAACTCCTTGCGAG
CAGAGGACACGGCGGTGTACTATTGTGCTCGCACTGTCCCAGGTTATAGCACTGCAC
CCTACTTCGATCTGTGGGGACAAGGGACCCTGGTGACTGTTTCAAGTTAA

Figure 23 a) DNA encoding Light chain A26-645(gL4) including E.coli OmpA leader (SEQ ID NO:23)

<u>ATGAAAAAGACAGCTATCGCAATTGCAGTGGCGTTGGCTGGTTTCGCGACCGTTGCG
CAAGCT</u>GATATCCAGATGACCCAGAGCCCAAGCAGTCTCTCCGCCAGCGTAGGCGA
TCGTGTGACTATTACCTGTCGTGCAACCCAGAGCATCTACAACGCTCTGGCTTGGTA
TCAGCAGAAACCGGGTAAAGCGCCAAAACTCCTGATCTACAACGCGAACACTCTGC
ATACTGGTGTTCCGTCTCGTTTCTCTGCGTCTGGTTCTGGTACGGACTCTACTCTGAC
CATCTCCTCTCCAGCCGGAAGATTTCGCGACCTACTACTGCCAGCAGTACTACGA
TTACCCACTGACGTTTGGTGGTGGTACCAAAGTTGAGATCAAACGTACGGTTGCAGC
TCCATCCGTCTTCATCTTTCCACCGTCTGACGAACAGCTCAAATCTGGTACTGCTTCT
GTCGTTTGCCTCCTGAACAACTTCTATCCGCGTGAAGCGAAAGTCCAGTGGAAAGTC
GACAACGCACTCCAGTCTGGTAACTCTCAGGAATCTGTGACCGAACAGGACTCCAA
AGACTCCACCTACTCTCTGTCTAGCACCCTGACTCTGTCCAAAGCAGACTACGAGAA
ACACAAAGTGTACGCTTGCGAAGTTACCCATCAGGGTCTGAGCTCTCCGGTTACCAA
ATCCTTTAATAGAGGGGAGTGTGGTGGCGGTGGCAGTGGTGGTGGAGGTTCCGGAG
GTGGCGGTTCAGACATACAAATGACCCAGAGTCCTTCATCGGTATCCGCGTCCGTTG
GCGATAGGGTGACTATTACATGTCAAAGCTCTCCTAGCGTCTGGAGCAATTTTCTAT
CCTGGTATCAACAGAAACCGGGGAAGGCTCCAAAACTTCTGATTTATGAAGCCTCG
AAACTCACCAGTGGAGTTCCGTCAAGATTCAGTGGCTCTGGATCAGGGACAGACTTC
ACGTTGACAATCAGTTCGCTGCAACCAGAGGACTTTGCGACCTACTATTGTGGTGGA
GGTTACAGTAGCATAAGTGATACGACATTTGGGTGCGGTACTAAGGTGGAAATCAA
ACGTACCTAA b) DNA encoding Light chain A26-645(gL4) (SEQ ID NO:24)
GATATCCAGATGACCCAGAGCCCAAGCAGTCTCTCCGCCAGCGTAGGCGATCGTGT
GACTATTACCTGTCGTGCAACCCAGAGCATCTACAACGCTCTGGCTTGGTATCAGCA
GAAACCGGGTAAAGCGCCAAAACTCCTGATCTACAACGCGAACACTCTGCATACTG
GTGTTCCGTCTCGTTTCTCTGCGTCTGGTTCTGGTACGGACTCTACTCTGACCATCTC
CTCTCTCCAGCCGGAAGATTTCGCGACCTACTACTGCCAGCAGTACTACGATTACCC
ACTGACGTTTGGTGGTGGTACCAAAGTTGAGATCAAACGTACGGTTGCAGCTCCATC
CGTCTTCATCTTTCCACCGTCTGACGAACAGCTCAAATCTGGTACTGCTTCTGTCGTT
TGCCTCCTGAACAACTTCTATCCGCGTGAAGCGAAAGTCCAGTGGAAAGTCGACAA
CGCACTCCAGTCTGGTAACTCTCAGGAATCTGTGACCGAACAGGACTCCAAAGACTC
CACCTACTCTCTGTCTAGCACCCTGACTCTGTCCAAAGCAGACTACGAGAAACACAA
AGTGTACGCTTGCGAAGTTACCCATCAGGGTCTGAGCTCTCCGGTTACCAAATCCTT
TAATAGAGGGGAGTGTGGTGGCGGTGGCAGTGGTGGTGGAGGTTCCGGAGGTGGCG
GTTCAGACATACAAATGACCCAGAGTCCTTCATCGGTATCCGCGTCCGTTGGCGATA
GGGTGACTATTACATGTCAAAGCTCTCCTAGCGTCTGGAGCAATTTTCTATCCTGGT
ATCAACAGAAACCGGGGAAGGCTCCAAAACTTCTGATTTATGAAGCCTCGAAACTC
ACCAGTGGAGTTCCGTCAAGATTCAGTGGCTCTGGATCAGGGACAGACTTCACGTTG

Figure 23 (continued)

ACAATCAGTTCGCTGCAACCAGAGGACTTTGCGACCTACTATTGTGGTGGAGGTTAC
AGTAGCATAAGTGATACGACATTTGGGTGCGGTACTAAGGTGGAAATCAAACGTAC
CTAA

Figure 24 a) DNA encoding Heavy chain A26-645(gH5) including B72.3 leader sequence (SEQ ID NO:25)
ATGGAATGGTCCTGGGTCTTCCTGTTTTCCTTTCTGTCACAACCGGGGTGCACAGCG
AGGTGCAGCTCGTCGAGTCTGGAGGCGGGCTTGTCCAGCCTGGAGGGAGCCTGCGT
CTCTCTTGTGCAGCAAGCGGTTTCACGTTCACCAACTACGGTATCCACTGGATTCGTC
AGGCACCAGGTAAAGGTCTGGAATGGGTAGCCTCTATCTCTCCGTCTGGTGGTCTGA
CGTACTACCGTGACTCTGTCAAAGGTCGTTTCACCATCTCTCGTGATGACGCGAAAA
ACTCTCCGTACCTGCAGATGAACTCTCTGCGTGCAGAAGATACCGCAGTGTACTACT
GCGCTACTGGTGGTGAAGGTATCTTCGACTACTGGGGTCAGGGTACCCTGGTAACTG
TCTCAAGCGCTTCTACAAAGGGCCCATCGGTCTTCCCCCTGGCACCCTCCTCCAAGA
GCACCTCTGGGGGCACAGCGGCCCTGGGCTGCCTGGTCAAGGACTACTTCCCCGAA
CCGGTGACGGTGTCGTGGAACTCAGGCGCCCTGACCAGCGGCGTGCACACCTTCCC
GGCTGTCCTACAGTCCTCTGGACTCTACTCCCTCAGCAGCGTGGTGACCGTGCCCTC
CAGCAGCTTGGGCACCCAGACCTACATCTGCAACGTGAATCACAAGCCCAGCAACA
CCAAGGTGGACAAGAAAGTTGAGCCCAAATCTTGTTCCGGAGGTGGCGGTTCCGGA
GGTGGCGGTACCGGTGGCGGTGGATCCGAAGTCCAGCTGCTTGAATCCGGAGGCGG
ACTCGTGCAGCCCGGAGGCAGTCTTCGCTTGTCCTGCGCTGTATCTGGAATCGACCT
GAGCAATTACGCCATCAACTGGGTGAGACAGGCACCTGGGAAATGCCTCGAATGGA
TCGGCATTATATGGGCTAGTGGGACGACCTTTTATGCTACATGGGCGAAGGGTAGAT
TCACAATCTCACGGGATAATAGTAAGAACACAGTGTACCTGCAGATGAACTCCCTGC
GAGCAGAGGATACCGCCGTTTACTATTGTGCTCGCACTGTCCCAGGTTATAGCACTG
CACCCTACTTTGATCTGTGGGGCAGGGCACTCTGGTCACCGTCTCGAGTTGA b) DNA encoding Heavy chain A26-645(gH5) (SEQ ID NO:26)
GAGGTGCAGCTCGTCGAGTCTGGAGGCGGGCTTGTCCAGCCTGGAGGGAGCCTGCG
TCTCTCTTGTGCAGCAAGCGGTTTCACGTTCACCAACTACGGTATCCACTGGATTCGT
CAGGCACCAGGTAAAGGTCTGGAATGGGTAGCCTCTATCTCTCCGTCTGGTGGTCTG
ACGTACTACCGTGACTCTGTCAAAGGTCGTTTCACCATCTCTCGTGATGACGCGAAA
AACTCTCCGTACCTGCAGATGAACTCTCTGCGTGCAGAAGATACCGCAGTGTACTAC
TGCGCTACTGGTGGTGAAGGTATCTTCGACTACTGGGGTCAGGGTACCCTGGTAACT
GTCTCAAGCGCTTCTACAAAGGGCCCATCGGTCTTCCCCCTGGCACCCTCCTCCAAG
AGCACCTCTGGGGGCACAGCGGCCCTGGGCTGCCTGGTCAAGGACTACTTCCCCGA
ACCGGTGACGGTGTCGTGGAACTCAGGCGCCCTGACCAGCGGCGTGCACACCTTCC
CGGCTGTCCTACAGTCCTCTGGACTCTACTCCCTCAGCAGCGTGGTGACCGTGCCCT
CCAGCAGCTTGGGCACCCAGACCTACATCTGCAACGTGAATCACAAGCCCAGCAAC
ACCAAGGTGGACAAGAAAGTTGAGCCCAAATCTTGTTCCGGAGGTGGCGGTTCCGG
AGGTGGCGGTACCGGTGGCGGTGGATCCGAAGTCCAGCTGCTTGAATCCGGAGGCG
GACTCGTGCAGCCCGGAGGCAGTCTTCGCTTGTCCTGCGCTGTATCTGGAATCGACC
TGAGCAATTACGCCATCAACTGGGTGAGACAGGCACCTGGGAAATGCCTCGAATGG
ATCGGCATTATATGGGCTAGTGGGACGACCTTTTATGCTACATGGGCGAAGGGTAGA Figure 24 (continued)

TTCACAATCTCACGGGATAATAGTAAGAACACAGTGTACCTGCAGATGAACTCCCTG
CGAGCAGAGGATACCGCCGTTTACTATTGTGCTCGCACTGTCCCAGGTTATAGCACT
GCACCCTACTTTGATCTGTGGGGGCAGGGCACTCTGGTCACCGTCTCGAGTTGA

Figure 25
a) DNA encoding Light chain A26-645(gL4) including B72.3 leader sequence (SEQ ID NO:27)
<u>ATGTCAGTTCCCACACAGGTGCTGGGCCTGCTTCTGTTGTGGCTCACCGATGCTAGG
TGT</u>GATATCCAGATGACCCAGAGTCCAAGCAGTCTCTCCGCCAGCGTAGGCGATCGT
GTGACTATTACCTGTCGTGCAACCCAGAGCATCTACAACGCTCTGGCTTGGTATCAG
CAGAAACCGGGTAAAGCGCCAAAACTCCTGATCTACAACGCGAACACTCTGCATAC
CGGTGTTCCGTCTCGTTTCTCTGCGTCTGGTTCTGGTACGGACTCTACTCTGACCATC
TCCTCTCTGCAGCCGGAAGATTTCGCGACCTACTACTGCCAGCAGTACTACGATTAC
CCACTGACGTTTGGTGGTGGTACCAAAGTTGAGATCAAACGTACGGTGGCTGCACCA
TCTGTCTTCATCTTCCCCCCATCTGATGAGCAGTTGAAGTCTGGCACTGCCTCTGTTG
TGTGCCTGCTGAATAACTTCTACCCTAGAGAGGCCAAAGTCCAGTGGAAGGTGGAT
AACGCCCTTCAATCCGGAAACTCCCAGGAGAGTGTCACTGAGCAGGACTCAAAGGA
CTCCACCTATAGCCTTAGCAGCACACTGACACTGAGCAAGGCTGACTACGAGAAAC
ACAAGGTCTACGCCTGCGAAGTGACACATCAAGGCCTGAGCTCACCCGTGACAAAG
AGCTTTAACAGGGGAGAGTGTGGTGGAGGTGGCTCTGGCGGTGGTGGCTCCGGAGG
CGGAGGAAGCGACATCCAGATGACCCAGAGCCCTTCCTCTGTAAGCGCCAGTGTCG
GAGACAGAGTGACTATTACCTGCCAAAGCTCCCCTTCAGTCTGGTCCAATTTTCTAT
CCTGGTACCAGCAAAAGCCCGGAAAGGCTCCTAAATTGCTGATCTACGAAGCAAGC
AAACTCACCAGCGGCGTGCCCAGCAGGTTCAGCGGCAGTGGGTCTGGAACTGACTT
TACCCTGACAATCTCCTCACTCCAGCCCGAGGACTTCGCCACCTATTACTGCGGTGG
AGGTTACAGTAGCATAAGTGATACGACATTTGGATGCGGCACTAAAGTGGAAATCA
AGCGTACCTGA b) DNA encoding Light chain A26-645(gL4) (SEQ ID NO:28)
GATATCCAGATGACCCAGAGTCCAAGCAGTCTCTCCGCCAGCGTAGGCGATCGTGT
GACTATTACCTGTCGTGCAACCCAGAGCATCTACAACGCTCTGGCTTGGTATCAGCA
GAAACCGGGTAAAGCGCCAAAACTCCTGATCTACAACGCGAACACTCTGCATACCG
GTGTTCCGTCTCGTTTCTCTGCGTCTGGTTCTGGTACGGACTCTACTCTGACCATCTC
CTCTCTGCAGCCGGAAGATTTCGCGACCTACTACTGCCAGCAGTACTACGATTACCC
ACTGACGTTTGGTGGTGGTACCAAAGTTGAGATCAAACGTACGGTGGCTGCACCATC
TGTCTTCATCTTCCCCCCATCTGATGAGCAGTTGAAGTCTGGCACTGCCTCTGTTGTG
TGCCTGCTGAATAACTTCTACCCTAGAGAGGCCAAAGTCCAGTGGAAGGTGGATAA
CGCCCTTCAATCCGGAAACTCCCAGGAGAGTGTCACTGAGCAGGACTCAAAGGACT
CCACCTATAGCCTTAGCAGCACACTGACACTGAGCAAGGCTGACTACGAGAAACAC
AAGGTCTACGCCTGCGAAGTGACACATCAAGGCCTGAGCTCACCCGTGACAAAGAG
CTTTAACAGGGGAGAGTGTGGTGGAGGTGGCTCTGGCGGTGGTGGCTCCGGAGGCG
GAGGAAGCGACATCCAGATGACCCAGAGCCCTTCCTCTGTAAGCGCCAGTGTCGGA
GACAGAGTGACTATTACCTGCCAAAGCTCCCCTTCAGTCTGGTCCAATTTTCTATCCT
GGTACCAGCAAAAGCCCGGAAAGGCTCCTAAATTGCTGATCTACGAAGCAAGCAAA
CTCACCAGCGGCGTGCCCAGCAGGTTCAGCGGCAGTGGGTCTGGAACTGACTTTACC

Figure 25 (continued)

CTGACAATCTCCTCACTCCAGCCCGAGGACTTCGCCACCTATTACTGCGGTGGAGGT
TACAGTAGCATAAGTGATACGACATTTGGATGCGGCACTAAAGTGGAAATCAAGCG
TACCTGA

FIGURE 26
(a) Heavy chain variable domain of anti-albumin antibody (no ds) (SEQ ID NO:29)
EVQLLESGGGLVQPGGSLRLSCAVSGIDLSNYAINWVRQAPGKGLEWIGIIWASGTTFY
ATWAKGRFTISRDNSKNTVYLQMNSLRAEDTAVYYCARTVPGYSTAPYFDLWGQGTL
VTVSS
(b) Heavy chain variable domain of anti-albumin antibody (ds) (SEQ ID NO:30)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSS
(c) Light chain variable domain of anti-albumin antibody (no ds) (SEQ ID NO:31)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGGGTKVEIKRT
(d) Light chain variable domain of anti-albumin antibody (ds) (SEQ ID NO:32)
DIQMTQSPSSVSASVGDRVTITCQSSPSVWSNFLSWYQQKPGKAPKLLIYEASKLTSGVP
SRFSGSGSGTDFTLTISSLQPEDFATYYCGGGYSSISDTTFGCGTKVEIKRT (e) Linker 1 (SEQ ID NO:33)     SGGGGSGGGGTGGGGS
(f) Linker 2 (SEQ ID NO:34)     GGGGSGGGGSGGGGS 645 gH5gL4 specific to albumin (SEQ ID NO: 35)
GAGGTTCAGCTGCTGGAGTCTGGAGGCGGGCTTGTCCAGCCTGGAGGGAGCCTGCG
TCTCTCTTGTGCAGTAAGCGGCATCGACCTGTCCAACTACGCGATTAACTGGGTACG
TCAGGCACCGGGTAAAGGTCTGGAATGGATCGGCATCATCTGGGCCTCTGGTACGA
CCTTCTACGCTACTTGGGCCAAAGGTCGTTTCACCATCTCCCGTGACAACTCTAAAA
ACACCGTGTACCTGCAGATGAACTCTCTGCGTGCGGAAGACACTGCGGTTTACTATT
GCGCGCGTACCGTTCCGGGCTATTCTACTGCACCGTACTTCGACCTGTGGGGTCAGG
GTACTCTGGTTACCGTCTCGAGTGGAGGTGGCGGTTCTGGCGGTGGCGGTTCCGGTG
GCGGTGGATCGGGAGGTGGCGGTTCTGATATCCAGATGACCCAGAGTCCAAGCAGT
GTTTCCGCCAGCGTAGGCGATCGTGTGACTATTACCTGTCAGTCCTCTCCGAGCGTTT
GGTCCAACTTCCTGAGCTGGTACCAGCAGAAACCGGGTAAAGCCCCGAAACTGCTG
ATCTACGAGGCGTCTAAACTGACCTCTGGTGTACCGTCCCGTTTCTCTGGCTCTGGCT
CTGGTACGGACTTCACTCTGACCATCTCCTCTCTGCAGCCGGAAGACTTTGCAACGT

Figure 26 (continued)

ACTACTGCGGTGGTGGTTACTCTTCCATCTCTGACACCACGTTCGGTGGAGGCACCA
AAGTTGAAATCAAACGTACGCATCACCATCACCATCACCATCAC 645 gH5gL4 specific to albumin (SEQ ID NO: 36)
EVQLLESGGGLVQPGGSLRLSCAVSGIDLSNYAINWVRQAPGKGLEWIGIIWASGTTFY
ATWAKGRFTISRDNSKNTVYLQMNSLRAEDTAVYYCARTVPGYSTAPYFDLWGQGTL
VTVSSGGGGSGGGGSGGGGSGGGGSDIQMTQSPSSVSASVGDRVTITCQSSPSVWSNFL
SWYQQKPGKAPKLLIYEASKLTSGVPSRFSGSGSGTDFTLTISSLQPEDFATYYCGGGYS
SISDTTFGGGTKVEIKRTHHHHHHHHHH 645 gH5gL4ds specific to albumin (SEQ ID NO: 37)
GAGGTTCAGCTGCTGGAGTCTGGAGGCGGGCTTGTCCAGCCTGGAGGGAGCCTGCG
TCTCTCTTGTGCAGTAAGCGGCATCGACCTGTCCAACTACGCGATTAACTGGGTACG
TCAGGCACCGGGTAAATGCCTGGAATGGATCGGCATCATCTGGGCCTCTGGTACGAC
CTTCTACGCTACTTGGGCCAAAGGTCGTTTCACCATCTCCCGTGACAACTCTAAAAA
CACCGTGTACCTGCAGATGAACTCTCTGCGTGCGGAAGACACTGCGGTTTACTATTG
CGCGCGTACCGTTCCGGGCTATTCTACTGCACCGTACTTCGACCTGTGGGGTCAGGG
TACTCTGGTTACCGTCTCGAGTGGAGGTGGCGGTTCTGGCGGTGGCGGTTCCGGTGG
CGGTGGATCGGGAGGTGGCGGTTCTGATATCCAGATGACCCAGAGTCCAAGCAGTG
TTTCCGCCAGCGTAGGCGATCGTGTGACTATTACCTGTCAGTCCTCTCCGAGCGTTTG
GTCCAACTTCCTGAGCTGGTACCAGCAGAAACCGGGTAAAGCCCCGAAACTGCTGA
TCTACGAGGCGTCTAAACTGACCTCTGGTGTACCGTCCCGTTTCTCTGGCTCTGGCTC
TGGTACGGACTTCACTCTGACCATCTCCTCTCTGCAGCCGGAAGACTTTGCAACGTA
CTACTGCGGTGGTGGTTACTCTTCCATCTCTGACACCACGTTCGGTTGTGGCACCAA
AGTTGAAATCAAACGTACGCATCACCATCACCATCACCATCAC 645 gH5gL4ds specific to albumin (SEQ ID NO: 38)
EVQLLESGGGLVQPGGSLRLSCAVSGIDLSNYAINWVRQAPGKCLEWIGIIWASGTTFYA
TWAKGRFTISRDNSKNTVYLQMNSLRAEDTAVYYCARTVPGYSTAPYFDLWGQGTLV
TVSSGGGGSGGGGSGGGGSGGGG

FIGURE 27
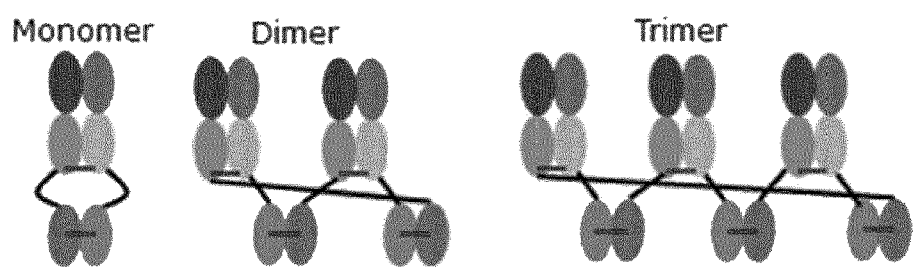
Fab = Heavy and Light Chain of Fab with a disulfide bond between the heavy and light chain and linkers joined to C-terminus of the constant region of the heavy chain and light chain to join to the dsFv
dsFv = disulfide stabilised Fv and linkers to join to the Fab FIGURE 28
Fab-2x dsscFv formats and Fab-dsscFv-dsFv format
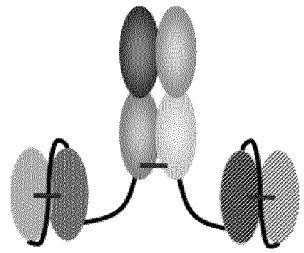
Fab#2-(HC)-dsscFv#3-(LC)-dsscFv#4
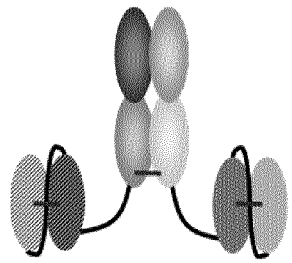
Fab#2-(LC)-dsscFv#3-(HC)-dsscFv#4
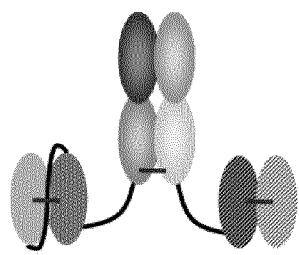
Fab-(HC)dsscFv-(LC)dsFv
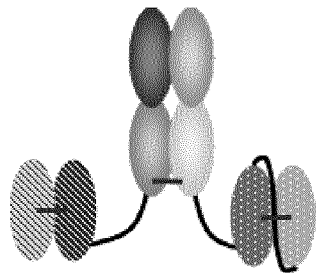
Fab-(HC)dsFv-(LC)dsscFv Fab(HC)-LHdsscFv    Fab(HC)-HLdsscFv    Fab(LC)-LHdsscFv    Fab(LC)-HLdsscFv

```
                          SEQUENCE LISTING

<160> NUMBER OF SEQ ID NOS: 90

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1

Asn Tyr Gly Ile His
1               5

<210> SEQ ID NO 2
<211> LENGTH: 17
<212> TYPE: PRT
<213> ORGANISM: Artificial
<220> FEATURE:
<223> OTHER INFORMATION: CDRH2

<400> SEQUENCE: 2

Ser Ile Ser Pro Ser Gly Gly Leu Thr Tyr Tyr Arg Asp Ser Val Lys
1               5                   10                  15

Gly

<210> SEQ ID NO 3
<211> LENGTH: 8
<212> TYPE: PRT
<213> ORGANISM: Artificial
<220> FEATURE:
<223> OTHER INFORMATION: CDRH3

<400> SEQUENCE: 3

Gly Gly Glu Gly Ile Phe Asp Tyr
1               5

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Arg Ala Thr Gln Ser Ile Tyr Asn Ala Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

Asn Ala Asn Thr Leu His Thr
1               5

<210> SEQ ID NO 6
<211> LENGTH: 9
<212> TYPE: PRT
```

-continued

<213> ORGANISM: Artificial
<220> FEATURE:
<223> OTHER INFORMATION: CDRL3

<400> SEQUENCE: 6

Gln Gln Tyr Tyr Asp Tyr Pro Leu Thr
1               5

<210> SEQ ID NO 7
<211> LENGTH: 108
<212> TYPE: PRT
<213> ORGANISM: Artificial
<220> FEATURE:
<223> OTHER INFORMATION: Light chain variable region of antibody A26

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg
            100                 105

<210> SEQ ID NO 8
<211> LENGTH: 117
<212> TYPE: PRT
<213> ORGANISM: Artificial
<220> FEATURE:
<223> OTHER INFORMATION: Heavy chain variable region of antibody A26

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser
        115

<210> SEQ ID NO 9
<211> LENGTH: 214
<212> TYPE: PRT
<213> ORGANISM: Artificial

```
<220> FEATURE:
<223> OTHER INFORMATION: Light chain of anti-OX40 antibody Fab component

<400> SEQUENCE: 9

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
    50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 10
<211> LENGTH: 220
<212> TYPE: PRT
<213> ORGANISM: Artificial
<220> FEATURE:
<223> OTHER INFORMATION: Heavy chain of anti-OX40 antibody Fab component

<400> SEQUENCE: 10

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
```

```
                115                 120                 125
Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Val Val Thr Val Pro Ser Ser Ser
        180                 185                 190

Leu Gly Thr Gln Thr Tyr Ile Cys Asn Val Asn His Lys Pro Ser Asn
                195                 200                 205

Thr Lys Val Asp Lys Lys Val Glu Pro Lys Ser Cys
        210                 215                 220
```

<210> SEQ ID NO 11
<211> LENGTH: 121
<212> TYPE: PRT
<213> ORGANISM: Artificial
<220> FEATURE:
<223> OTHER INFORMATION: Heavy chain of anti-albumin Fv component

<400> SEQUENCE: 11

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120
```

<210> SEQ ID NO 12
<211> LENGTH: 112
<212> TYPE: PRT
<213> ORGANISM: Artificial
<220> FEATURE:
<223> OTHER INFORMATION: Light chain of anti-albumin Fv component

<400> SEQUENCE: 12

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
            20                  25                  30

Phe Leu Ser Trp Tyr Gln Gln Lys Pro Gly Lys Ala Pro Lys Leu Leu
        35                  40                  45

Ile Tyr Glu Ala Ser Lys Leu Thr Gly Val Pro Ser Arg Phe Ser
    50                  55                  60

Gly Ser Gly Ser Gly Thr Asp Phe Thr Leu Thr Ile Ser Ser Leu Gln
65                  70                  75                  80
```

```
Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys Arg Thr
            100                 105                 110

<210> SEQ ID NO 13
<211> LENGTH: 16
<212> TYPE: PRT
<213> ORGANISM: Artificial
<220> FEATURE:
<223> OTHER INFORMATION: Linker 1

<400> SEQUENCE: 13

Ser Gly Gly Gly Gly Ser Gly Gly Gly Thr Gly Gly Gly Gly Ser
1               5                   10                  15

<210> SEQ ID NO 14
<211> LENGTH: 15
<212> TYPE: PRT
<213> ORGANISM: Artificial
<220> FEATURE:
<223> OTHER INFORMATION: Linker 2

<400> SEQUENCE: 14

Gly Gly Gly Gly Ser Gly Gly Gly Gly Ser Gly Gly Gly Gly Ser
1               5                   10                  15

<210> SEQ ID NO 15
<211> LENGTH: 357
<212> TYPE: PRT
<213> ORGANISM: Artificial
<220> FEATURE:
<223> OTHER INFORMATION: A26 Fab Heavy-(G4S,G4T,G4S)-645dsFv(gH5)

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
```

```
                195                 200                 205
Thr Lys Val Asp Lys Lys Val Glu Pro Lys Ser Cys Gly Gly Gly
    210                 215                 220
Gly Ser Gly Gly Gly Thr Gly Gly Gly Ser Glu Val Gln Leu
225                 230                 235                 240
Leu Glu Ser Gly Gly Leu Val Gln Pro Gly Gly Ser Leu Arg Leu
                245                 250                 255
Ser Cys Ala Val Ser Gly Ile Asp Leu Ser Asn Tyr Ala Ile Asn Trp
                260                 265                 270
Val Arg Gln Ala Pro Gly Lys Cys Leu Glu Trp Ile Gly Ile Ile Trp
                275                 280                 285
Ala Ser Gly Thr Thr Phe Tyr Ala Thr Trp Ala Lys Gly Arg Phe Thr
                290                 295                 300
Ile Ser Arg Asp Asn Ser Lys Asn Thr Val Tyr Leu Gln Met Asn Ser
305                 310                 315                 320
Leu Arg Ala Glu Asp Thr Ala Val Tyr Tyr Cys Ala Arg Thr Val Pro
                325                 330                 335
Gly Tyr Ser Thr Ala Pro Tyr Phe Asp Leu Trp Gly Gln Gly Thr Leu
                340                 345                 350
Val Thr Val Ser Ser
                355

<210> SEQ ID NO 16
<211> LENGTH: 341
<212> TYPE: PRT
<213> ORGANISM: Artificial
<220> FEATURE:
<223> OTHER INFORMATION: A26 Fab Light-(3xG4S)-645dsFv(gL4)

<400> SEQUENCE: 16

Asp Ile Gln Met Thr Gln Ser Pro Ser Ser Leu Ser Ala Ser Val Gly
1               5                   10                  15
Asp Arg Val Thr Ile Thr Cys Arg Ala Thr Gln Ser Ile Tyr Asn Ala
                20                  25                  30
Leu Ala Trp Tyr Gln Gln Lys Pro Gly Lys Ala Pro Lys Leu Leu Ile
                35                  40                  45
Tyr Asn Ala Asn Thr Leu His Thr Gly Val Pro Ser Arg Phe Ser Ala
50                  55                  60
Ser Gly Ser Gly Thr Asp Ser Thr Leu Thr Ile Ser Ser Leu Gln Pro
65                  70                  75                  80
Glu Asp Phe Ala Thr Tyr Tyr Cys Gln Gln Tyr Tyr Asp Tyr Pro Leu
                85                  90                  95
Thr Phe Gly Gly Gly Thr Lys Val Glu Ile Lys Arg Thr Val Ala Ala
                100                 105                 110
Pro Ser Val Phe Ile Phe Pro Pro Ser Asp Glu Gln Leu Lys Ser Gly
                115                 120                 125
Thr Ala Ser Val Val Cys Leu Leu Asn Asn Phe Tyr Pro Arg Glu Ala
                130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
                180                 185                 190
Ala Cys Glu Val Thr His Gln Gly Leu Ser Ser Pro Val Thr Lys Ser
```

```
                195                 200                 205
Phe Asn Arg Gly Glu Cys Gly Gly Gly Ser Gly Gly Gly Ser
    210                 215                 220
Gly Gly Gly Gly Ser Asp Ile Gln Met Thr Gln Ser Pro Ser Ser Val
225                 230                 235                 240
Ser Ala Ser Val Gly Asp Arg Val Thr Ile Thr Cys Gln Ser Ser Pro
                245                 250                 255
Ser Val Trp Ser Asn Phe Leu Ser Trp Tyr Gln Gln Lys Pro Gly Lys
            260                 265                 270
Ala Pro Lys Leu Leu Ile Tyr Glu Ala Ser Lys Leu Thr Ser Gly Val
        275                 280                 285
Pro Ser Arg Phe Ser Gly Ser Gly Ser Gly Thr Asp Phe Thr Leu Thr
    290                 295                 300
Ile Ser Ser Leu Gln Pro Glu Asp Phe Ala Thr Tyr Tyr Cys Gly Gly
305                 310                 315                 320
Gly Tyr Ser Ser Ile Ser Asp Thr Thr Phe Gly Cys Gly Thr Lys Val
                325                 330                 335
Glu Ile Lys Arg Thr
                340
```

<210> SEQ ID NO 17
<211> LENGTH: 119
<212> TYPE: PRT
<213> ORGANISM: Artificial
<220> FEATURE:
<223> OTHER INFORMATION: 645gH1 heavy chain variable domain

<400> SEQUENCE: 17

```
Glu Val Gln Leu Leu Glu Ser Gly Gly Gly Leu Val Gln Pro Gly Gly
1               5                   10                  15
Ser Leu Arg Leu Ser Cys Ala Val Ser Gly Ile Asp Leu Ser Asn Tyr
            20                  25                  30
Ala Ile Asn Trp Val Arg Gln Ala Pro Gly Lys Cys Leu Glu Trp Ile
        35                  40                  45
Gly Ile Ile Trp Ala Ser Gly Thr Thr Phe Tyr Ala Thr Trp Ala Lys
    50                  55                  60
Gly Arg Phe Thr Ile Ser Arg Asp Ser Thr Thr Val Tyr Leu Gln Met
65                  70                  75                  80
Asn Ser Leu Arg Ala Glu Asp Thr Ala Val Tyr Tyr Cys Ala Arg Thr
                85                  90                  95
Val Pro Gly Tyr Ser Thr Ala Pro Tyr Phe Asp Leu Trp Gly Gln Gly
            100                 105                 110
Thr Leu Val Thr Val Ser Ser
        115
```

<210> SEQ ID NO 18
<211> LENGTH: 110
<212> TYPE: PRT
<213> ORGANISM: Artificial
<220> FEATURE:
<223> OTHER INFORMATION: 645gL1 light chain variable domain

<400> SEQUENCE: 18

```
Asp Ile Val Met Thr Gln Ser Pro Ser Ser Val Ser Ala Ser Val Gly
1               5                   10                  15
Asp Arg Val Thr Ile Thr Cys Gln Ser Ser Pro Ser Val Trp Ser Asn
            20                  25                  30
```

```
Phe Leu Ser Trp Tyr Gln Gln Lys Pro Gly Lys Ala Pro Lys Leu Leu
         35                  40                  45

Ile Tyr Glu Ala Ser Lys Leu Thr Ser Gly Val Pro Ser Arg Phe Lys
 50                  55                  60

Gly Ser Gly Ser Gly Thr Asp Phe Thr Leu Thr Ile Ser Ser Leu Gln
 65                  70                  75                  80

Pro Glu Asp Phe Ala Thr Tyr Tyr Cys Gly Gly Tyr Ser Ser Ile
                 85                  90                  95

Ser Asp Thr Thr Phe Gly Cys Gly Thr Lys Val Glu Ile Lys
                100                 105                 110

<210> SEQ ID NO 19
<211> LENGTH: 355
<212> TYPE: PRT
<213> ORGANISM: Artificial
<220> FEATURE:
<223> OTHER INFORMATION: A26 Fab Heavy-(3xG4S)-645dsFv(gH1)

<400> SEQUENCE: 19

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Thr Asn Tyr
             20                  25                  30

Gly Ile His Trp Ile Arg Gln Ala Pro Gly Lys Gly Leu Glu Trp Val
         35                  40                  45

Ala Ser Ile Ser Pro Ser Gly Gly Leu Thr Tyr Tyr Arg Asp Ser Val
 50                  55                  60

Lys Gly Arg Phe Thr Ile Ser Arg Asp Asp Ala Lys Asn Ser Pro Tyr
 65                  70                  75                  80

Leu Gln Met Asn Ser Leu Arg Ala Glu Asp Thr Ala Val Tyr Tyr Cys
             85                  90                  95

Ala Thr Gly Gly Glu Gly Ile Phe Asp Tyr Trp Gly Gln Gly Thr Leu
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Ser Gly Gly Gly
    210                 215                 220

Gly Ser Gly Gly Gly Gly Ser Gly Gly Gly Gly Ser Glu Val Gln Leu
225                 230                 235                 240

Leu Glu Ser Gly Gly Gly Leu Val Gln Pro Gly Gly Ser Leu Arg Leu
                245                 250                 255

Ser Cys Ala Val Ser Gly Ile Asp Leu Ser Asn Tyr Ala Ile Asn Trp
            260                 265                 270

Val Arg Gln Ala Pro Gly Lys Cys Leu Glu Trp Ile Gly Ile Ile Trp
        275                 280                 285
```

```
Ala Ser Gly Thr Thr Phe Tyr Ala Thr Trp Ala Lys Gly Arg Phe Thr
    290                 295                 300
Ile Ser Arg Asp Ser Thr Thr Val Tyr Leu Gln Met Asn Ser Leu Arg
305                 310                 315                 320
Ala Glu Asp Thr Ala Val Tyr Tyr Cys Ala Arg Thr Val Pro Gly Tyr
                325                 330                 335
Ser Thr Ala Pro Tyr Phe Asp Leu Trp Gly Gln Gly Thr Leu Val Thr
                340                 345                 350
Val Ser Ser
        355

<210> SEQ ID NO 20
<211> LENGTH: 340
<212> TYPE: PRT
<213> ORGANISM: Artificial
<220> FEATURE:
<223> OTHER INFORMATION: A26 Fab Light-(3xG4S)-645dsFv(gL1)

<400> SEQUENCE: 20

Asp Ile Gln Met Thr Gln Ser Pro Ser Ser Leu Ser Ala Ser Val Gly
1               5                   10                  15
Asp Arg Val Thr Ile Thr Cys Arg Ala Thr Gln Ser Ile Tyr Asn Ala
            20                  25                  30
Leu Ala Trp Tyr Gln Gln Lys Pro Gly Lys Ala Pro Lys Leu Leu Ile
        35                  40                  45
Tyr Asn Ala Asn Thr Leu His Thr Gly Val Pro Ser Arg Phe Ser Ala
50                  55                  60
Ser Gly Ser Gly Thr Asp Ser Thr Leu Thr Ile Ser Ser Leu Gln Pro
65                  70                  75                  80
Glu Asp Phe Ala Thr Tyr Tyr Cys Gln Gln Tyr Tyr Asp Tyr Pro Leu
                85                  90                  95
Thr Phe Gly Gly Gly Thr Lys Val Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys Ser Gly Gly Gly Ser Gly Gly Gly Gly
    210                 215                 220
Ser Gly Gly Gly Gly Ser Asp Ile Val Met Thr Gln Ser Pro Ser Ser
225                 230                 235                 240
Val Ser Ala Ser Val Gly Asp Arg Val Thr Ile Thr Cys Gln Ser Ser
                245                 250                 255
Pro Ser Val Trp Ser Asn Phe Leu Ser Trp Tyr Gln Gln Lys Pro Gly
            260                 265                 270
Lys Ala Pro Lys Leu Leu Ile Tyr Glu Ala Ser Lys Leu Thr Ser Gly
        275                 280                 285
```

```
Val Pro Ser Arg Phe Lys Gly Ser Gly Ser Gly Thr Asp Phe Thr Leu
        290                 295                 300

Thr Ile Ser Ser Leu Gln Pro Glu Asp Phe Ala Thr Tyr Tyr Cys Gly
305                 310                 315                 320

Gly Gly Tyr Ser Ser Ile Ser Asp Thr Thr Phe Gly Cys Gly Thr Lys
            325                 330                 335

Val Glu Ile Lys
            340

<210> SEQ ID NO 21
<211> LENGTH: 1137
<212> TYPE: DNA
<213> ORGANISM: Artificial
<220> FEATURE:
<223> OTHER INFORMATION: Heavy chain A26-645(gH5) including E.coli OmpA
      leader

<400> SEQUENCE: 21
atgaagaaga ctgctatagc gatcgcagtg gcgctagctg ttttcgccac cgtggcgcaa       60
gctgaagttc agctggtcga gtctggaggc gggcttgtcc agcctggagg gagcctgcgt      120
ctctcttgtg cagcaagcgg tttcacgttc accaactacg gtatccactg gattcgtcag      180
gcaccaggta aggtctggaa tgggtagcc tctatctctc cgtctggtgg tctgacgtac       240
taccgtgact ctgtcaaagg tcgtttcacc atctctcgtg atgacgcgaa aaactctccg      300
tacctgcaaa tgaactctct gcgtgcagaa gataccgcag tgtactactg cgctactggt      360
ggtgaaggta tcttcgacta ctggggtcag ggtaccctgg taactgtctc gagcgcttct      420
acaaagggcc aagcgttttt cccactggct ccgtcctcta atccacctc tggtggtacg       480 gctgcactgg gttgcctggt gaaagactac ttcccagaac cagttaccgt gtcttggaac      540
tctggtgcac tgacctctgg tgttcacacc tttccagcag ttctccagtc ttctggtctg      600
tactccctgt ctagcgtggt taccgttccg tcttcttctc tgggtactca gacctacatc      660
tgcaacgtca accacaaacc gtccaacacc aaggtcgaca aaaagtcga gccgaaatcc       720 tgtagtggag gtggggctc aggtggaggc gggaccggtg gaggtggcag cgaggttcaa      780
ctgcttgagt ctggaggagg cctagtccag cctggaggga gcctgcgtct ctcttgtgca      840
gtaagcggca tcgacctgag caattacgcc atcaactggg tgagacaagc tccggggaag      900
tgtttagaat ggatcggtat aatatgggcc agtgggacga ccttttatgc tacatgggcg      960
aaaggaaggt ttacaattag ccgggacaat agcaaaaaca ccgtgtatct ccaaatgaac     1020
tccttgcgag cagaggacac ggcggtgtac tattgtgctc gcactgtccc aggttatagc     1080
actgcaccct acttcgatct gtggggacaa gggaccctgg tgactgtttc aagttaa       1137

<210> SEQ ID NO 22
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 22
gaagttcagc tggtcgagtc tggaggcggg cttgtccagc ctggagggag cctgcgtctc       60
tcttgtgcag caagcggttt cacgttcacc aactacggta tccactggat tcgtcaggca      120
ccaggtaaag gtctggaatg ggtagcctct atctctccgt ctggtggtct gacgtactac      180
cgtgactctg tcaaaggtcg tttcaccatc tctcgtgatg acgcgaaaaa ctctccgtac      240
```

```
ctgcaaatga actctctgcg tgcagaagat accgcagtgt actactgcgc tactggtggt      300
gaaggtatct tcgactactg gggtcagggt accctggtaa ctgtctcgag cgcttctaca      360
aagggcccaa gcgttttccc actggctccg tcctctaaat ccacctctgg tggtacggct      420
gcactgggtt gcctggtgaa agactacttc ccagaaccag ttaccgtgtc ttggaactct      480
ggtgcactga cctctggtgt tcacaccttt ccagcagttc tccagtcttc tggtctgtac      540
tccctgtcta gcgtggttac cgttccgtct tcttctctgg gtactcagac ctacatctgc      600
aacgtcaacc acaaaccgtc caacaccaag gtcgacaaaa aagtcgagcc gaaatcctgt      660
agtggaggtg ggggctcagg tggaggcggg accggtggag gtggcagcga ggttcaactg      720
cttgagtctg gaggaggcct agtccagcct ggagggagcc tgcgtctctc ttgtgcagta      780
agcggcatcg acctgagcaa ttacgccatc aactgggtga caagctcc ggggaagtgt       840 ttagaatgga tcggtataat atgggccagt gggacgacct tttatgctac atgggcgaaa      900
ggaaggttta caattagccg ggacaatagc aaaaacaccg tgtatctcca aatgaactcc      960
ttgcgagcag aggacacggc ggtgtactat tgtgctcgca ctgtcccagg ttatagcact     1020
gcaccctact cgatctgtg gggacaaggg accctggtga ctgtttcaag ttaa           1074

<210> SEQ ID NO 23
<211> LENGTH: 1089
<212> TYPE: DNA
<213> ORGANISM: Artificial
<220> FEATURE:
<223> OTHER INFORMATION: Light chain A26-645(gL4) including E.coli OmpA
      leader

<400> SEQUENCE: 23
atgaaaaaga cagctatcgc aattgcagtg gcgttggctg gtttcgcgac cgttgcgcaa       60
gctgatatcc agatgaccca gagcccaagc agtctctccg ccagcgtagg cgatcgtgtg      120
actattacct gtcgtgcaac ccagagcatc tacaacgctc tggcttggta tcagcagaaa      180
ccgggtaaag cgccaaaact cctgatctac aacgcgaaca ctctgcatac tggtgttccg      240
tctcgtttct ctgcgtctgg ttctggtacg gactctactc tgaccatctc ctctctccag      300
ccggaagatt tcgcgaccta ctactgccag cagtactacg attacccact gacgtttggt      360
ggtggtacca agttgagat caaacgtacg gttgcagctc catccgtctt catctttcca      420
ccgtctgacg aacagctcaa atctggtact gcttctgtcg tttgcctcct gaacaacttc      480
tatccgcgtg aagcgaaagt ccagtggaaa gtcgacaacg cactccagtc tggtaactct      540
caggaatctg tgaccgaaca ggactccaaa gactccacct actctctgtc tagcaccctg      600
actctgtcca agcagacta cgagaaacac aaagtgtacg cttgcgaagt tacccatcag      660
ggtctgagct ctccggttac caaatccttt aatagagggg agtgtggtgg cggtggcagt      720
ggtggtggag gttccggagg tggcggttca gacatacaaa tgacccagag tccttcatcg     780
gtatccgcgt ccgttggcga tagggtgact attacatgtc aaagctctcc tagcgtctgg      840
agcaattttc tatcctggta tcaacagaaa ccggggaagg ctccaaaact tctgatttat      900
gaagcctcga aactcaccag tggagttccg tcaagattca gtggctctgg atcagggaca      960
gacttcacgt tgacaatcag ttcgctgcaa ccagaggact ttgcgaccta ctattgtggt     1020
ggaggttaca gtagcataag tgatacgaca tttgggtgcg gtactaaggt ggaaatcaaa     1080
cgtacctaa                                                             1089

<210> SEQ ID NO 24
```

```
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 24
gatatccaga tgacccagag cccaagcagt ctctccgcca gcgtaggcga tcgtgtgact      60
attacctgtc gtgcaaccca gagcatctac aacgctctgg cttggtatca gcagaaaccg     120
ggtaaagcgc caaaactcct gatctacaac gcgaacactc tgcatactgg tgttccgtct     180
cgtttctctg cgtctggttc tggtacggac tctactctga ccatctcctc tctccagccg     240
gaagatttcg cgacctacta ctgccagcag tactacgatt acccactgac gtttggtggt     300
ggtaccaaag ttgagatcaa acgtacggtt gcagctccat ccgtcttcat ctttccaccg     360
tctgacgaac agctcaaatc tggtactgct tctgtcgttt gcctcctgaa caacttctat     420
ccgcgtgaag cgaaagtcca gtggaaagtc gacaacgcac tccagtctgg taactctcag     480
gaatctgtga ccgaacagga ctccaaagac tccacctact ctctgtctag cacccctgact    540
ctgtccaaag cagactacga gaaacacaaa gtgtacgctt gcgaagttac ccatcagggt     600
ctgagctctc cggttaccaa atcctttaat agaggggagt gtggtggcgg tggcagtggt     660
ggtggaggtt ccggaggtgg cggttcagac atacaaatga cccagagtcc ttcatcggta     720
tccgcgtccg ttggcgatag ggtgactatt acatgtcaaa gctctcctag cgtctggagc     780
aattttctat cctggtatca acagaaaccg gggaaggctc caaaacttct gatttatgaa     840
gcctcgaaac tcaccagtgg agttccgtca agattcagtg gctctggatc agggacagac     900
ttcacgttga caatcagttc gctgcaacca gaggactttg cgacctacta ttgtggtgga     960
ggttacagta gcataagtga tacgacattt gggtgcggta ctaaggtgga aatcaaacgt    1020
acctaa                                                              1026

<210> SEQ ID NO 25
<211> LENGTH: 1131
<212> TYPE: DNA
<213> ORGANISM: Artificial
<220> FEATURE:
<223> OTHER INFORMATION: Heavy chain A26-645(gH5) including B72.3 leader
      sequence

<400> SEQUENCE: 25
atggaatggt cctgggtctt cctgtttttc ctttctgtca caaccggggt gcacagcgag      60
gtgcagctcg tcgagtctgg aggcgggctt gtccagcctg agggagcct gcgtctctct      120
tgtgcagcaa gcggtttcac gttcaccaac tacggtatcc actggattcg tcaggcacca     180
ggtaaaggtc tggaatgggt agcctctatc tctccgtctg gtggtctgac gtactaccgt     240
gactctgtca aggtcgtttt caccatctct cgtgatgacg cgaaaaactc tccgtacctg     300
cagatgaact ctctgcgtgc agaagatacc gcagtgtact actgcgctac tggtggtgaa     360
ggtatcttcg actactgggg tcagggtacc ctggtaactg tctcaagcgc ttctacaaag     420
ggcccatcgg tcttccccct ggcacccctc tccaagagca cctctggggg cacagcggcc     480
ctgggctgcc tggtcaagga ctacttcccc gaaccggtga cggtgtcgtg gaactcaggc     540
gccctgacca gcggcgtgca caccttcccg gctgtcctac agtcctctgg actctactcc     600
ctcagcagcg tggtgaccgt gccctccagc agcttgggca cccagaccta catctgcaac     660
gtgaatcaca agcccagcaa caccaaggtg gacaagaaag ttgagcccaa atcttgttcc     720
```

| | |
|---|---|
| ggaggtggcg gttccggagg tgccggtacc ggtggcggtg gatccgaagt ccagctgctt | 780 |
| gaatccggag gcggactcgt gcagcccgga ggcagtcttc gcttgtcctg cgctgtatct | 840 |
| ggaatcgacc tgagcaatta cgccatcaac tgggtgagac aggcacctgg gaaatgcctc | 900 |
| gaatggatcg gcattatatg ggctagtggg acgacctttt atgctacatg ggcgaagggt | 960 |
| agattcacaa tctcacggga taatagtaag aacacagtgt acctgcagat gaactccctg | 1020 |
| cgagcagagg ataccgccgt ttactattgt gctcgcactg tcccaggtta tagcactgca | 1080 |
| ccctactttg atctgtgggg gcagggcact ctggtcaccg tctcgagttg a | 1131 |

<210> SEQ ID NO 26
<211> LENGTH: 1074
<212> TYPE: DNA
<213> ORGANISM: Artificial
<220> FEATURE:
<223> OTHER INFORMATION: Heavy chain A26-645(gH5)

<400> SEQUENCE: 26

| | |
|---|---|
| gaggtgcagc tcgtcgagtc tggaggcggg cttgtccagc ctggagggag cctgcgtctc | 60 |
| tcttgtgcag caagcggttt cacgttcacc aactacggta tccactggat cgtcaggca | 120 |
| ccaggtaaag gtctggaatg ggtagcctct atctctccgt ctggtggtct gacgtactac | 180 |
| cgtgactctg tcaaaggtcg tttcaccatc tctcgtgatg acgcgaaaaa ctctccgtac | 240 |
| ctgcagatga actctctgcg tgcagaagat accgcagtgt actactgcgc tactggtggt | 300 |
| gaaggtatct cgactactg gggtcagggt accctggtaa ctgtctcaag cgcttctaca | 360 |
| aagggcccat cggtcttccc cctggcaccc tcctccaaga gcacctctgg gggcacagcg | 420 |
| gccctgggct gcctggtcaa ggactacttc cccgaaccgg tgacggtgtc gtggaactca | 480 |
| ggcgccctga ccagcggcgt gcacaccttc ccggctgtcc tacagtcctc tggactctac | 540 |
| tccctcagca gcgtggtgac cgtgccctcc agcagcttgg gcacccagac ctacatctgc | 600 |
| aacgtgaatc acaagcccag caacaccaag gtggacaaga agttgagcc caaatcttgt | 660 |
| tccggaggtg gcggttccgg aggtggcggt accggtggcg gtggatccga agtccagctg | 720 |
| cttgaatccg gaggcggact cgtgcagccc ggaggcagtc ttcgcttgtc ctgcgctgta | 780 |
| tctggaatcg acctgagcaa ttacgccatc aactgggtga caggcacc tgggaaatgc | 840 |
| ctcgaatgga tcggcattat atgggctagt gggacgacct tttatgctac atggcgaag | 900 |
| ggtagattca caatctcacg ggataatagt aagaacacag tgtacctgca gatgaactcc | 960 |
| ctgcgagcag aggataccgc cgtttactat tgtgctcgca ctgtcccagg ttatagcact | 1020 |
| gcaccctact tgatctgtg ggggcagggc actctggtca ccgtctcgag ttga | 1074 |

<210> SEQ ID NO 27
<211> LENGTH: 1086
<212> TYPE: DNA
<213> ORGANISM: Artificial
<220> FEATURE:
<223> OTHER INFORMATION: Light chain A26-645(gL4) including B72.3 leader
    sequence

<400> SEQUENCE: 27

| | |
|---|---|
| atgtcagttc ccacacaggt gctgggcctg cttctgttgt ggctcaccga tgctaggtgt | 60 |
| gatatccaga tgacccagag tccaagcagt ctctccgcca gcgtaggcga tcgtgtgact | 120 |
| attacctgtc gtgcaacccca gagcattctac aacgctctgg cttggtatca gcagaaaccg | 180 |
| ggtaaagcgc caaaactcct gatctacaac gcgaacactc tgcataccgg tgttccgtct | 240 |

```
cgtttctctg cgtctggttc tggtacggac tctactctga ccatctcctc tctgcagccg      300
gaagatttcg cgacctacta ctgccagcag tactacgatt acccactgac gtttggtggt      360
ggtaccaaag ttgagatcaa acgtacggtg gctgcaccat ctgtcttcat cttccccca      420 tctgatgagc agttgaagtc tggcactgcc tctgttgtgt gcctgctgaa taacttctac      480
cctagagagg ccaaagtcca gtggaaggtg gataacgccc ttcaatccgg aaactcccag      540
gagagtgtca ctgagcagga ctcaaaggac tccacctata gccttagcag cacactgaca      600
ctgagcaagg ctgactacga aaacacaag gtctacgcct gcgaagtgac acatcaaggc      660
ctgagctcac ccgtgacaaa gagctttaac aggggagagt gtggtggagg tggctctggc      720
ggtggtggct ccggaggcgg aggaagcgac atccagatga cccagagccc ttcctctgta      780
agcgccagtg tcggagacag agtgactatt acctgccaaa gctccccttc agtctggtcc      840
aattttctat cctggtacca gcaaaagccc ggaaaggctc ctaaattgct gatctacgaa      900
gcaagcaaac tcaccagcgg cgtgcccagc aggttcagcg gcagtgggtc tggaactgac      960
tttaccctga caatctcctc actccagccc gaggacttcg ccacctatta ctgcggtgga     1020
ggttacagta gcataagtga tacgacattt ggatgcggca ctaaagtgga aatcaagcgt     1080
acctga                                                                1086

<210> SEQ ID NO 28
<211> LENGTH: 1026
<212> TYPE: DNA
<213> ORGANISM: Artificial
<220> FEATURE:
<223> OTHER INFORMATION: Light chain A26-645(gL4)

<400> SEQUENCE: 28
gatatccaga tgacccagag tccaagcagt ctctccgcca gcgtaggcga tcgtgtgact       60
attacctgtc gtgcaaccca gagcatctac aacgctctgg cttggtatca gcagaaaccg      120
ggtaaagcgc caaaactcct gatctacaac gcgaacactc tgcataccgg tgttccgtct      180
cgtttctctg cgtctggttc tggtacggac tctactctga ccatctcctc tctgcagccg      240
gaagatttcg cgacctacta ctgccagcag tactacgatt acccactgac gtttggtggt      300
ggtaccaaag ttgagatcaa acgtacggtg gctgcaccat ctgtcttcat cttccccca      360 tctgatgagc agttgaagtc tggcactgcc tctgttgtgt gcctgctgaa taacttctac      420
cctagagagg ccaaagtcca gtggaaggtg gataacgccc ttcaatccgg aaactcccag      480
gagagtgtca ctgagcagga ctcaaaggac tccacctata gccttagcag cacactgaca      540
ctgagcaagg ctgactacga aaacacaag gtctacgcct gcgaagtgac acatcaaggc      600
ctgagctcac ccgtgacaaa gagctttaac aggggagagt gtggtggagg tggctctggc      660
ggtggtggct ccggaggcgg aggaagcgac atccagatga cccagagccc ttcctctgta      720
agcgccagtg tcggagacag agtgactatt acctgccaaa gctccccttc agtctggtcc      780
aattttctat cctggtacca gcaaaagccc ggaaaggctc ctaaattgct gatctacgaa      840
gcaagcaaac tcaccagcgg cgtgcccagc aggttcagcg gcagtgggtc tggaactgac      900
tttaccctga caatctcctc actccagccc gaggacttcg ccacctatta ctgcggtgga      960
ggttacagta gcataagtga tacgacattt ggatgcggca ctaaagtgga aatcaagcgt     1020
acctga                                                                1026

<210> SEQ ID NO 29
<211> LENGTH: 121
```

```
<212> TYPE: PRT
<213> ORGANISM: Artificial
<220> FEATURE:
<223> OTHER INFORMATION: Heavy chain variable domain of anti-albumin
      antibody (no ds)

<400> SEQUENCE: 29

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 30
<211> LENGTH: 121
<212> TYPE: PRT
<213> ORGANISM: Artificial
<220> FEATURE:
<223> OTHER INFORMATION: Heavy chain variable domain of anti-albumin
      antibody (ds)

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser
        115                 120

<210> SEQ ID NO 31
<211> LENGTH: 112
<212> TYPE: PRT
<213> ORGANISM: Artificial
<220> FEATURE:
<223> OTHER INFORMATION: Light chain variable domain of anti-albumin
      antibody (no ds)

<400> SEQUENCE: 31

Asp Ile Gln Met Thr Gln Ser Pro Ser Ser Val Ser Ala Ser Val Gly
```

```
                    1               5                  10                  15
Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Gly Gly Thr Lys Val Glu Ile Lys Arg Thr
                100                 105                 110
```

<210> SEQ ID NO 32
<211> LENGTH: 112
<212> TYPE: PRT
<213> ORGANISM: Artificial
<220> FEATURE:
<223> OTHER INFORMATION: Light chain variable domain of anti-albumin antibody (ds)

<400> SEQUENCE: 32

```
Asp Ile Gln Met Thr Gln Ser Pro Ser Ser Val Ser Ala Ser Val Gly
1               5                   10                  15

Asp Arg Val Thr Ile Thr Cys Gln Ser Ser Pro Ser Val Trp Ser Asn
                20                  25                  30

Phe Leu Ser Trp Tyr Gln Gln Lys Pro Gly Lys Ala Pro Lys Leu Leu
            35                  40                  45

Ile Tyr Glu Ala Ser Lys Leu Thr Ser Gly Val Pro Ser Arg Phe Ser
        50                  55                  60

Gly Ser Gly Ser Gly Thr Asp Phe Thr Leu Thr Ile Ser Ser Leu Gln
65                  70                  75                  80

Pro Glu Asp Phe Ala Thr Tyr Tyr Cys Gly Gly Tyr Ser Ser Ile
                85                  90                  95

Ser Asp Thr Thr Phe Gly Cys Gly Thr Lys Val Glu Ile Lys Arg Thr
                100                 105                 110
```

<210> SEQ ID NO 33
<211> LENGTH: 16
<212> TYPE: PRT
<213> ORGANISM: Artificial
<220> FEATURE:
<223> OTHER INFORMATION: Linker 1

<400> SEQUENCE: 33

```
Ser Gly Gly Gly Gly Ser Gly Gly Gly Gly Thr Gly Gly Gly Ser
1               5                   10                  15
```

<210> SEQ ID NO 34
<211> LENGTH: 15
<212> TYPE: PRT
<213> ORGANISM: Artificial
<220> FEATURE:
<223> OTHER INFORMATION: Linker 2

<400> SEQUENCE: 34

```
Gly Gly Gly Gly Ser Gly Gly Gly Gly Ser Gly Gly Gly Gly Ser
1               5                   10                  15
```

<210> SEQ ID NO 35
<211> LENGTH: 789
<212> TYPE: DNA
<213> ORGANISM: Artificial
<220> FEATURE:
<223> OTHER INFORMATION: 645 gH5gL4

<400> SEQUENCE: 35

```
gaggttcagc tgctggagtc tggaggcggg cttgtccagc ctggagggag cctgcgtctc      60
tcttgtgcag taagcggcat cgacctgtcc aactacgcga ttaactgggt acgtcaggca     120
ccgggtaaag gtctggaatg gatcggcatc atctgggcct ctggtacgac cttctacgct     180
acttgggcca aggtcgtttt caccatctcc cgtgacaact ctaaaaacac cgtgtacctg     240
cagatgaact ctctgcgtgc ggaagacact gcggtttact attgcgcgcg taccgttccg     300
ggctattcta ctgcaccgta cttcgacctg tggggtcagg gtactctggt taccgtctcg     360
agtggaggtg gcggttctgg cggtggcggt tccggtggcg gtggatcggg aggtggcggt     420
tctgatatcc agatgaccca gagtccaagc agtgtttccg ccagcgtagg cgatcgtgtg     480
actattacct gtcagtcctc tccgagcgtt tggtccaact tcctgagctg gtaccagcag     540
aaaccgggta agcccccgaa actgctgatc tacgaggcgt ctaaactgac ctctggtgta     600
ccgtcccgtt tctctggctc tggctctggt acggacttca ctctgaccat ctcctctctg     660
cagccggaag actttgcaac gtactactgc ggtggtggtt actcttccat ctctgacacc     720
acgttcggtg gaggcaccaa agttgaaatc aaacgtacgc atcaccatca ccatcaccat     780
caccatcac                                                             789
```

<210> SEQ ID NO 36
<211> LENGTH: 263
<212> TYPE: PRT
<213> ORGANISM: Artificial
<220> FEATURE:
<223> OTHER INFORMATION: 645 gH5gL4

<400> SEQUENCE: 36

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Gly Leu Glu Trp Ile
        35                  40                  45

Gly Ile Ile Trp Ala Ser Gly Thr Thr Phe Tyr Ala Thr Trp Ala Lys
    50                  55                  60

Gly Arg Phe Thr Ile Ser Arg Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Ser Gly Gly Gly Ser Gly Gly
        115                 120                 125

Gly Gly Ser Gly Gly Gly Ser Gly Gly Gly Ser Asp Ile Gln
    130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175
```

```
Trp Tyr Gln Gln Lys Pro Gly Lys Ala Pro Lys Leu Leu Ile Tyr Glu
            180                 185                 190

Ala Ser Lys Leu Thr Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
        210                 215                 220

Phe Ala Thr Tyr Tyr Cys Gly Gly Tyr Ser Ser Ile Ser Asp Thr
225                 230                 235                 240

Thr Phe Gly Gly Gly Thr Lys Val Glu Ile Lys Arg Thr His His His
                245                 250                 255

His His His His His His His
        260
```

<210> SEQ ID NO 37
<211> LENGTH: 789
<212> TYPE: DNA
<213> ORGANISM: Artificial
<220> FEATURE:
<223> OTHER INFORMATION: 645 gH5gL4ds

<400> SEQUENCE: 37

```
gaggttcagc tgctggagtc tggaggcggg cttgtccagc ctggagggag cctgcgtctc      60
tcttgtgcag taagcggcat cgacctgtcc aactacgcga ttaactgggt acgtcaggca     120
ccgggtaaat gcctggaatg gatcggcatc atctgggcct ctggtacgac cttctacgct     180
acttgggcca aggtcgtttt caccatctcc cgtgacaact ctaaaaacac cgtgtacctg     240
cagatgaact ctctgcgtgc ggaagacact gcggtttact attgcgcgcg taccgttccg     300
ggctattcta ctgcaccgta cttcgacctg tgggtcagg gtactctggt taccgtctcg     360
agtggaggtg gcggttctgg cggtggcggt tccggtggcg gtggatcggg aggtggcggt     420
tctgatatcc agatgaccca gagtccaagc agtgtttccg ccagcgtagg cgatcgtgtg     480
actattacct gtcagtcctc tccgagcgtt tggtccaact tcctgagctg gtaccagcag     540
aaaccgggta agcccccgaa actgctgatc tacgaggcgt ctaaactgac ctctggtgta     600
ccgtcccgtt tctctggctc tggctctggt acggacttca ctctgaccat ctcctctctg     660
cagccggaag actttgcaac gtactactgc ggtggtggtt actcttccat ctctgacacc     720
acgttcggtt gtggcaccaa agttgaaatc aaacgtacgc atcaccatca ccatcaccat     780
caccatcac                                                            789
```

<210> SEQ ID NO 38
<211> LENGTH: 263
<212> TYPE: PRT
<213> ORGANISM: Artificial
<220> FEATURE:
<223> OTHER INFORMATION: 645 gH5gL4ds

<400> SEQUENCE: 38

```
Glu Val Gln Leu Leu Glu Ser Gly Gly Gly Leu Val Gln Pro Gly Gly
1               5                   10                  15

Ser Leu Arg Leu Ser Cys Ala Val Ser Gly Ile Asp Leu Ser Asn Tyr
            20                  25                  30

Ala Ile Asn Trp Val Arg Gln Ala Pro Gly Lys Cys Leu Glu Trp Ile
        35                  40                  45

Gly Ile Ile Trp Ala Ser Gly Thr Thr Phe Tyr Ala Thr Trp Ala Lys
    50                  55                  60
```

```
Gly Arg Phe Thr Ile Ser Arg Asp Asn Ser Lys Asn Thr Val Tyr Leu
 65                  70                  75                  80

Gln Met Asn Ser Leu Arg Ala Glu Asp Thr Ala Val Tyr Tyr Cys Ala
             85                  90                  95

Arg Thr Val Pro Gly Tyr Ser Thr Ala Pro Tyr Phe Asp Leu Trp Gly
            100                 105                 110

Gln Gly Thr Leu Val Thr Val Ser Gly Gly Gly Ser Gly Gly
        115                 120                 125

Gly Gly Ser Gly Gly Gly Ser Gly Gly Gly Ser Asp Ile Gln
        130                 135                 140

Met Thr Gln Ser Pro Ser Ser Val Ser Ala Ser Val Gly Asp Arg Val
145                 150                 155                 160

Thr Ile Thr Cys Gln Ser Ser Pro Ser Val Trp Ser Asn Phe Leu Ser
                165                 170                 175

Trp Tyr Gln Gln Lys Pro Gly Lys Ala Pro Lys Leu Leu Ile Tyr Glu
                180                 185                 190

Ala Ser Lys Leu Thr Ser Gly Val Pro Ser Arg Phe Ser Gly Ser Gly
            195                 200                 205

Ser Gly Thr Asp Phe Thr Leu Thr Ile Ser Ser Leu Gln Pro Glu Asp
        210                 215                 220

Phe Ala Thr Tyr Tyr Cys Gly Gly Gly Tyr Ser Ser Ile Ser Asp Thr
225                 230                 235                 240

Thr Phe Gly Cys Gly Thr Lys Val Glu Ile Lys Arg Thr His His His
                245                 250                 255

His His His His His His His
            260

<210> SEQ ID NO 39
<211> LENGTH: 8
<212> TYPE: PRT
<213> ORGANISM: Artificial
<220> FEATURE:
<223> OTHER INFORMATION: Hinge Linker

<400> SEQUENCE: 39

Asp Lys Thr His Thr Cys Ala Ala
1               5

<210> SEQ ID NO 40
<211> LENGTH: 11
<212> TYPE: PRT
<213> ORGANISM: Artificial
<220> FEATURE:
<223> OTHER INFORMATION: Hinge Linker

<400> SEQUENCE: 40

Asp Lys Thr His Thr Cys Pro Pro Cys Pro Ala
1               5                   10

<210> SEQ ID NO 41
<211> LENGTH: 18
<212> TYPE: PRT
<213> ORGANISM: Artificial
<220> FEATURE:
<223> OTHER INFORMATION: Hinge Linker

<400> SEQUENCE: 41

Asp Lys Thr His Thr Cys Pro Pro Cys Pro Ala Thr Cys Pro Pro Cys
1               5                   10                  15

Pro Ala
```

<210> SEQ ID NO 42
<211> LENGTH: 25
<212> TYPE: PRT
<213> ORGANISM: Artificial
<220> FEATURE:
<223> OTHER INFORMATION: Hinge Linker

<400> SEQUENCE: 42

Asp Lys Thr His Thr Cys Pro Pro Cys Pro Ala Thr Cys Pro Pro Cys
1               5                   10                  15

Pro Ala Thr Cys Pro Pro Cys Pro Ala
            20                  25

<210> SEQ ID NO 43
<211> LENGTH: 30
<212> TYPE: PRT
<213> ORGANISM: Artificial
<220> FEATURE:
<223> OTHER INFORMATION: Hinge Linker

<400> SEQUENCE: 43

Asp Lys Thr His Thr Cys Pro Pro Cys Pro Ala Gly Lys Pro Thr Leu
1               5                   10                  15

Tyr Asn Ser Leu Val Met Ser Asp Thr Ala Gly Thr Cys Tyr
            20                  25                  30

<210> SEQ ID NO 44
<211> LENGTH: 31
<212> TYPE: PRT
<213> ORGANISM: Artificial
<220> FEATURE:
<223> OTHER INFORMATION: Hinge Linker

<400> SEQUENCE: 44

Asp Lys Thr His Thr Cys Pro Pro Cys Pro Ala Gly Lys Pro Thr His
1               5                   10                  15

Val Asn Val Ser Val Val Met Ala Glu Val Asp Gly Thr Cys Tyr
            20                  25                  30

<210> SEQ ID NO 45
<211> LENGTH: 15
<212> TYPE: PRT
<213> ORGANISM: Artificial
<220> FEATURE:
<223> OTHER INFORMATION: Hinge Linker

<400> SEQUENCE: 45

Asp Lys Thr His Thr Cys Cys Val Glu Cys Pro Pro Cys Pro Ala
1               5                   10                  15

<210> SEQ ID NO 46
<211> LENGTH: 26
<212> TYPE: PRT
<213> ORGANISM: Artificial
<220> FEATURE:
<223> OTHER INFORMATION: Hinge Linker

<400> SEQUENCE: 46

Asp Lys Thr His Thr Cys Pro Arg Cys Pro Glu Pro Lys Ser Cys Asp
1               5                   10                  15

Thr Pro Pro Pro Cys Pro Arg Cys Pro Ala
            20                  25

```
<210> SEQ ID NO 47
<211> LENGTH: 11
<212> TYPE: PRT
<213> ORGANISM: Artificial
<220> FEATURE:
<223> OTHER INFORMATION: Hinge Linker

<400> SEQUENCE: 47

Asp Lys Thr His Thr Cys Pro Ser Cys Pro Ala
1               5                   10

<210> SEQ ID NO 48
<211> LENGTH: 7
<212> TYPE: PRT
<213> ORGANISM: Artificial
<220> FEATURE:
<223> OTHER INFORMATION: Linker

<400> SEQUENCE: 48

Ser Gly Gly Gly Gly Ser Glu
1               5

<210> SEQ ID NO 49
<211> LENGTH: 6
<212> TYPE: PRT
<213> ORGANISM: Artificial
<220> FEATURE:
<223> OTHER INFORMATION: Linker

<400> SEQUENCE: 49

Asp Lys Thr His Thr Ser
1               5

<210> SEQ ID NO 50
<211> LENGTH: 6
<212> TYPE: PRT
<213> ORGANISM: Artificial
<220> FEATURE:
<223> OTHER INFORMATION: Linker

<400> SEQUENCE: 50

Ser Gly Gly Gly Gly Ser
1               5

<210> SEQ ID NO 51
<211> LENGTH: 11
<212> TYPE: PRT
<213> ORGANISM: Artificial
<220> FEATURE:
<223> OTHER INFORMATION: Linker

<400> SEQUENCE: 51

Ser Gly Gly Gly Gly Ser Gly Gly Gly Gly Ser
1               5                   10

<210> SEQ ID NO 52
<211> LENGTH: 16
<212> TYPE: PRT
<213> ORGANISM: Artificial
<220> FEATURE:
<223> OTHER INFORMATION: Linker

<400> SEQUENCE: 52

Ser Gly Gly Gly Gly Ser Gly Gly Gly Ser Gly Gly Gly Gly Ser
1               5                   10                  15

<210> SEQ ID NO 53
```

```
<211> LENGTH: 21
<212> TYPE: PRT
<213> ORGANISM: Artificial
<220> FEATURE:
<223> OTHER INFORMATION: Linker

<400> SEQUENCE: 53

Ser Gly Gly Gly Gly Ser Gly Gly Gly Gly Ser Gly Gly Gly Gly Ser
1               5                   10                  15

Gly Gly Gly Gly Ser
            20

<210> SEQ ID NO 54
<211> LENGTH: 26
<212> TYPE: PRT
<213> ORGANISM: Artificial
<220> FEATURE:
<223> OTHER INFORMATION: Linker

<400> SEQUENCE: 54

Ser Gly Gly Gly Gly Ser Gly Gly Gly Gly Ser Gly Gly Gly Gly Ser
1               5                   10                  15

Gly Gly Gly Gly Ser Gly Gly Gly Gly Ser
            20                  25

<210> SEQ ID NO 55
<211> LENGTH: 11
<212> TYPE: PRT
<213> ORGANISM: Artificial
<220> FEATURE:
<223> OTHER INFORMATION: Linker

<400> SEQUENCE: 55

Ala Ala Ala Gly Ser Gly Gly Ala Ser Ala Ser
1               5                   10

<210> SEQ ID NO 56
<211> LENGTH: 16
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 56

Ala Ala Ala Gly Ser Gly Xaa Gly Gly Gly Ser Gly Ala Ser Ala Ser
1               5                   10                  15

<210> SEQ ID NO 57
<211> LENGTH: 21
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid

<400> SEQUENCE: 57

Ala Ala Ala Gly Ser Gly Xaa Gly Gly Gly Ser Xaa Gly Gly Gly Ser
```

Gly Ala Ser Ala Ser
            20

<210> SEQ ID NO 58
<211> LENGTH: 26
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 58

Ala Ala Ala Gly Ser Gly Xaa Gly Gly Gly Ser Xaa Gly Gly Gly Ser
1               5                   10                  15

Xaa Gly Gly Gly Ser Gly Ala Ser Ala Ser
            20                  25

<210> SEQ ID NO 59
<211> LENGTH: 31
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid
<220> FEATURE:
<221> NAME/KEY: misc_feature
<222> LOCATION: (12)..(12)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid
<220> FEATURE:
<221> NAME/KEY: misc_feature
<222> LOCATION: (22)..(22)
<223> OTHER INFORMATION: Xaa can be any naturally occurring amino acid

<400> SEQUENCE: 59

Ala Ala Ala Gly Ser Gly Xaa Gly Gly Gly Ser Xaa Gly Gly Gly Ser
1               5                   10                  15

Xaa Gly Gly Gly Ser Xaa Gly Gly Gly Ser Gly Ala Ser Ala Ser
            20                  25                  30

<210> SEQ ID NO 60
<211> LENGTH: 13
<212> TYPE: PRT
<213> ORGANISM: Artificial
<220> FEATURE:
<223> OTHER INFORMATION: Linker
<220> FEATURE:
<221> NAME/KEY: misc_feature
<222> LOCATION: (7)..(7)
<223> OTHER INFORMATION: Xaa can be any naturally occurring amino acid

<400> SEQUENCE: 60

```
Ala Ala Ala Gly Ser Gly Xaa Ser Gly Ala Ser Ala Ser
1               5                   10
```

<210> SEQ ID NO 61
<211> LENGTH: 28
<212> TYPE: PRT
<213> ORGANISM: Artificial
<220> FEATURE:
<223> OTHER INFORMATION: Linker

<400> SEQUENCE: 61

```
Pro Gly Gly Asn Arg Gly Thr Thr Thr Arg Arg Pro Ala Thr Thr
1               5                   10                  15

Thr Gly Ser Ser Pro Gly Pro Thr Gln Ser His Tyr
            20                  25
```

<210> SEQ ID NO 62
<211> LENGTH: 11
<212> TYPE: PRT
<213> ORGANISM: Artificial
<220> FEATURE:
<223> OTHER INFORMATION: Linker

<400> SEQUENCE: 62

```
Ala Thr Thr Thr Gly Ser Ser Pro Gly Pro Thr
1               5                   10
```

<210> SEQ ID NO 63
<211> LENGTH: 6
<212> TYPE: PRT
<213> ORGANISM: Artificial
<220> FEATURE:
<223> OTHER INFORMATION: Linker

<400> SEQUENCE: 63

```
Ala Thr Thr Thr Gly Ser
1               5
```

<210> SEQ ID NO 64
<211> LENGTH: 21
<212> TYPE: PRT
<213> ORGANISM: Artificial
<220> FEATURE:
<223> OTHER INFORMATION: Linker

<400> SEQUENCE: 64

```
Glu Pro Ser Gly Pro Ile Ser Thr Ile Asn Ser Pro Pro Ser Lys Glu
1               5                   10                  15

Ser His Lys Ser Pro
            20
```

<210> SEQ ID NO 65
<211> LENGTH: 15
<212> TYPE: PRT
<213> ORGANISM: Artificial
<220> FEATURE:
<223> OTHER INFORMATION: Linker

<400> SEQUENCE: 65

```
Gly Thr Val Ala Ala Pro Ser Val Phe Ile Phe Pro Pro Ser Asp
1               5                   10                  15
```

<210> SEQ ID NO 66
<211> LENGTH: 15
<212> TYPE: PRT
<213> ORGANISM: Artificial

```
<220> FEATURE:
<223> OTHER INFORMATION: Linker

<400> SEQUENCE: 66

Gly Gly Gly Gly Ile Ala Pro Ser Met Val Gly Gly Gly Gly Ser
1               5                   10                  15

<210> SEQ ID NO 67
<211> LENGTH: 15
<212> TYPE: PRT
<213> ORGANISM: Artificial
<220> FEATURE:
<223> OTHER INFORMATION: Linker

<400> SEQUENCE: 67

Gly Gly Gly Gly Lys Val Glu Gly Ala Gly Gly Gly Gly Ser
1               5                   10                  15

<210> SEQ ID NO 68
<211> LENGTH: 15
<212> TYPE: PRT
<213> ORGANISM: Artificial
<220> FEATURE:
<223> OTHER INFORMATION: Linker

<400> SEQUENCE: 68

Gly Gly Gly Gly Ser Met Lys Ser His Asp Gly Gly Gly Gly Ser
1               5                   10                  15

<210> SEQ ID NO 69
<211> LENGTH: 15
<212> TYPE: PRT
<213> ORGANISM: Artificial
<220> FEATURE:
<223> OTHER INFORMATION: Linker

<400> SEQUENCE: 69

Gly Gly Gly Gly Asn Leu Ile Thr Ile Val Gly Gly Gly Gly Ser
1               5                   10                  15

<210> SEQ ID NO 70
<211> LENGTH: 15
<212> TYPE: PRT
<213> ORGANISM: Artificial
<220> FEATURE:
<223> OTHER INFORMATION: Linker

<400> SEQUENCE: 70

Gly Gly Gly Gly Val Val Pro Ser Leu Pro Gly Gly Gly Gly Ser
1               5                   10                  15

<210> SEQ ID NO 71
<211> LENGTH: 12
<212> TYPE: PRT
<213> ORGANISM: Artificial
<220> FEATURE:
<223> OTHER INFORMATION: Linker

<400> SEQUENCE: 71

Gly Gly Glu Lys Ser Ile Pro Gly Gly Gly Ser
1               5                   10

<210> SEQ ID NO 72
<211> LENGTH: 18
<212> TYPE: PRT
<213> ORGANISM: Artificial
<220> FEATURE:
```

```
<223> OTHER INFORMATION: Linker

<400> SEQUENCE: 72

Arg Pro Leu Ser Tyr Arg Pro Pro Phe Pro Phe Gly Phe Pro Ser Val
1               5                   10                  15

Arg Pro

<210> SEQ ID NO 73
<211> LENGTH: 18
<212> TYPE: PRT
<213> ORGANISM: Artificial
<220> FEATURE:
<223> OTHER INFORMATION: Linker

<400> SEQUENCE: 73

Tyr Pro Arg Ser Ile Tyr Ile Arg Arg His Pro Ser Pro Ser Leu
1               5                   10                  15

Thr Thr

<210> SEQ ID NO 74
<211> LENGTH: 18
<212> TYPE: PRT
<213> ORGANISM: Artificial
<220> FEATURE:
<223> OTHER INFORMATION: Linker

<400> SEQUENCE: 74

Thr Pro Ser His Leu Ser His Ile Leu Pro Ser Phe Gly Leu Pro Thr
1               5                   10                  15

Phe Asn

<210> SEQ ID NO 75
<211> LENGTH: 18
<212> TYPE: PRT
<213> ORGANISM: Artificial
<220> FEATURE:
<223> OTHER INFORMATION: Linker

<400> SEQUENCE: 75

Arg Pro Val Ser Pro Phe Thr Phe Pro Arg Leu Ser Asn Ser Trp Leu
1               5                   10                  15

Pro Ala

<210> SEQ ID NO 76
<211> LENGTH: 18
<212> TYPE: PRT
<213> ORGANISM: Artificial
<220> FEATURE:
<223> OTHER INFORMATION: Linker

<400> SEQUENCE: 76

Ser Pro Ala Ala His Phe Pro Arg Ser Ile Pro Arg Pro Gly Pro Ile
1               5                   10                  15

Arg Thr

<210> SEQ ID NO 77
<211> LENGTH: 18
<212> TYPE: PRT
<213> ORGANISM: Artificial
<220> FEATURE:
<223> OTHER INFORMATION: Linker

<400> SEQUENCE: 77
```

```
Ala Pro Gly Pro Ser Ala Pro Ser His Arg Ser Leu Pro Ser Arg Ala
1               5                   10                  15

Phe Gly
```

<210> SEQ ID NO 78
<211> LENGTH: 18
<212> TYPE: PRT
<213> ORGANISM: Artificial
<220> FEATURE:
<223> OTHER INFORMATION: Linker

<400> SEQUENCE: 78

```
Pro Arg Asn Ser Ile His Phe Leu His Pro Leu Leu Val Ala Pro Leu
1               5                   10                  15

Gly Ala
```

<210> SEQ ID NO 79
<211> LENGTH: 18
<212> TYPE: PRT
<213> ORGANISM: Artificial
<220> FEATURE:
<223> OTHER INFORMATION: Linker

<400> SEQUENCE: 79

```
Met Pro Ser Leu Ser Gly Val Leu Gln Val Arg Tyr Leu Ser Pro Pro
1               5                   10                  15

Asp Leu
```

<210> SEQ ID NO 80
<211> LENGTH: 18
<212> TYPE: PRT
<213> ORGANISM: Artificial
<220> FEATURE:
<223> OTHER INFORMATION: Linker

<400> SEQUENCE: 80

```
Ser Pro Gln Tyr Pro Ser Pro Leu Thr Leu Thr Leu Pro Pro His Pro
1               5                   10                  15

Ser Leu
```

<210> SEQ ID NO 81
<211> LENGTH: 18
<212> TYPE: PRT
<213> ORGANISM: Artificial
<220> FEATURE:
<223> OTHER INFORMATION: Linker

<400> SEQUENCE: 81

```
Asn Pro Ser Leu Asn Pro Pro Ser Tyr Leu His Arg Ala Pro Ser Arg
1               5                   10                  15

Ile Ser
```

<210> SEQ ID NO 82
<211> LENGTH: 17
<212> TYPE: PRT
<213> ORGANISM: Artificial
<220> FEATURE:
<223> OTHER INFORMATION: Linker

<400> SEQUENCE: 82

```
Leu Pro Trp Arg Thr Ser Leu Leu Pro Ser Leu Pro Leu Arg Arg Arg
1               5                   10                  15

Pro
```

<210> SEQ ID NO 83
<211> LENGTH: 18
<212> TYPE: PRT
<213> ORGANISM: Artificial
<220> FEATURE:
<223> OTHER INFORMATION: Linker

<400> SEQUENCE: 83

Pro Pro Leu Phe Ala Lys Gly Pro Val Gly Leu Leu Ser Arg Ser Phe
1               5                   10                  15

Pro Pro

<210> SEQ ID NO 84
<211> LENGTH: 18
<212> TYPE: PRT
<213> ORGANISM: Artificial
<220> FEATURE:
<223> OTHER INFORMATION: Linker

<400> SEQUENCE: 84

Val Pro Pro Ala Pro Val Val Ser Leu Arg Ser Ala His Ala Arg Pro
1               5                   10                  15

Pro Tyr

<210> SEQ ID NO 85
<211> LENGTH: 17
<212> TYPE: PRT
<213> ORGANISM: Artificial
<220> FEATURE:
<223> OTHER INFORMATION: Linker

<400> SEQUENCE: 85

Leu Arg Pro Thr Pro Pro Arg Val Arg Ser Tyr Thr Cys Cys Pro Thr
1               5                   10                  15

Pro

<210> SEQ ID NO 86
<211> LENGTH: 18
<212> TYPE: PRT
<213> ORGANISM: Artificial
<220> FEATURE:
<223> OTHER INFORMATION: Linker

<400> SEQUENCE: 86

Pro Asn Val Ala His Val Leu Pro Leu Leu Thr Val Pro Trp Asp Asn
1               5                   10                  15

Leu Arg

<210> SEQ ID NO 87
<211> LENGTH: 18
<212> TYPE: PRT
<213> ORGANISM: Artificial
<220> FEATURE:
<223> OTHER INFORMATION: Linker

<400> SEQUENCE: 87

Cys Asn Pro Leu Leu Pro Leu Cys Ala Arg Ser Pro Ala Val Arg Thr
1               5                   10                  15

Phe Pro

<210> SEQ ID NO 88
<211> LENGTH: 15

```
<212> TYPE: PRT
<213> ORGANISM: Artificial
<220> FEATURE:
<223> OTHER INFORMATION: Linker

<400> SEQUENCE: 88

Gly Gly Gly Gly Ser Gly Gly Gly Gly Thr Gly Gly Gly Gly Ser
1               5                   10                  15

<210> SEQ ID NO 89
<211> LENGTH: 11
<212> TYPE: PRT
<213> ORGANISM: Artificial
<220> FEATURE:
<223> OTHER INFORMATION: linker

<400> SEQUENCE: 89

Gly Ala Pro Ala Pro Ala Ala Pro Ala Pro Ala
1               5                   10

<210> SEQ ID NO 90
<211> LENGTH: 4
<212> TYPE: PRT
<213> ORGANISM: Artificial
<220> FEATURE:
<223> OTHER INFORMATION: linker

<400> SEQUENCE: 90

Pro Pro Pro Pro
1
```

METHOD FOR INCREASING THE PERCENTAGE OF MONOMERIC ANTIBODY FAB-DSFV MULTIMERIC SPECIES

CROSS-REFERENCE TO RELATED APPLICATION

This application is the U.S. national stage application of International Patent Application No. PCT/EP2016/059050, filed Apr. 22, 2016.

The Sequence Listing for this application is labeled "Seq-List.txt" which was created on Oct. 17, 2017 and is 62 KB. The entire content of the sequence listing is incorporated herein by reference in its entirety.

The present disclosure relates to a method for increasing the amount of monomer in a composition of recombinantly expressed antibody molecules and compositions obtained or obtainable from the method described herein.

Therapeutic monoclonal antibodies have become a very important class of therapeutic agents. As disclosed in WO2010/019493 purification and formulation of these antibody molecules represents a challenge. However, it is vitally important that only material of the highest quality is employed in therapeutic applications. This has become more difficult as novel and complicated antibody constructs are being generated as therapeutics, for example bispecific formats.

Novel antibody formats often require the presence of a least one Fv region comprising a variable light domain (VL) and variable heavy domain (VH) wherein the variable domains are not in their natural state of being joined at the C-terminus to the constant light domain (CL) or constant heavy domain (CH1). In a naturally occurring whole antibody molecule the presence of the CL and CH1 domains acts to stabilize the paring of the VL and VH. Accordingly, in the absence of the CL and CH1 domains the variable domains are prone to dynamic exchange with variable domains of adjacent molecules. One way to stop this dynamic process is by the introduction of a disulfide bond between the $V_H$ and $V_L$ which locks down the v-region pairing and prevents dynamic exchange. However, the presence of the disulfide bond can also act to stabilize unwanted multimers of the antibody.

Novel antibody formats also often comprise linkers. However, the presence of the linkers may result in the formation of unwanted multimers when the variable domain in one molecule pairs with a variable domain in another molecule thereby joining the two molecules together. The presence of a disulfide bond in the Fv then acts to stabilize the multimeric species.

An example of a known bispecific antibody format is the Fab-dsFv as described in detail in WO2010/035012 and WO2011/036460. This antibody format has the propensity to form multimers which comprise two or more monomers, as shown in FIG. 27. Similar multimeric species also occur in compositions comprising disulphide bonded scFv molecules wherein the VH from one scFv pairs with the VL from a separate scFv to form disulfide stabilized Fv pair which joins two scFv molecules together resulting in a dimer of two scFvs. Further pairings of variable domains in separate molecules can create larger multimeric species.

Known methods of purification, such as chromatography, are capable of separating large multimeric species from smaller monomeric species but this inevitably results in a lower overall yield of antibody. Accordingly, for bispecific antibody formats there is a great need for methods to address the problem of unwanted multimeric species in compositions of antibody.

The method of the present disclosure provides a solution to the above problem by reducing the amount of multimer in compositions comprising antibody molecules. The present disclosure is especially useful to provide compositions of monomeric monoclonal antibodies molecules suitable for human use.

Thus there is provided a method for increasing the percentage of monomer in a composition of recombinantly expressed antibody molecules characterised in that the antibody molecule comprises at least one Fv with specificity for an antigen of interest comprising one VH and one VL wherein said VH and VL are connected directly or indirectly via one or more linkers and are stabilised by a disulfide bond therebetween, said method comprises:

a) a thermal conversion step of holding the composition comprising the antibody molecule at a temperature in the range 30 to 60° C. for a period of at least 1 hour, b) wherein step a) is performed in the presence of a reducing agent or after treatment with a reducing agent.

Employing the process described herein to recombinantly expressed antibody advantageously increases the amount of monomer in the composition. Advantageously the method herein can be easily and cost-effectively employed on a commercial scale.

The method of the present invention is capable of converting multimeric species into monomers, thereby increasing the percentage of monomer. The conversion step advantageously allows the reducing agent to reduce the disulfide bond between the VH and VL and the multimeric species to partially denature and thereby disassembling the multimers. The method also allows the VH and VL domains to form Fv pairs within single antibody molecules and the reformation of the stabilizing disulfide bond between the VH and VL resulting in monomers. The inventors have surprisingly shown that the conversion step and the reducing agent can be used to convert antibody multimers to antibody monomers without fully denaturing the antibody. The method of the present invention also advantageously allows the correct disulfide bonds to be reformed to produce the desired monomers.

In one embodiment the increase in the concentration of monomer is 2, 3, 4 fold or more. The method of the present invention preferably provides a recombinant antibody composition following the thermal conversion step which comprises at least 50%, at least 60%, at least 70%, 75%, 80%, 85% or at least 90% antibody in monomeric form.

In one embodiment the present disclosure extends to an antibody or binding fragment obtained or obtainable from the method disclosed herein.

The invention also provides use of the composition obtained from the method disclosed herein for use in treatment.

BRIEF DESCRIPTION OF THE FIGURES

FIG. 1 shows non-reducing SDS-PAGE of protein-A purified antibody A26 Fab-645dsFv treated with 50 mM beta-mercaptanethanol at 50° C. i.e. where the treatment was performed after protein A purification.

FIG. 2 shows reducing SDS-PAGE of protein-A purified antibody A26 Fab-645dsFv treated with 50 mM beta-mercaptanethanol at 50° C. i.e. where the treatment was performed after protein A purification.

FIGS. 19 to 26 shows various antibody molecule sequences and components thereof.

FIG. 27 shows a monomeric Fab-dsFv and multimeric versions of Fab-dsFv.

FIG. 28 shows example antibody formats.

DETAILED DESCRIPTION

Figure 3:
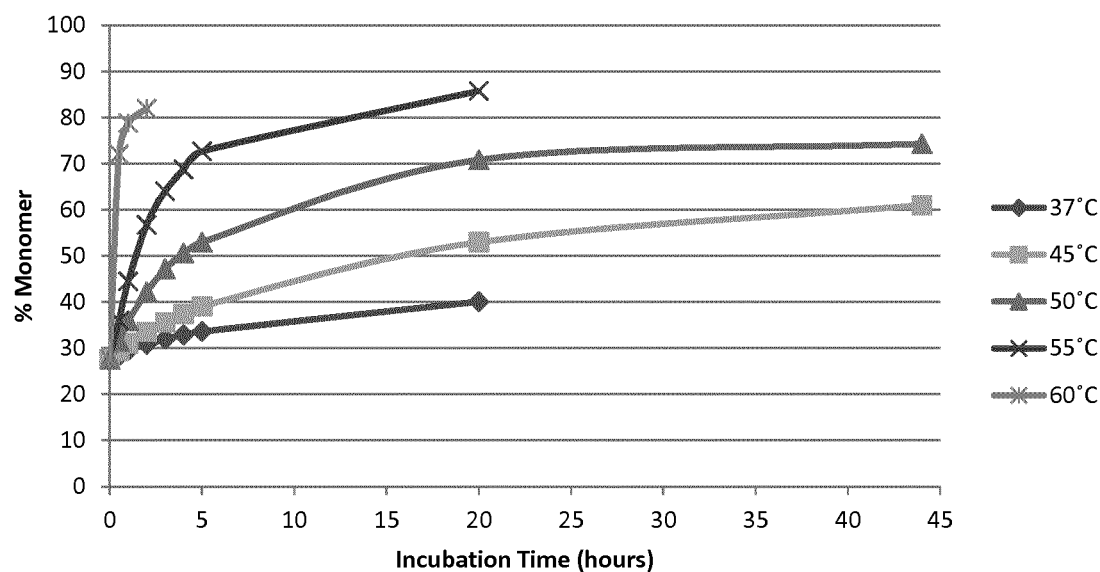
FIG. 3 shows SEC-HPLC analysis of percentage monomer obtained for antibody A26 Fab-645dsFv treated with 50 mM beta-mercaptanethanol at temperatures in the range 37 to 60° C.

The term multimers or multimeric form as used herein refers to antibody forms consisting of the domains from two or more antibody monomers in which all of the domains are correctly folded and paired. By way of example, multimers may be formed from two or more antibody monomers wherein each VH domain is paired with a VL domain to form a complementary Fv region, such as shown for a Fab-dsFv in FIG. 27.

In one embodiment increasing the percentage of monomer as employed herein refers to obtaining a numerical value of monomeric antibody molecule that is a higher percentage of the total target protein yield compared to the monomer antibody molecule percentage obtain before the process of the present disclosure was applied. For example the percentage monomer may be 30% of the initial yield of antibody molecules and after applying the present process the percentage monomer may be at least 50%, at least 60%, at least 70%, at least 75%, at least 80%, at least 85% or at least 90%. In one embodiment the absolute numerical value i.e. yield of isolated monomer is higher after performing the process of the present disclosure.

Yield or total protein as employed herein refers to the combined value of antibody molecule species in the composition, unless the context indicates otherwise. In one embodiment the value of the yield employed is the value before processing according to the present disclosure.

In one embodiment the value of the yield employed is the amount of total protein (antibody molecule species) recovered after performing the process according to the present disclosure.

The total protein (antibody molecule species) recovered after performing the process of the present disclosure will be reduced because inevitably processing results in some loses.

Target protein refers to the recombinant antibody molecule that is expressed.

Recombinant protein is protein, such as an antibody molecule expressed employing recombinant techniques.

Unless the context indicates otherwise antibody concentration as employed herein, also referred to as the feed concentration, refers to material comprising the target protein and multimers thereof the concentration of all antibody species including monomers and multimers. In one embodiment, the antibody concentration is the concentration of antibody in the composition following a step of Protein A purification to remove impurities from the composition.

In step a) of the method of the present invention the thermal conversion is carried out at a temperature in the range 30 to 60° C. In one embodiment the temperature is in the range, 35 to 60° C., 40 to 60° C., 45 to 55° C., 45 to 50° C., 50 to 55° C., 48 to 52° C., 49 to 51° C. such as 46° C., 47° C., 48° C., 49° C., 50° C., 50.5° C., 51° C., 51.5° C., 52° C., 52.5° C., 53° C., 53.5° C., 54° C., 54.5° C. and 55° C. In one embodiment the temperature in step a) is performed at 46, 47, 48, 49, 50, 51, 52, 53, 54 or 55° C., such as about 50° C.

A temperature in the range as employed herein does not necessarily mean the composition is held at the same temperature for the duration of the process, however the composition is generally held at one or more temperatures in the stated range, during the period over which the relevant step of the method is performed. If and when, the temperature drifts or shifts outside the range during treatment the controller will take steps to bring the composition within the desired range.

The period over which the antibody composition is held at a temperature in the range according to the present disclosure is in one embodiment in the range 1 to 70 hours, for example 2 to 60 hours, such as 3 to 50 hours, 3 to 10 hours, 4 to 6 hours, 4.5 to 5.5 hours in particular 4, 5, 6, 7, 8, 9, 10, 11, 12, 13, 14, 15, 16, 17, 18, 19, 20, 21, 22, 23, 24, 25 hours. In one embodiment the period is around 5 hours.

Reducing agent as employed herein refers to a reducing agent capable of reducing a disulfide bond in the molecule in question, such as the antibody. The reducing agent in the presence of an antibody comprising one or more disulfide bonds has the capacity, under appropriate conditions, to reduce the disulfide bond, for example to a form —SH. In one embodiment the reducing agent itself comprises a single thiol group, two thiol groups or three or more thiol groups. Alternatively, the reducing agent does not comprise a thiol group itself.

Thiol as employed herein refers to a group comprising the entity —SH.

In one embodiment the reducing agent is selected from the group comprising: glutathione (GSH), ethylene sulfite, 2-mercaptoethanol (BME), 2-mercaptoethylamine including salts thereof such as hydrochloride (also referred to as BMEA, bMEA or B-mea, β-mea or βmea), cysteine, such as cysteine-HCl, phosphorous acid and dithiothreitol (DTT), TCEP (tris(2-carboxyethyl)phosphine), THP (tris(hydroxypropyl)phosphine).

In one embodiment the reducing agent comprises a single thiol group. Advantageously if a reducing agent comprising a single thiol is employed the desired disulfide bond between the variable regions of monomers forms naturally i.e. with the need to perform a specific oxidation step. Examples of reducing agents comprising a single thiol group include, but are not limited to, glutathione, mercaptoethanol (such as 2-mercaptoethanol), mercaptoethylamine (such as 2-mercaptoethylamine) and cysteine (such as cysteine-HCl).

In one embodiment the thiol reducing agent is mercaptoethanol (such as 2-mercaptoethanol), mercaptoethylamine (such as 2-mercaptoethylamine), and in particular 2-mercaptoethylamine (also referred to as BMEA, bMEA or B-mea, β-mea or βmea).

In one embodiment the reducing agent is added before the antibody composition is in the temperature range of the present disclosure. In one embodiment the step a) is performed after treatment with a reducing agent, in particular wherein the reducing agent is removed prior to heating. The stronger the reducing agent the more likely it is to be suited for use in a pre-treatment step and removed prior to step a). Accordingly, in one embodiment wherein the reducing agent is selected from phosphorous acid, DDT, TCEP and THP, the reducing agent is removed prior to step a). If required the reducing agent may be removed prior to heating by routine techniques including diafiltration and the like. Use of TCEP may require an oxidation step to reintroduce the desired disulfide bonds in the final antibody molecules.

In one embodiment the reducing agent is not removed before the temperature is brought into the range, 30 to 60° C. The embodiment wherein the reducing agent remains in the composition during heating in step a) is particularly of benefit for reducing agents which contain a single thiol group such as the reducing agents selected from glutathione, mercaptoethanol (such as 2-mercaptoethanol), mercaptoethylamine (such as 2-mercaptoethylamine) and cysteine (such as cysteine-HCl).

If the reducing agent is DTT or phosphorous acid which are intermediate in strength and are retained for the thermal conversion step a), then temperatures at the lower end of the range, for example in the range 30 to 45° C. may be employed. Further, use of these reagents in combination with temperature in some molecules may require an oxidation step to reform some or all of the desired disulfide bonds in the antibody monomer molecules.

In one embodiment the reducing agent is added after the antibody composition is in the temperature range of the present disclosure. In one embodiment the reducing agent is added as the antibody composition is entering the temperature range of the present disclosure. In one embodiment the reducing agent is added after the antibody composition is in the temperature range of the present disclosure. In one embodiment the reducing agent is added on more than one occasion, for example before the temperature is in the desired range and/or after the composition is in the stated temperature range. In one embodiment the reducing agent is added two or more times during the process.

In the above embodiments, wherein the reducing agent is added prior to heating in step a) and remains in the composition during heating in step a) or is added as the antibody composition is entering the temperature range or after the antibody composition is in the temperature range of the present disclosure, the reducing agent may be removed during or after the heating step by routine techniques including diafiltration and the like.

In one embodiment, the method comprises a further step of subjecting the composition to oxidizing conditions after step a) in order to reform the one or more disulfide bonds in the antibody. This embodiment may be of benefit if a reducing agent such as phosphorous acid, DDT, TCEP or THP is used. Alternatively, the method does not comprise a step of subjecting the composition to oxidising conditions after step a). An oxidising step is not required particularly when a reducing agent comprising a single thiol group such as glutathione, mercaptoethanol (such as 2-mercaptoethanol), mercaptoethylamine (such as 2-mercaptoethylamine) and cysteine (such as cysteine-HCl) is used.

A further benefit the method according to the present disclosure is that the antibody molecule is not completely unfolded by the conditions employed. That is to say deactivation resulting from unfolding is minimised and the need to refold the antibody is avoided. In one embodiment wherein the antibody comprises multiple disulfide bonds not all disulfide bonds in the antibody are reduced. Thus in molecules such as so-called Fab-dsFv intra-chain disulfide bonds in the Fab fragment and the Fv of the antibody molecule are not reduced by the method of the present invention. β-mea is particularly advantageous for Fab-dsFv molecules.

Concentrations of the reducing agents are generally in the range 1 mM to 100 mM, for example 10 to 90 mM, such as 30 to 90 mM, 60 to 90 mM, 70 to 90 mM, 70 to 80 mM, 80 to 90 mM, 30 to 50 mM or 20 to 50 mM. In one embodiment the concentration of the reducing agent is selected from 15 mM, 20 mM, 25 mM, 30 mM 35 mM, 40 mM, 45 mM, 50 mM, 55 mM, 60 mM, 65 mM, 70 mM, 75 mM, 80 mM, 83 mM, 85 mM, 90 mM and 100 mM.

In one embodiment the reducing agent is employed in the presence of an amino acid, for example a hydrophobic amino acid, a polar amino acid or a charged amino acid. Without wishing to be bound by theory, it is thought that the presence of the amino acid acts to stabilize the molecule structure of the recombinant antibody molecule during the thermal conversion step and thereby protects against thermal denaturation, thus improving overall yield. In one embodiment the amino acid is selected from arginine, lysine, alanine, proline, serine and glycine. In one embodiment the concentration of amino acid is in the range 0.01 to 1.0M, for example 0.01 to 0.8M, 0.2 to 0.8M or 0.7 to 0.8M. In one embodiment the concentration of amino acid is selected from 0.02, 0.05, 0.1, 0.2, 0.3, 0.4, 0.5, 0.6, 0.7, 0.8 or 0.9 M.

In one embodiment the amino acid is proline, alanine or lysine. In one embodiment the concentration of proline, alanine or lysine employed is in the range 10 mM to 800 mM, for example 20, 55, 110, 280, 555 or 777 mM.

The amino acid may be added to the recombinant antibody composition before or after the temperature is in the relevant range for example 30 to 60° C., in particular a range or specific temperature described herein. In one embodiment, the amino acid is added to the composition before the temperature is raised to the range of 30 to 60° C.

In one embodiment a basic salt is added, for example a citrate salt, a sulfate salt or carbonate salt, such as citrate salt or sulfate salt.

In one embodiment the period of maintaining the temperature in the desired range is about 1 to 70 hours, for example 2 to 60 hours, such as 3 to 50 hours, 3 to 10 hours, 4 to 6 hours, in particular 4, 5, 6, 7, 8, 9, 10, 11, 12, 13, 14, 15, 16, 17, 18, 19, 20, 21, 22, 23, 24 or 25 hours. In one embodiment the thermal step is performed in the presence of concomitant stirring, for example where the stirring in the range 100 to 1200 rpm, such as 100, 200, 300, 400, 500, 600, 700, 800, 900, 1000, 1100 or 1200 rpm.

In one embodiment the concentration of the antibody in the composition is in the range 1.5 g/L to 5 g/L, for example 2 g/L to 4 g/L such as 2 g/L to 3 g/L.

In one embodiment the method does not employ an amino acid and employs an antibody molecule concentration in the range 1.5 g/L to 5 g/L, is performed at temperature about 50° C. in the presence of 50 to 90 mM of a reducing agent such as BMEA or BME, in particular BMEA, for a period of about 5 hours. Advantageously yield may be as high as 90% wherein 60% or more thereof is monomer.

In one embodiment of the method of the present invention the following reaction conditions are employed: the reducing agent is BMEA, the amino acid is lysine, the temperature is 50° C. and the period is about 5 hours.

In one embodiment the thermal conversion step is performed at temperature in the range 45 to 55° C., such as 50° C., in the presence of 50 to 90 mM, such as 50 mM or 75 mM, of a reducing agent such as BMEA or BME, in particular BMEA for a period of 4 to 6 hours, such as 5 hours. In this embodiment the antibody concentration is preferably in the range 2 to 3 g/L. In one embodiment, step a) is performed at a temperature of 50° C., for a period of 5 hours and in step b) the reducing agent is BMEA or BME and is at a concentration 70 to 80 mM, for example 75 mM. In this embodiment, the thermal conversion step is preferably carried out in the presence of an amino acid selected from proline, alanine or lysine at a concentration in the range of 0.01 to 0.8M, such as 0.7 to 0.8M.

In a further embodiment of the method of the present disclosure the following reaction conditions are employed in the thermal conversion step: the reducing agent is BMEA at a concentration of 75 mM, the amino acid is lysine at a concentration of 0.7 to 0.8M, the temperature is 50° C. and the period is about 5 hours and the antibody concentration is 2 to 3 g/L, such as 2.75 g/L. Advantageously the yield may be up to 82% with 79% or more thereof is monomer.

Antibody molecule as employed herein refers to an antibody (i.e. a whole antibody) or a binding fragment thereof.

The term 'antibody' relates to intact (whole) antibodies i.e. comprising the elements of two heavy chains and two light chains, molecules comprising whole antibodies or a binding fragment thereof. Binding fragment as employed herein refers to antibody like molecule comprising one, two, three or more binding sites, wherein the molecule does not contain a full length heavy chain or light chain of a "whole antibody". In one embodiment the binding fragment does not comprise a $C_H2$ and/or a $C_H3$ domain(s). Binding fragments of antibodies include single chain antibodies (i.e. a full length heavy chain and light chain); Fab, modified Fab, Fab', modified Fab', F(ab')2, Fv, Fab-Fv, Fab-dsFv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217), for example the FabFv formats disclosed in WO2009/040562 and disulphide stabilised versions thereof as disclosed in WO2010/035012. The term "Fab fragment" as used herein refers to an antibody fragment comprising a light chain fragment comprising a VL (variable light) domain and a constant domain of a light chain (CL), and a VH (variable heavy) domain and a first constant domain (CH1) of a heavy chain.

The methods for creating and manufacturing antibody fragments are well known in the art (see for example Verma et al., 1998, Journal of Immunological Methods, 216, 165-181). Other antibody fragments for use in the present disclosure include the Fab and Fab' fragments described in WO2005/003169, WO2005/003170 and WO2005/003171.

Typical Fab' molecule comprises a heavy and a light chain pair in which the heavy chain comprises a variable region $V_H$, a constant domain $C_H1$ and a hinge region and the light chain comprises a variable region $V_L$ and a constant domain $C_L$. In one embodiment there is provided a dimer of a Fab' for example dimerisation may be through the hinge.

In one embodiment the recombinantly expressed antibody molecule is a multispecific antibody molecule, such as a bispecific or trispecific antibody. "Bi-specific molecule" as employed herein refers to a molecule with two antigen binding sites, which may bind the same or different antigens. "Tri-specific molecule" as employed herein refers to a molecule with three antigen binding sites, which may bind the same o different antigens. "Multi-specific antibody" as employed herein refers to an antibody molecule as described herein which has two or more binding domains, for example two or three binding domains. In one embodiment the domains all bind the same antigen, including binding the same epitope on the antigen or binding different epitopes on the antigen.

"Antigen binding site" as employed herein refers to a portion of the molecule, which comprises a pair of variable regions, in particular a cognate pair, that interacts specifically with the target antigen. Binding site, antigen binding site, binding domain, antigen binding domain are employed interchangeably herein unless the context indicates otherwise.

Thus in one embodiment the antibody molecule comprises a binding domain. A binding domain will generally comprise 6 CDRs, three from a heavy chain and three from a light chain. In one embodiment 3 CDRs from each chain are in a framework and together with that framework they form a variable region. Thus in one embodiment an antibody molecule comprises a binding domain specific for antigen comprising a light chain variable region and a heavy chain variable region. Active fragment as employed herein is synonymous with a binding fragment.

"Specifically" as employed herein is intended to refer to an antigen binding site that only recognises the antigen to which it is specific or a binding site that has significantly higher binding affinity to the antigen to which is specific compared to affinity to antigens to which it is non-specific, for example 5, 6, 7, 8, 9, 10 times higher binding affinity.

Binding affinity may be measured by standard assay, for example surface plasmon resonance, such as BIAcore.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system. In the method of the present invention the antibody comprises at least one Fv (VH/VL pair) with specificity for an antigen of interest wherein said VH and VL are connected directly or indirectly via one or more linkers and are stabilised by a disulfide bond therebetween.

In one embodiment the antibody or binding fragment thereof comprises a further disulfide bond, for example the where the disulfide is an interchain disulfide bond such as between the heavy and the light chain and/or wherein the in the hinge region between two heavy chains.

In one embodiment the recombinantly expressed antibody molecule comprises one or more, for example one, two, three, four, five or six disulfide bonds. In one embodiment the disulfides are naturally occurring. In one embodiment one or more disulfides are engineered to be in a particular location. In one embodiment there is at least one naturally occurring disulfide bond and at least one engineered disulfide bond. An engineered disulfide bond as employed herein refers to where one or both sulphurs in the disulfide bonds was/were introduced by recombinant genetic engineering techniques.

The position of the disulfide bond between the VH and VL is not limited. Examples of locations for disulfide bonds in the variable domains include, but are not limited to, a position selected from the group comprising:

$V_H37+V_L95C$ see for example Protein Science 6, 781-788 Zhu et al (1997);

$V_H44+V_L100$ see for example; Biochemistry 33 5451-5459 Reiter et al (1994); or Journal of Biological Chemistry Vol. 269 No. 28 pp. 18327-18331 Reiter et al (1994); or Protein Engineering, vol. 10 no. 12 pp. 1453-1459 Rajagopal et al (1997);

$V_H44+V_L105$ see for example J Biochem. 118, 825-831 Luo et al (1995);

$V_H45+V_L87$ see for example Protein Science 6, 781-788 Zhu et al (1997);

$V_H55+V_L101$ see for example FEBS Letters 377 135-139 Young et al (1995);

$V_H100+V_L50$ see for example Biochemistry 29 1362-1367 Glockshuber et al (1990);

$V_H100 b+V_L49$;

$V_H98+V_L46$ see for example Protein Science 6, 781-788 Zhu et al (1997);

$V_H101+V_L46$;

$V_H105+V_L43$ see for example; Proc. Natl. Acad. Sci. USA Vol. 90 pp. 7538-7542 Brinkmann et al (1993); or Proteins 19, 35-47 Jung et al (1994), $V_H106+V_L57$ see for example FEBS Letters 377 135-139 Young et al (1995) and a position or positions corresponding thereto in variable region pair located in the molecule.

Accordingly in one embodiment a variable domain pair (VH/VL) of the present invention may be linked by a disulfide bond between two cysteine residues, one in VH and one in VL, wherein the position of the pair of cysteine residues is selected from the group consisting of VH37 and VL95, VH44 and VL100, VH44 and VL105, VH45 and VL87, VH100 and VL50, VH100b and VL49, VH98 and VL46, VH101 and VL46, VH105 and VL43 and VH106 and VL57. In one embodiment, the disulfide bond is formed between positions VH44 and VL100.

The amino acid pairs listed above are in the positions conducive to replacement by cysteines such that disulfide bonds can be formed. Cysteines can be engineered into these desired positions by known techniques. In one embodiment therefore an engineered cysteine according to the present disclosure refers to where the naturally occurring residue at a given amino acid position has been replaced with a cysteine residue.

Introduction of engineered cysteines can be performed using any method known in the art. These methods include, but are not limited to, PCR extension overlap mutagenesis, site-directed mutagenesis or cassette mutagenesis (see, generally, Sambrook et al., Molecular Cloning, A Laboratory Manual, Cold Spring Harbour Laboratory Press, Cold Spring Harbour, N Y, 1989; Ausbel et al., Current Protocols in Molecular Biology, Greene Publishing & Wiley-Interscience, N Y, 1993). Site-directed mutagenesis kits are commercially available, e.g. QuikChange® Site-Directed Mutagenesis kit (Stratagen, La Jolla, Calif.). Cassette mutagenesis can be performed based on Wells et al., 1985, Gene, 34:315-323. Alternatively, mutants can be made by total gene synthesis by annealing, ligation and PCR amplification and cloning of overlapping oligonucleotides.

Generally the VH/VL pair, wherein the VH and VL are connected directly or indirectly via one or more linkers and are stabilised by a disulfide bond therebetween, is a complementary VH/VL pair which form an antigen binding site and bind the antigen co-operatively i.e. a complementary VH/VL pair which have affinity for the same antigen and bind antigen co-operatively. Typically they will be a VH/VL pair derived from the same antibody, for example an antibody generated in vivo by a host. Bind antigen co-operatively as employed herein refers to the variable regions together bind the target antigen specifically.

In one embodiment the antibody comprises at least one Fv wherein the VH is not fused at the C-terminus to a heavy chain constant domain CH1 and the VL is not fused at the C-terminus to a light chain constant region CL (C kappa or C lambda).

The VH and VL domains are capable of forming interactions, which result in multimer formation through interactions with VH or VL domains in other antibody molecules.

In the Fv the VH and VL domains may be connected directly to each other via a linker or indirectly via linkers to one or more further molecules. The connection between the VH and VL "fixes" or defines the relationship between a given VH and VL pair such that if said VH pairs with a VL in another molecule a multimer is formed because the relationship between the original VH and VL is maintained by the presence of the connection.

In contrast, in a Fv where VH and VL domains are not connected by one or more linkers the VH and VL domains are capable of "coming-apart" (also referred to as breathing) and when they repair if one of the variable domains is not from the original pairing (but has the same sequence as the original variable region which it replaces) then the molecule will only reform as a monomer.

The linker referred to in the present invention is preferably not a disulfide bond. Suitable linkers for use in antibodies are well known in the art. The linker may comprise one or more amino acids. In a further embodiment the linker is a peptide linker comprising 2 to 40 amino acids, such as 2 to 30, 2 to 20 or 2 to 10 amino acids. Examples of peptide linkers include those disclosed below.

In one embodiment the linker is selected from a sequence shown in sequence 39 to 90.

Hinge Linker Sequences

| SEQ ID NO: | SEQUENCE |
| --- | --- |
| 39 | DKTHTCAA |
| 40 | DKTHTCPPCPA |
| 41 | DKTHTCPPCPATCPPCPA |
| 42 | DKTHTCPPCPATCPPCPATCPPCPA |
| 43 | DKTHTCPPCPAGKPTLYNSLVMSDTAGTCY |
| 44 | DKTHTCPPCPAGKPTHVNVSVVMAEVDGTCY |
| 45 | DKTHTCCVECPPCPA |
| 46 | DKTHTCPRCPEPKSCDTPPPCPRCPA |
| 47 | DKTHTCPSCPA |

Flexible Linker Sequences

| SEQ ID NO: | SEQUENCE |
| --- | --- |
| 48 | SGGGGSE |
| 49 | DKTHTS |
| 50 | (S)GGGGS |
| 51 | (S)GGGGSGGGGS |
| 52 | (S)GGGGSGGGGSGGGGS |
| 53 | (S)GGGGSGGGGSGGGGSGGGGS |
| 54 | (S)GGGGSGGGGSGGGGSGGGGSGGGGS |

| SEQ ID NO: | SEQUENCE |
| --- | --- |
| 55 | AAAGSG-GASAS |
| 56 | AAAGSG-XGGGS-GASAS |
| 57 | AAAGSG-XGGGSXGGGS-GASAS |
| 58 | AAAGSG-XGGGSXGGGSXGGGS-GASAS |
| 59 | AAAGSG-XGGGSXGGGSXGGGSXGGGS-GASAS |
| 60 | AAAGSG-XS-GASAS |
| 61 | PGGNRGTTTTRRPATTTGSSPGPTQSHY |
| 62 | ATTTGSSPGPT |
| 63 | ATTTGS |
| — | GS |
| 64 | EPSGPISTINSPPSKESHKSP |
| 65 | GTVAAPSVFIFPPSD |
| 66 | GGGGIAPSMVGGGGS |
| 67 | GGGGKVEGAGGGGGS |
| 68 | GGGGSMKSHDGGGGS |
| 69 | GGGGNLITIVGGGGS |
| 70 | GGGGVVPSLPGGGGS |
| 71 | GGEKSIPGGGGS |
| 72 | RPLSYRPPFPFGFPSVRP |
| 73 | YPRSIYIRRRHPSPSLTT |
| 74 | TPSHLSHILPSFGLPTFN |
| 75 | RPVSPFTFPRLSNSWLPA |
| 76 | SPAAHFPRSIPRPGPIRT |
| 77 | APGPSAPSHRSLPSRAFG |
| 78 | PRNSIHFLHPLLVAPLGA |
| 79 | MPSLSGVLQVRYLSPPDL |
| 80 | SPQYPSPLTLTLPPHPSL |
| 81 | NPSLNPPSYLHRAPSRIS |
| 82 | LPWRTSLLPSLPLRRRP |
| 83 | PPLFAKGPVGLLSRSFPP |
| 84 | VPPAPVVSLRSAHARPPY |
| 85 | LRPTPPRVRSYTCCPTP- |
| 86 | PNVAHVLPLLTVPWDNLR |
| 87 | CNPLLPLCARSPAVRTFP |
| 88 | GGGGSGGGTGGGS |

(S) is optional in sequences 50 to 54.

Examples of rigid linkers include the peptide sequences GAPAPAAPAPA (SEQ ID NO:89), PPPP (SEQ ID NO:90) and PPP.

In one aspect of the present invention, the Fv comprises a VH domain and VL domain which are connected directly by a single linker. Suitable linkers for directly connecting the VH domain and VL domain are described above.

In one embodiment the VH and VL form a disulphide-stabilised single chain variable fragment, also referred to as a dsscFv, molecule which is a single chain variable fragment with a peptide linker between the $V_H$ and $V_L$ variable domain and an inter-domain disulphide bond between said $V_H$ and $V_L$.

In this embodiment, the dsscFv molecule may be fused to one or more further molecules, preferably a second antibody or binding fragment thereof to form bi, tri or tetra-valent antibodies. The dsscFv is fused to one or more further molecules via one or more linkers which may be positioned in the VH domain, the VL domain or both the VH and VL. For example, one or more dsscFv molecules may be fused to the C-terminus or N-terminus of one or more chains of a whole antibody or binding fragment thereof. For example, two or more dsscFv molecules may be fused together to form a Diabody, a tandem scFV (bis-dsscFv) or a Minibody.

Antibody formats which may have a propensity to multimerise through an Fv region include the scFv, Diabody, tandem scFv, tandem scFv-Fc, scFv-Fc, scFv-Fc-scFv Fab-scFv, scDiabody, scDiabody-Fc, scDiabodyCH3, IgG-scFv, scFv-IgG, two-in-one IgG, Dual V domain IgG, IgG-V and V-Ig. When a disulfide bond is employed in the Fv or scFv to stabilise these constructs then it may be beneficial to employ the present method to improve the yield of monomer obtained.

In a further aspect of the present invention, each VH and VL comprises a linker which indirectly connect the VH and VL via a second molecule. In this aspect, the VH domain and the VL domain are linked to the second molecule via separate linkers. Suitable linkers for linking each variable domain to the second molecule are described above. The second molecule provides the indirect connection between the VH and VL. Each VL and VH is linked to the second molecule in a suitable position in order to allow the VH and VL domains to bind the target antigen co-operatively. The VH domain and VL domain are not connected directly to each other by a peptide bond or a peptide linker.

In this aspect, the second molecule is preferably a second antibody or binding fragment thereof to form bi, tri or tetra-valent antibodies. In one embodiment, the VH and VL domains are linked indirectly via a whole antibody or a Fab, modified Fab, Fab', modified Fab' or F(ab')2. For example, when the second antibody is a Fab the VH domain may be fused to the C-terminus of the heavy chain constant region such as the CH1 of the second antibody and the VL single domain antibody may be fused to the C-terminus of the light chain constant region (C kappa or C lambda) of the second antibody, thereby forming a Fab-dsFv. Fab-dsFv antibodies are described in detail in WO2010/035012 and WO2011/036460 both incorporated herein by reference.

The antibody may comprise further binding domains for example as per the disulfide stabilized DVD-Ig molecule as disclosed in WO2011/117653, or the so-called (FabFv)₂Fc described in WO2011/030107, each incorporated herein by reference. Thus antibody as employed herein includes bi, tri or tetra-valent antibodies.

Other suitable antibody formats which may be employed in the method of the present invention are described in WO2011/030107 which discloses FabFvFc and (FabFv)₂Fc antibodies, WO2011/061492 which discloses Fab-dsFv antibodies conjugated to PEG and WO2011/086091 which discloses Fab-dsFv-dsFv each incorporated herein by reference, wherein a disulfide bond is employed in the Fv or scFv.

Other suitable antibody formats which may be employed in the method of the present invention to improve monomer yield are described in WO2015/197772, incorporated herein by reference, which discloses a multi-specific antibody molecule comprising or consisting of:

a) a polypeptide chain of formula (I):

VH-CH1-X-V1; and b) a polypeptide chain of formula (II):

VL-CL-Y-V2;

wherein:
VH represents a heavy chain variable domain;
CH1 represents a domain of a heavy chain constant region, for example domain 1 thereof;
X represents a bond or linker;
Y represents a bond or linker;
V1 represents a dsFv, a sdAb, a scFv or a dsscFv;
VL represents a light chain variable domain;
CL represents a domain from a light chain constant region, such as Ckappa;
V2 represents a dsFv, a sdAb, a scFv or a dsseFv dsscFv
wherein at least one of V1 and V2 is a dsscFv.

"Single chain variable fragment" or "scFv" as employed herein refers to a single chain variable fragment comprising or consisting of a heavy chain variable domain ($V_H$) and a light chain variable domain ($V_L$) which is stabilised by a peptide linker between the $V_H$ and $V_L$ variable domains. The $V_H$ and $V_L$ variable domains may be in any suitable orientation, for example the C-terminus of $V_H$ may be linked to the N-terminus of $V_L$ or the C-terminus of $V_L$ may be linked to the N-terminus of $V_H$.

"Disulphide-stabilised single chain variable fragment" or "dsscFv" as employed herein refers to a single chain variable fragment which is stabilised by a peptide linker between the $V_H$ and $V_L$ variable domain and also includes an inter-domain disulphide bond between $V_H$ and $V_L$.

"Disulphide-stabilised variable fragment" or "dsFv" as employed herein refers to a single chain variable fragment which does not include a peptide linker between the $V_H$ and $V_L$ variable domains and is instead stabilised by an inter-domain disulphide bond between $V_H$ and $V_L$.

"Single domain antibody" or "sdAb" as employed herein refers to an antibody fragment consisting of a single monomeric variable antibody domain, such as $V_H$ or $V_L$ or VHH.

Example antibody formats are shown in FIG. 28. In one embodiment, both V1 and V2 are dsscFv and this antibody format may also be referred to herein as a Fab-2xdsscFv. The $V_H$ and $V_L$ variable domains may be in any suitable orientation, for example the C-terminus of $V_H$ may be linked to the N-terminus of $V_L$ or the C-terminus of $V_L$ may be linked to the N-terminus of $V_H$.

Figure 29:
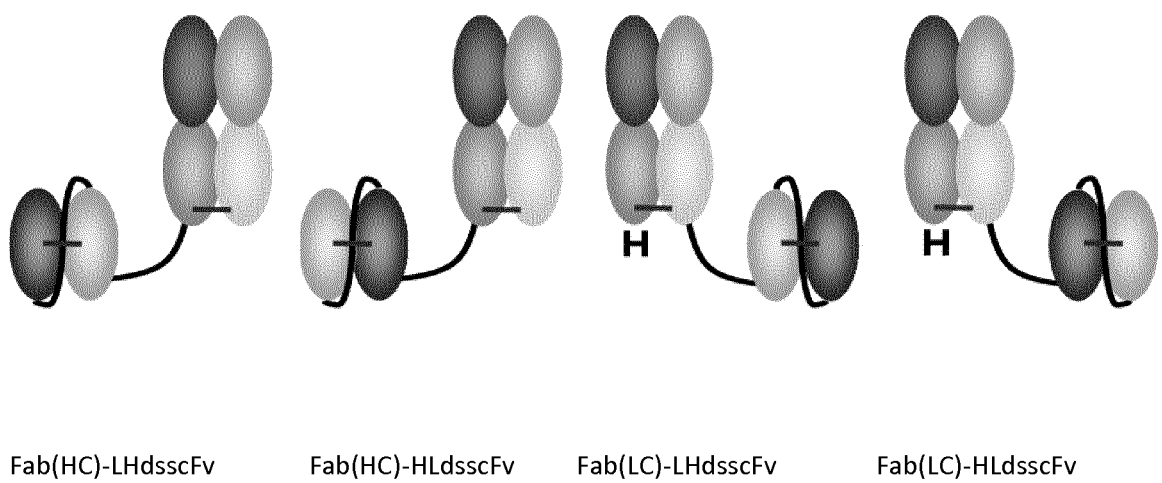
FIG. 29 shows example antibody formats.

Other suitable antibody formats which may be employed in the method of the present invention to improve monomer yield are described in Example 4 of WO2013/068571, incorporated herein by reference, which discloses a Fab-dsscFv antibody format. Example antibody formats are shown in FIG. 29.

In one embodiment the antibody does not comprise a $C_H2$ and/or $C_H3$ domain.

In one embodiment the antibody fragment is the so-called Fab-dsFv format, for example as disclosed in WO2010/035012 and WO2011/036460, each incorporated herein by reference.

In one embodiment the antibody is a disulfide stabilised Fab as disclosed in WO2011/117648. In one embodiment the antibody is not a disulfide stabilised Fab as disclosed in WO2011/117648.

In one embodiment the antibody comprises a binding domain specific to OX40.

In one embodiment the antibody comprises a binding domain specific to serum albumin.

In one embodiment the antibody comprises a binding domain specific to OX40 and a binding domain specific to serum albumin, in particular a Fab-dsFv format, such as wherein the serum albumin binding domain is the Fv portion, in particular the bispecific construct specific to OX40 and human serum albumin disclosed in WO2013/068563 incorporated herein by reference.

The present disclosure provides a bispecific antibody fusion protein which binds human OX40 and human serum albumin comprising:

a heavy chain comprising, in sequence from the N-terminal, a first heavy chain variable domain ($V_H1$), a $C_H1$ domain and a second heavy chain variable domain. ($V_H2$), a light chain comprising, in sequence from the N-terminal, a first light chain variable domain ($V_L1$), a $C_L$ domain and a second light chain variable domain ($V_L2$), wherein said heavy and light chains are aligned such that $V_H1$ and $V_L1$ form a first antigen binding site and $V_H2$ and $V_L2$ form a second antigen binding site, wherein the antigen bound by the first antigen binding site is human OX40 and the antigen bound by the second antigen binding site is human serum albumin, in particular, wherein the first variable domain of the heavy chain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first variable domain of the light chain ($V_L1$) comprises the sequence given in SEQ ID NO:4 for CDR-L1, the sequence given in SEQ ID NO:5 for CDR-L2 and the sequence given in SEQ ID NO:6 for CDR-L3, wherein the second heavy chain variable domain ($V_H2$) has the sequence given in SEQ ID NO:11 and the second light chain variable domain ($V_L2$) has the sequence given in SEQ ID NO: 12 and the second heavy chain variable domain ($V_H2$) and second light chain variable domain ($V_L2$) are linked by a disulfide bond.

In one embodiment there is a peptide linker between the CH1 domain and the second heavy chain variable domain (VH2). In one embodiment there is a peptide linker between the CL domain and the second light chain variable domain (VL1). In one embodiment the first heavy chain variable domain (VH1) comprises the sequence given in SEQ ID NO:8. In one embodiment the first light chain variable domain (VL1) comprises the sequence given in SEQ ID NO:7. In one embodiment the heavy chain comprises or consists of the sequence given in SEQ ID NO:15. In one embodiment the light chain comprises or consists of the sequence given in SEQ ID NO:16.

In one embodiment the antibody molecule comprises a serum albumin binding domain, for example comprising one, two three heavy chain CDRs from the variable region shown in SEQ ID NO: 29 or 30, and one, two or three light chain CDRs from the variable region shown in SEQ ID NO: 31 or 32, in particular three heavy chain CDRs from the variable region shown in SEQ ID NO: 29 or 30, such as CDRH1 for CDRH1, CDRH2 for CDH2, CDRH3 for CDH3 and three light chain CDRs from the variable region shown in SEQ ID NO: 31 or 32, such as CDRL1 for CDRL1, CDRL2 for CDL2, CDRL3 for CDL3.

In one embodiment the antibody molecule comprises a heavy variable region shown in SEQ ID NO: 30. In one embodiment the antibody molecule comprises a light variable region shown in SEQ ID NO: 32. In one embodiment the antibody molecule comprises a heavy variable region shown in SEQ ID NO 30 and a light variable region shown in SEQ ID NO: 32.

In one embodiment the heavy chain comprises or consists of SEQ ID NO: 15 or 19. In one embodiment the light chain comprises or consists of SEQ ID NO: 16 or 20. In one embodiment the binding fragment antibody molecule comprises SEQ ID NO: 15 and 16, 15 and 20, 16 and 19 or 19 and 20. Thus in one embodiment there is provided a bispecific antibody fusion protein which binds human OX40 and human serum albumin, having a heavy chain comprising the sequence given in SEQ ID NO:15 and a light chain comprising the sequence given in SEQ ID NO:16.

In one embodiment the antibody molecule, such as a Fab-dsFv format is one disclosed in WO2014/019727, incorporated herein by reference.

In one embodiment the antibody molecule comprises a binding domain specific to human serum albumin, in particular with CDRs or variable regions as disclosed in WO2013/068571, incorporated herein by reference.

In one embodiment the antibody or fragment according to the present disclosure is monoclonal. Monoclonal antibodies may be prepared by any method known in the art such as the hybridoma technique (Kohler & Milstein, *Nature*, 1975, 256, 495-497), the trioma technique, the human B-cell hybridoma technique (Kozbor et al., *Immunology Today*, 1983, 4, 72) and the EBV-hybridoma technique (Cole et al., "Monoclonal Antibodies and Cancer Therapy", pp. 77-96, Alan R. Liss, Inc., 1985).

Antibodies molecules employed in the methods of the present disclosure may also be generated using single lymphocyte antibody methods by cloning and expressing immunoglobulin variable region cDNAs generated from single lymphocytes selected for the production of specific antibodies by, for example, the methods described by Babcook, J. et al., *Proc. Natl. Acad. Sci. USA*, 1996, 93(15), 7843-7848, WO92/02551, WO2004/051268 and WO2004/106377.

Humanized antibodies molecules are antibody molecules from non-human species having one or more complementarity determining regions (CDRs) from the non-human species and a framework region from a human immunoglobulin molecule which optionally comprise one or more donor residues from the non-human species (see, for example, U.S. Pat. No. 5,585,089). In one embodiment the antibodies or binding fragments which are subject to the method of the present disclosure are humanized.

The antibodies employed in the methods of the present invention can also be generated using various phage display methods known in the art and include those disclosed by Brinkman et al., *J. Immunol. Methods*, 1995, 182, 41-50; Ames et al., *J. Immunol. Methods*, 1995, 184, 177-186; Kettleborough et al. *Eur. J. Immunol.*, 1994, 24, 952-958; Persic et al., *Gene*, 1997 187, 9-18; and Burton et al., *Advances in Immunology*, 1994, 57, 191-280; WO90/02809; WO91/10737; WO92/01047; WO92/18619; WO93/11236; WO95/15982; and WO95/20401; and U.S. Pat. Nos. 5,698, 426; 5,223,409; 5,403,484; 5,580,717; 5,427,908; 5,750, 753; 5,821,047; 5,571,698; 5,427,908; 5,516,637; 5,780, 225; 5,658,727; 5,733,743; and 5,969,108.

Transgenic mice, or other organisms, including other mammals, may also be used to generate humanized antibodies, for example using phage technology.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and/or constant region genes have been replaced by their human counterparts e.g. as described in general terms in EP0546073, U.S. Pat. Nos. 5,545,806, 5,569,825, 5,625,126, 5,633,425, 5,661,016, 5,770,429, EP 0438474 and EP0463151.

The antibody material for use in the methods of the present invention may be prepared by the use of recombinant DNA techniques involving the manipulation and re-expression of DNA encoding the antibody variable and constant region(s). Standard molecular biology techniques may be used to modify, add or delete amino acids or domains as desired. Any alterations to the variable or constant regions are still encompassed by the terms 'variable' and 'constant' regions as used herein.

The antibody starting material may be obtained from any species including, for example mouse, rat, rabbit, hamster, camel, llama, goat or human parts of the antibody may be obtained from more than one species, for example the antibody may be chimeric. In one example, the constant regions are from one species and the variable regions from another. The antibody starting material may also be modified. In another example, the variable region of the antibody has been created using recombinant DNA engineering techniques. Such engineered versions include those created for example from natural antibody variable regions by insertions, deletions or changes in or to the amino acid sequences of the natural antibodies. Particular examples of this type include those engineered variable region domains containing at least one CDR and, optionally, one or more framework amino acids from one antibody and the remainder of the variable region domain from a second antibody. The methods for creating and manufacturing these antibodies are well known in the art (see for example, Boss et al., U.S. Pat. No. 4,816,397; Cabilly et al., U.S. Pat. No. 6,331,415; Shrader et al., WO92/02551; Ward et al., 1989, Nature, 341, 544; Orlandi et al., 1989, Proc. Natl. Acad. Sci. USA, 86, 3833; Riechmann et al., 1988, Nature, 322, 323; Bird et al, 1988, Science, 242, 423; Queen et al., U.S. Pat. No. 5,585,089; Adair, WO91/09967; Mountain and Adair, 1992, Biotechnol. Genet. Eng. Rev, 10, 1-142; Verma et al., 1998, Journal of Immunological Methods, 216, 165-181).

In one embodiment the antibody comprises a variable domain pair forming a binding domain is a cognate pair. Cognate pair as employed herein is intended to refer to a natural pair of variable domains, that is to say isolated from a single antibody or antibody expressing cell. Variable domains may have been optimized and/or humanized. Optimised/humanized variable domains derived from a cognate pair will still be considered a cognate pair after optimization/humanization.

Thus the present disclosure extends to subjecting human, humanized or chimeric antibody molecules to the methods disclosed herein.

The antibody may be specific for any target antigen. The antigen may be a cell-associated protein, for example a cell surface protein on cells such as bacterial cells, yeast cells, T-cells, endothelial cells or tumour cells, or it may be a soluble protein. Antigens of interest may also be any medically relevant protein such as those proteins upregulated during disease or infection, for example receptors and/or their corresponding ligands. Particular examples of cell surface proteins include adhesion molecules, for example integrins such as 131 integrins e.g. VLA-4, E-selectin, P selectin or L-selectin, CD2, CD3, CD4, CD5, CD7, CD8, CD11a, CD11b, CD18, CD19, CD20, CD23, CD25, CD33, CD38, CD40, CD40L, CD45, CDW52, CD69, CD134 (OX40), ICOS, BCMP7, CD137, CD27L, CDCP1, CSF1 or CSF1-Receptor, DPCR1, DPCR1, dudulin2, FLJ20584, FLJ40787, HEK2, KIAA0634, KIAA0659, KIAA1246, KIAA1455, LTBP2, LTK, MAL2, MRP2, nectin-like2, NKCC1, PTK7, RAIG1, TCAM1, SC6, BCMP101, BCMP84, BCMP11, DTD, carcinoembryonic antigen (CEA), human milk fat globulin (HMFG1 and 2), MHC Class I and MHC Class II antigens, KDR and VEGF, PD-1, DC-SIGN, TL1A, DR3, IL-7 receptor A and where appropriate, receptors thereof.

Soluble antigens include interleukins such as IL-1, IL-2, IL-3, IL-4, IL-5, IL-6, IL-8, IL-12, IL-13, IL-14, IL-16 or IL-17, such as IL17A and/or IL17F, viral antigens for example respiratory syncytial virus or cytomegalovirus antigens, immunoglobulins, such as IgE, interferons such as interferon α, interferon β or interferon γ, tumour necrosis factor TNF (formerly known as tumour necrosis factor-α and referred to herein as TNF or TNFα), tumor necrosis factor-β, colony stimulating factors such as G-CSF or GM-CSF, and platelet derived growth factors such as PDGF-α, and PDGF-β, WISP-1 and where appropriate receptors thereof. Other antigens include bacterial cell surface antigens, bacterial toxins, viruses such as influenza, EBV, HepA, B and C, bioterrorism agents, radionuclides and heavy metals, and snake and spider venoms and toxins.

In one embodiment the method comprises the further step of purifying an antibody molecule to a standard suitable for administration to a human and then formulating the same.

The antibody molecules purified employing the methods described herein have a high binding affinity, in particular, nanomolar or picomolar.

Affinity may be measured using any suitable method known in the art, including BIAcore™. In one embodiment the antibody or binding fragment has a binding affinity of about 100 pM or better, for example about 50 pM or better, such as about 40 pM or better, in particular 30 pM or better. In one embodiment the antibody or binding fragment is fully human or humanised and has a binding affinity of about 100 pM or better.

A derivative of a naturally occurring domain as employed herein is intended to refer to where one, two, three, four or five amino acids in a naturally occurring sequence have been replaced or deleted, for example to optimize the properties of the domain such as by eliminating undesirable properties but wherein the characterizing feature(s) of the domain is/are retained.

It will also be understood by one skilled in the art that the antibody may undergo a variety of posttranslational modifications. The type and extent of these modifications often depends on the host cell line used to express the molecule as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705: 129-134, 1995). These post-translational changes can influence the properties of the molecule and thus impact on downstream processing.

In one embodiment the antibody composition employed in the method of the present disclosure does not comprising sodium acetate, for example at a concentration of 25 mM. In one embodiment the antibody composition employed in the method of the present disclosure does not comprise sodium chloride, for example at a concentration of 25 mM.

Examples of hydrophobic amino acids include alanine, isoleucine, leucine, phenylalanine, proline, glycine, such as alanine, proline or glycine. Examples of polar amino acids include asparagine, histidine, serine, threonine, tyrosine, cysteine, methionine and tryptophan, such as serine. Examples of charged amino acids include arginine, lysine, aspartic acid and glutamic acid, such as arginine or lysine, in particular lysine.

Examples of citrate salts include sodium, potassium, calcium and magnesium, such as sodium or potassium, in particular sodium. Examples of sulphate salts include ammonium, calcium and magnesium, such as ammonium. Examples of carbonate salts (including bicarbonate salts) include sodium, potassium, calcium, magnesium and the corresponding bicarbonate form thereof.

In one embodiment the salt is at concentration of 0.5 to 5 mM, such as 1, 1.5, 2, 2.5, 3, 3.5, 4, 4.5 or 5 mM. In one embodiment the ammonium sulphate is at a concentration of 4 mM. In one embodiment the sodium citrate is at a concentration of 1.5 mM.

In one embodiment the thermal conversion step according to the present disclosure is performed on clarified supernatant. Supernatant may be clarified by any suitable means, for example centrifugation, filtration or the like. In one embodiment the supernatant is clarified employing 0.22 micron filtration.

In one embodiment a step of protein A chromatography is carried out on the supernatant before the thermal conversion step. Protein A purification is particularly advantageous in the context of the type of antibody molecules disclosed herein (in particular those which do not comprise $C_H2$ $C_H3$ domains) because this technique allow multimer to be resolved from monomers.

The use of protein A chromatography can be used to recover a human VH3 domain-containing antibody which does not comprise an Fc region in monomeric form. An avidity effect has been observed between the binding of human VH3 domains and protein A. This finding is surprising given that it has not been described for the interaction between Fc regions and protein A and allows recovery of monomeric human VH3 domain-containing antibodies from a mixture containing monomeric and multimeric forms of the antibody.

Accordingly, the step of protein A purification may comprise a) applying a mixture comprising a human VH3 domain-containing antibody in monomeric and multimeric form to a protein A chromatography material wherein said protein A comprises domain D and/or E, under conditions that allow binding of said antibody to protein A, and b) recovering the human VH3 domain containing-antibody in monomeric form, wherein the human VH3 domain containing antibody does not contain an Fc region. Alternatively the step of protein A purification comprises a) applying a mixture comprising a human VH3 domain-containing antibody in monomeric and multimeric form to a protein A chromatography material wherein said protein A comprises domain D and/or E, b) allowing binding of said antibody to protein A, c) applying an elution buffer that selectively disrupts binding of the antibody in monomeric form, d) recovering the resulting eluate, and optionally e) applying a second elution buffer that disrupts binding of the antibody in multimeric form and recovering this second eluate, wherein the human VH3 domain-containing antibody does not contain an Fc region. In one embodiment, wherein the antibody is antibody A26Fab-645dsFv specific to OX40 and human serum albumin disclosed in WO2013/068563, the protein A purification is carried out as above wherein in step c) the elution buffer has a pH 3.5 to pH 4.2, preferably, pH 3.6 to pH 4.1, pH 3.7 to pH 4.0, preferably pH 3.8 to pH 3.9 or pH 3 to disrupt binding of the monomer and in optional step e) the elution buffer has a pH below 3.5, preferably below pH 3.4, preferably pH 2.8 to pH 3.2, preferably pH 2.9 to pH 3.1, preferably pH 3.0 that disrupts binding of the antibody in multimeric form.

Alternatively the step of protein A purification comprises a) applying a mixture comprising a human VH3 domain-containing antibody in monomeric and multimeric form to a protein A chromatography material wherein said protein A comprises domain D and/or E, b) allowing binding of the antibody in multimeric form, c) recovering the antibody in monomeric form in the flow-through, and optionally d) applying an elution buffer that selectively disrupts binding of the antibody in multimeric form, and e) recovering the eluate resulting from d); wherein the human VH3 domain-containing antibody does not contain an Fc region.

In an alternative embodiment, no protein A chromatography is carried out before the thermal conversion step.

In one embodiment the method comprises a further downstream processing step. In one embodiment the method comprises a further step of downstream purification, for example downstream processing comprises a chromatography step, such as hydrophobic interaction chromatography or ion exchange chromatography.

A downstream processing step as employed herein refers to at least one step employed subsequent to step a) for further purifying the antibody. Examples of downstream processing includes one or more chromatography steps, for example size exclusion chromatography, ion exchange chromatography (such as anion exchange chromatography and/or cation exchange chromatography), hydrophobic interaction chromatography, affinity chromatography, such as protein—A chromatography (such as a MabSelect column) Techniques employed in downstream processing of polypeptides and proteins are well known to those skilled in the art.

In one embodiment the downstream processing comprises at least one chromatography step, in particular ion exchange chromatography. In one embodiment the method comprises an anion exchange chromatographic step followed by a cation exchange chromatographic step or vice versa. In one embodiment hydrophobic interaction chromatography is employed. In one embodiment mixed mode chromatography is employed. In one embodiment multiple chromatography steps are employed.

In one embodiment the method comprises a viral inactivation step, for example holding the composition containing the protein at a defined pH, for example low pH for a defined period.

In one embodiment the final downstream processing step is diafiltration step and buffer exchange to provide the final storage buffer and concentration for the protein.

In one embodiment the downstream processing following the thermal conversion step comprises protein A (such as a MabSelect column) purification, as described above before the thermal conversion step.

In one embodiment the downstream processing further comprises a viral inactivation step, followed by ultrafiltration and buffer exchange, in turn followed by anion exchange chromatography and subsequent cation exchange chromatography and a viral filtration step.

In one embodiment the downstream processing following the thermal conversion step comprises a viral inactivation step, followed by ultrafiltration and buffer exchange, in turn followed by anion exchange chromatography and subsequent cation exchange chromatography and a viral filtration step.

In one embodiment the downstream processing further comprises a viral inactivation step, followed by ultrafiltration and buffer exchange, in turn followed by cation exchange chromatography and subsequent anion exchange chromatography and a viral filtration step.

In one embodiment the downstream processing following the thermal conversion step comprises a viral inactivation step, followed by ultrafiltration and buffer exchange, in turn followed by cation exchange chromatography and subsequent anion exchange chromatography and a viral filtration step.

Other downstream processing steps include hydrophobic interaction chromatography (HIC) or mixed mode chromatography.

In one embodiment the final downstream processing step is diafiltration step and buffer exchange to provide the final storage buffer and concentration for the protein.

In one embodiment the method disclosed herein provided the further step of conjugating a purified monomeric antibody molecule to one or more effector molecules. The effector molecule may comprise a single effector molecule or two or more such molecules so linked as to form a single moiety that can be attached to the antibody molecule.

Where it is desired to obtain an antibody linked to an effector molecule, this may be prepared by standard chemical or recombinant DNA procedures in which the antibody is linked either directly or via a coupling agent to the effector molecule. Techniques for conjugating such effector molecules to an antibody are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO93/06231, WO92/22583, WO89/00195, WO89/01476 and WO03031581. Alternatively, where the effector molecule is a protein or polypeptide the linkage may be achieved using recombinant DNA procedures, for example as described in WO86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, Lu$^{177}$, Bismuth$^{213}$, Californium$^{252}$, Iridium$^{192}$ and Tungsten$^{188}$/Rhenium$^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases. Proteins, polypeptides and peptides of interest include, but are not limited to, immunoglobulins, toxins such as abrin, ricin A, *pseudomonas* exotoxin, or diphtheria toxin, a protein such as insulin, tumour necrosis factor, α-interferon, β-interferon, nerve growth factor, platelet derived growth factor or tissue plasminogen activator, a thrombotic agent or an anti-angiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof. Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody of the disclosure and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example an antibody for use in the present invention is attached to poly(ethyleneglycol) (PEG) moieties. In one particular example the PEG molecules may be attached through any available amino acid side-chain or terminal amino acid functional group located in the antibody, for example any free amino, imino, thiol, hydroxyl or carboxyl group. Such amino acids may occur naturally in the antibody or may be engineered into the antibody using recombinant DNA methods (see for example U.S. Pat. Nos. 5,219,996; 5,667,425; WO98/25971). In one example the molecule of the present invention is a modified antibody wherein the modification is the addition to the C-terminal end of its heavy chain one or more amino acids to allow the attachment of an effector molecule. Multiple sites can be used to attach two or more PEG molecules. In one embodiment a PEG molecule is linked to a cysteine 171 in the light chain, for example see WO2008/038024 incorporated herein by reference.

Suitably PEG molecules are covalently linked through a thiol group of at least one cysteine residue located in the antibody. Each polymer molecule attached to the modified antibody may be covalently linked to the sulphur atom of a cysteine residue located in the antibody. The covalent linkage will generally be a disulfide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody as described above. The activated polymer may be any polymer containing a thiol reactive group such as an α-halocarboxylic acid or ester, e.g. iodoacetamide, an imide, e.g. maleimide, a vinyl sulphone or a disulfide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and SunBio) and M-PEG-SPA (obtainable from Nektar, formerly Shearwater).

In one embodiment the method comprises the further step of formulating the antibody or binding fragment including conjugated versions thereof, as a pharmaceutical formulation suitable for use in humans.

Thus the present disclosure also provides a process step for preparation of a pharmaceutical or diagnostic composition comprising adding and mixing the antibody molecule obtained from the process of the present disclosure together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody molecule or composition according to the disclosure is employed in combination with a further pharmaceutically active agent, for example a corticosteroid (such as fluticasonase propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody molecule. The term "therapeutically effective amount" as used herein refers to an amount of a therapeutic agent needed to treat, ameliorate or prevent a targeted disease or condition, or to exhibit a detectable therapeutic or preventative effect. The therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgment of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which an antibody molecule is administered depends on the nature of the condition to be treated, for example the extent of the disease/inflammation present and on whether the molecule is being used prophylactically or to treat an existing condition.

The frequency of dose will depend on the half-life of the antibody molecule and the duration of its effect. If the antibody has a short half-life (e.g. 2 to 10 hours) it may be necessary to give one or more doses per day. Alternatively, if the antibody has a long half-life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the molecule of the disclosure may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody, for example if the pH of the formulation is 7 then a pI of from 8-9 or above may be appropriate. Whilst not wishing to be bound by theory it is thought that this may ultimately provide a final formulation with improved stability, for example the antibody remains in solution.

The pharmaceutical compositions of this disclosure may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody molecule from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the abovementioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus® nebulizer connected to a Pari Master® compressor manufactured by Pari Respiratory Equipment, Inc., Richmond, Va.).

The antibody or binding fragment obtained from the method herein can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 mL of water so as to achieve a pH of about 4.0 to 5.0. A suspension can employ, for example, lyophilised molecule.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the for the formulation, aseptic suspension of the molecule in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solution buffer.

Comprising in the context of the present specification is intended to meaning including. Where technically appropriate embodiments of the invention may be combined. Any positively recited embodiment herein may be employed as the basis of a negative disclaimer.

The invention will now be described with reference to the following examples, which are merely illustrative and should not in any way be construed as limiting the scope of the present invention.

Example 1: Thermal Conversion of Protein-A Purified Fab-dsFv Multimeric Species CHO Expression and Clarification of A26Fab-dsFv The constructs which binds human OX40 and serum albumin having the light chain sequence A26 Fab Light-(3xG4S)-645dsFv(gL4) (SEQ ID NO:16) and the heavy chain sequence A26 Fab Heavy-(G4S,G4T,G4S)-645dsFv (gH5) (SEQ ID NO:15) was expressed in a stable dihydrofolate reductase (DHFR) deficient Chinese Hamster Ovary cell line (CHO DG44). This was generated by transfection using a Nuclefector (Lonza) following the manufacturer's instructions with a plasmid vector containing both the gene for DHFR as a selectable marker and the genes encoding the product. Transfected cells were selected in medium lacking hypoxanthine and thymidine, and in the presence of the DHFR inhibitor methotrexate.

The cell line was cultivated in medium containing 20 nM methotrexate throughout the inoculum stages. The cells are then cultivated in the absence of methotrexate. For the final culture step, the cells were cultivated in a 80 L stainless steel bioreactor for 14 days in medium in the absence of methotrexate. Clarification of the supernatant was carried out via centrifuged (4000×g for 60 minutes at room temperature) followed by depth and sterile filtration.

Protein-A Purification of Mammalian Expressed A26Fab-645dsFv

Clarified CHO supernatants were applied to a 9.4 ml HiScreen (2 columns in series) MabSelect (GE Healthcare) column equilibrated in Delbeccos Phosphate Buffered Saline (PBS) pH7.4. The column was washed with PBS and the bound material eluted with 0.1M Citrate pH3.5. The collected elution peak was pH adjusted to ~pH7 with 2M Tris/HCl pH 8.5. The pH adjusted elutions were buffer exchanged into PBS pH7.4 using 10 kDa molecular weight cut off centrifugation concentrators.

General Method Employed Non-Reduced SDS-PAGE Analysis of A26Fab-645dsFv

Samples were diluted to 1.0 mg/ml where required in a final volume of 50 μl and then 5 μl of 100 mM NEM was added. Samples were then diluted with 50 μl of Novex Tris-Glycine SDS Sample Buffer (2×) and vortexed before being incubated at 95° C. for 3 minutes. The prepared samples were loaded at 5 μg per well on to a 4-20% acrylamine Tris/Glycine SDS gel and run for 120 minutes at 150V, constant voltage.

General Method Employed Reduced SDS-PAGE Analysis of A26Fab-645dsFv

Samples were diluted to 1.0 mg/ml where required in a final volume of 50 μl reducing agent. Samples were then diluted with 50l of Novex Tris-Glycine SDS Sample Buffer (2×) and vortexed before being incubated at 95° C. for 3 minutes. The prepared samples were loaded at 5 μg protein per well on to a 4-20% acrylamine Tris/Glycine SDS gel and run for 120 minutes at 150V, constant voltage. The gels were stained with Coomasie Blue protein stain, see FIGS. 2 and 12.

General Method for G3000 SEC-HPLC Analysis of A26Fab-645dsFv

50 μg samples were injected onto a TSK Gel G3000SWXL, 7.8×300 mm, column (Tosoh) and developed with an isocratic gradient of 200 mM phosphate pH7.0 at 1 ml/min. Signal detection was by absorbance at 280 nm, see FIGS. 9, 10, 13 and 14. SEC-HPLC analysis was used to determine both % monomer (A26Fab-645dsFv monomer has a retention time around 9 minutes) as well as a method to predict the yield of the conversion process. The predicted yield for the conversion process was calculated by expressing the total peak area at any particular time point as a percentage of the total peak area at T=0.

Thermal Conversion of Protein-A Purified A26Fab-645dsFv, at Constant Reductant Concentration Protein-A purified A26Fab-645dsFv at ~5 mg/ml was diluted 1:1 in a conversion buffer of PBS/100 mM bMEA (β-mercaptoethylamine) resulting in a final bMEA concentration of 50 mM. Post dilution, the samples were incubated at a defined temperature. Samples taken during a time course were put on ice to reduce the temperature and stop the conversion process prior to analysis. Analysis was by SEC-HPLC and monomer level and a yield prediction were determined.

Figure 4:
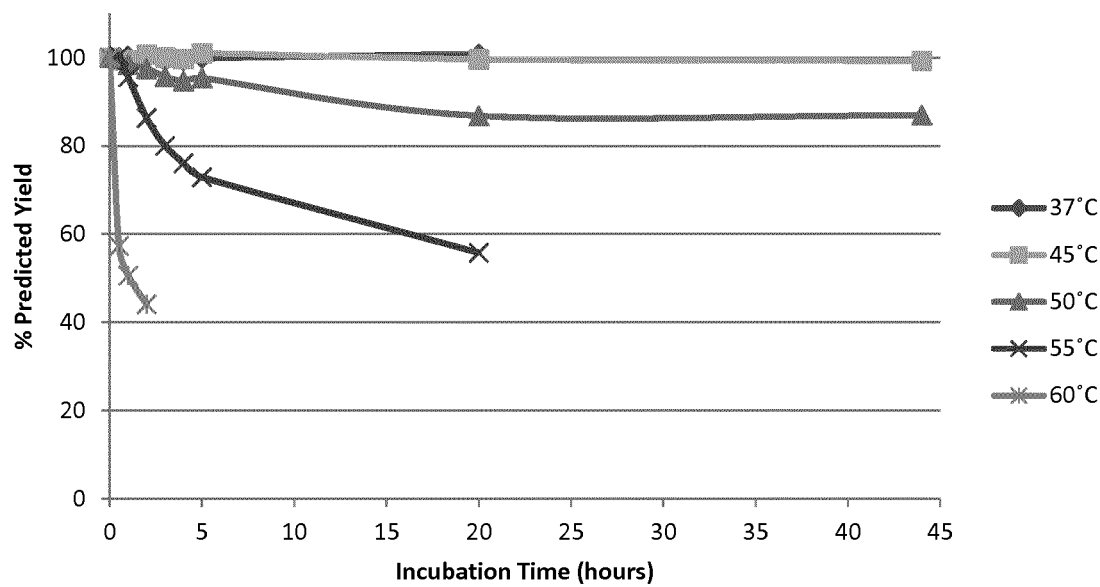
FIG. 4 shows the predicted yield of monomer obtained after treatment as a percentage of the total initial target protein yield before treatment. Predicted yield as employed herein is the yield of monomer as percentage by reference to the staring yield before treatment.
Figure 5:
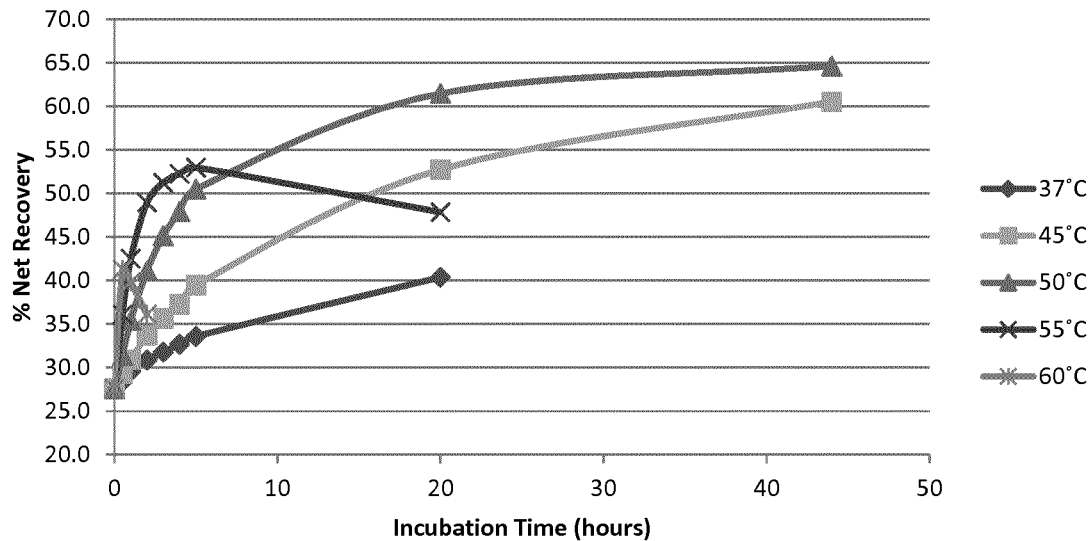
FIG. 5 shows SEC-HPLC analysis of net monomer recovery of antibody A26 Fab-645dsFv over time when treated with 50 mM beta-mercaptanethanol temperatures in the range 37 to 60° C.

Monomer levels were seen to increase at all evaluated temperatures however the rate of conversion was significantly faster at the higher temperatures. In contrast as temperature increased the predicted yield was seen to decrease. In order to calculate the total yield of monomer (net recovery) the percentage monomer levels were divided by 100 and multiplied by the predicted yield. Data is summarised in FIGS. 3, 4, and 5 and in Tables 1-3.

At incubation temperatures ≥55° C. net recoveries reduce after relatively short incubation times. At ≤50° C. net recovery continue to increase over all the evaluated time course. Net recoveries are significantly higher at 45-50° C. with 50° C. appearing optimal at 50 mM bMEA.

Table 1 Total Monomer - Conversion with 50mM bMEA

| Time (hours) | 0 | 0.5 | 1 | 2 | 3 | 4 | 5 | 20 | 44 |
|---|---|---|---|---|---|---|---|---|---|
| 37?+0C | 27.6 | 28.37 | | 29.49 | 30.85 | 31.98 | 32.86 | 33.63 | 40.09 |
| 45?+0C | 27.6 | 29.46 | | 31.12 | 33.51 | 35.62 | 37.39 | 39.11 | 53.00 | 61.01 |
| 50?+0C | 27.6 | 31.48 | | 35.95 | 42.18 | 47.2 | 50.6 | 52.98 | 70.84 | 74.29 |
| 55?+0C | 27.6 | 35.94 | | 44.49 | 56.76 | 64.04 | 68.71 | 72.68 | 85.74 | |
| 60?+0C | 27.6 | 72.03 | | 78.79 | 81.92 | | | | | |

Table 2 Predicted Yield - Conversion with 50mM bMEA

| Time (hours) | 0 | 0.5 | 1 | 2 | 3 | 4 | 5 | 20 | 44 |
|---|---|---|---|---|---|---|---|---|---|
| 37?+0C | 100.0 | | 100.1 | 100.3 | 100.0 | 99.3 | 99.4 | 99.9 | 100.8 |
| 45?+0C | 100.0 | | 99.5 | 99.4 | 100.7 | 100.1 | 99.7 | 101.0 | 99.6 | 99.3 |
| 50?+0C | 100.0 | | 99.8 | 98.5 | 97.5 | 95.7 | 94.7 | 95.4 | 86.8 | 87.0 |
| 55?+0C | 100.0 | | 100.4 | 95.6 | 86.3 | 80.0 | 76.1 | 72.9 | 55.8 | |
| 60?+0C | 100.0 | | 57.3 | 50.6 | 44.1 | | | | | |

Table 3 Net Recovery - Conversion with 50mM bMEA

| Time (hours) | 0 | 0.5 | 1 | 2 | 3 | 4 | 5 | 20 | 44 |
|---|---|---|---|---|---|---|---|---|---|
| 37?+0C | 27.6 | 28.4 | 29.6 | 30.9 | 31.8 | 32.7 | 33.6 | 40.4 | |
| 45?+0C | 27.6 | 29.3 | 30.9 | 33.7 | 35.7 | 37.3 | 39.5 | 52.8 | 60.6 |
| 50?+0C | 27.6 | 31.41 | 35.41 | 41.14 | 45.16 | 47.94 | 50.52 | 61.5 | 64.7 |
| 55?+0C | 27.6 | 36.08 | 42.52 | 48.97 | 51.3 | 52.27 | 52.99 | 47.86 | |
| 60?+0C | 27.6 | 41.3 | 39.85 | 36.14 | | | | | |

Figure 6:
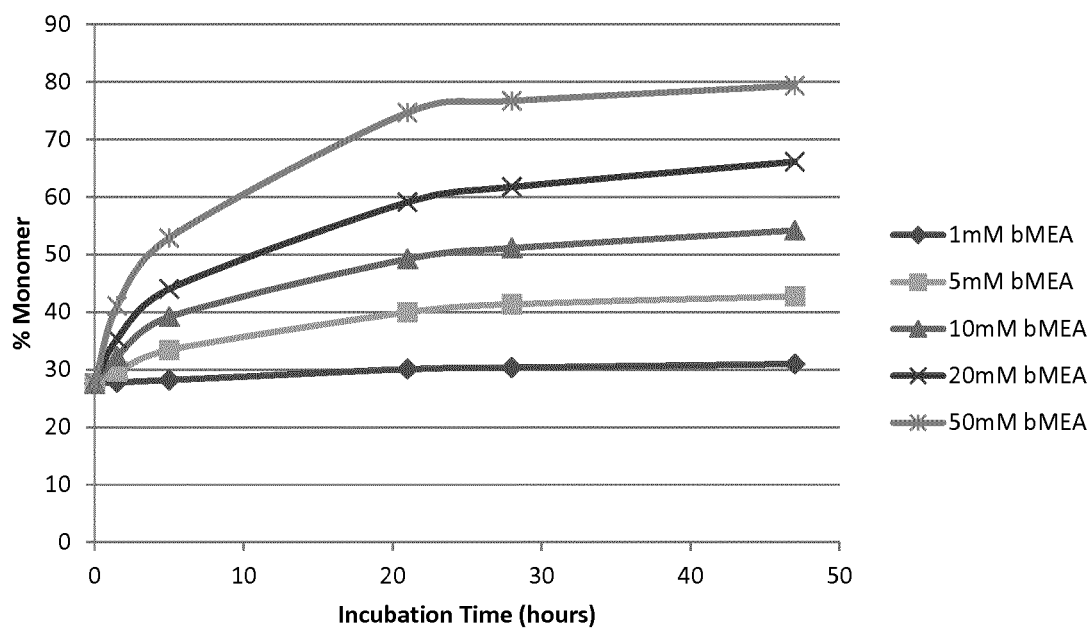
FIG. 6 shows SEC-HPLC analysis of net monomer recovery of antibody A26 Fab-645dsFv over time when treated with concentrations of beta-mercaptanethanol in the range 1 to 50 mM at a temperatures of 50° C.
Figure 7:
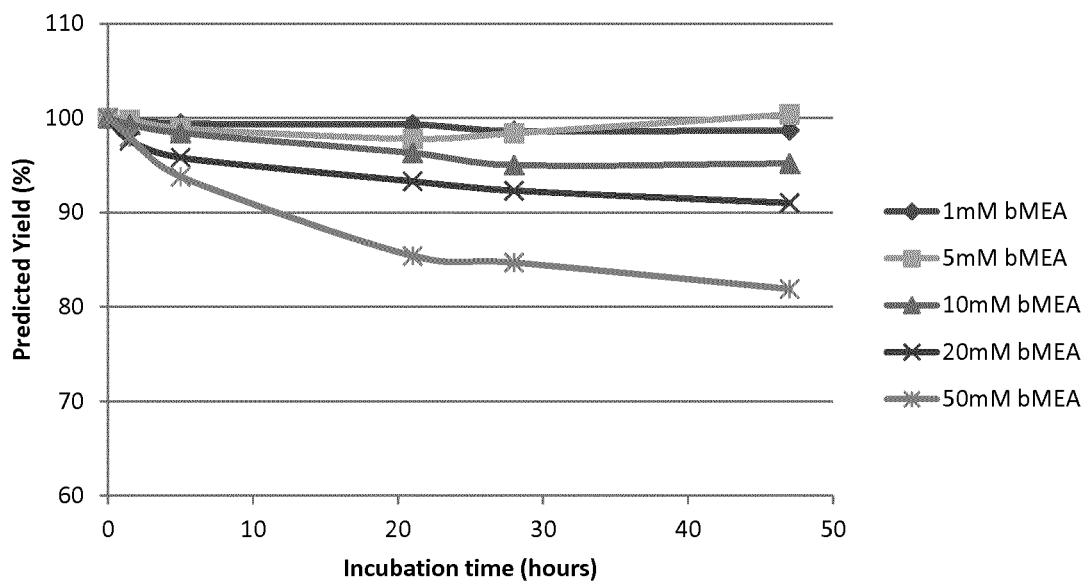
FIG. 7 shows the predicted yield of monomer obtained after treatment as a percentage of the total initial target protein yield before treatment.
Figure 8:
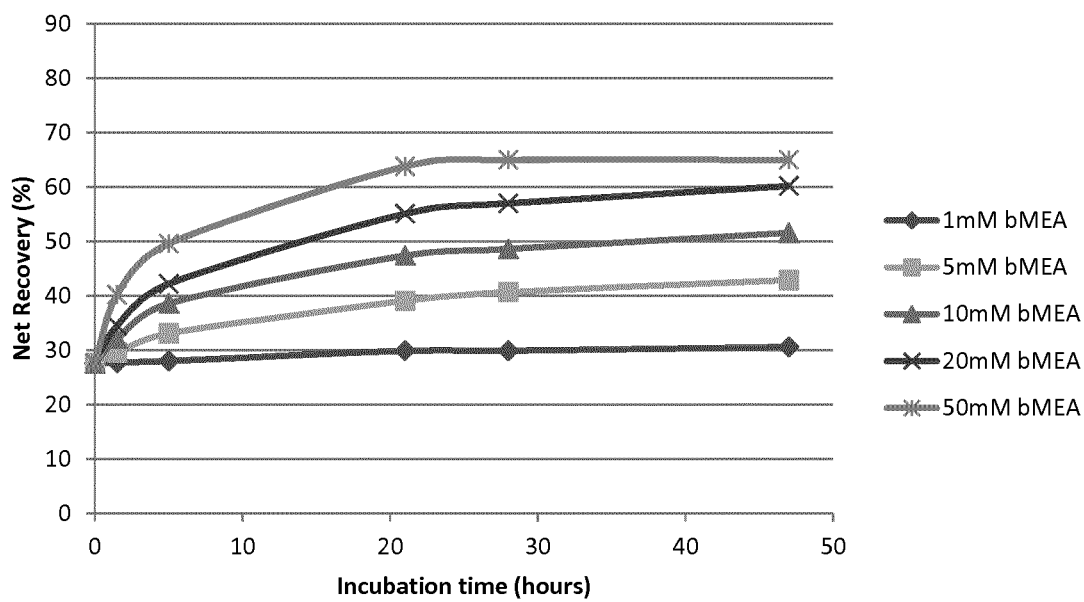
FIG. 8 In process analysis via SEC-HPLC (G3000) determining A26Fab-645dsFv net monomer recovery during the conversion at 50° C. at the stated bMEA concentration.
Figure 9:
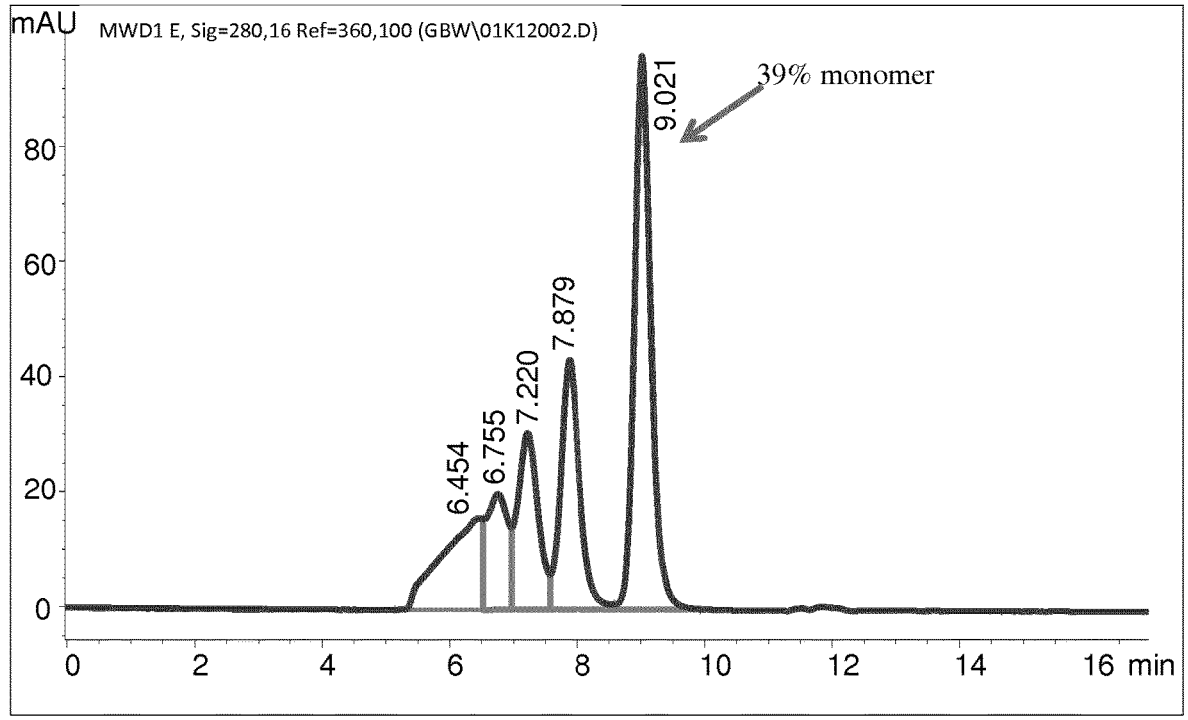
FIG. 9 shows SEC-HPLC chromatogram showing the protein-A purification of supernatant from expression of recombinant antibody A26 Fab-645dsFv, which has not been subject to treatment employing the method of the present disclosure.
Figure 10:
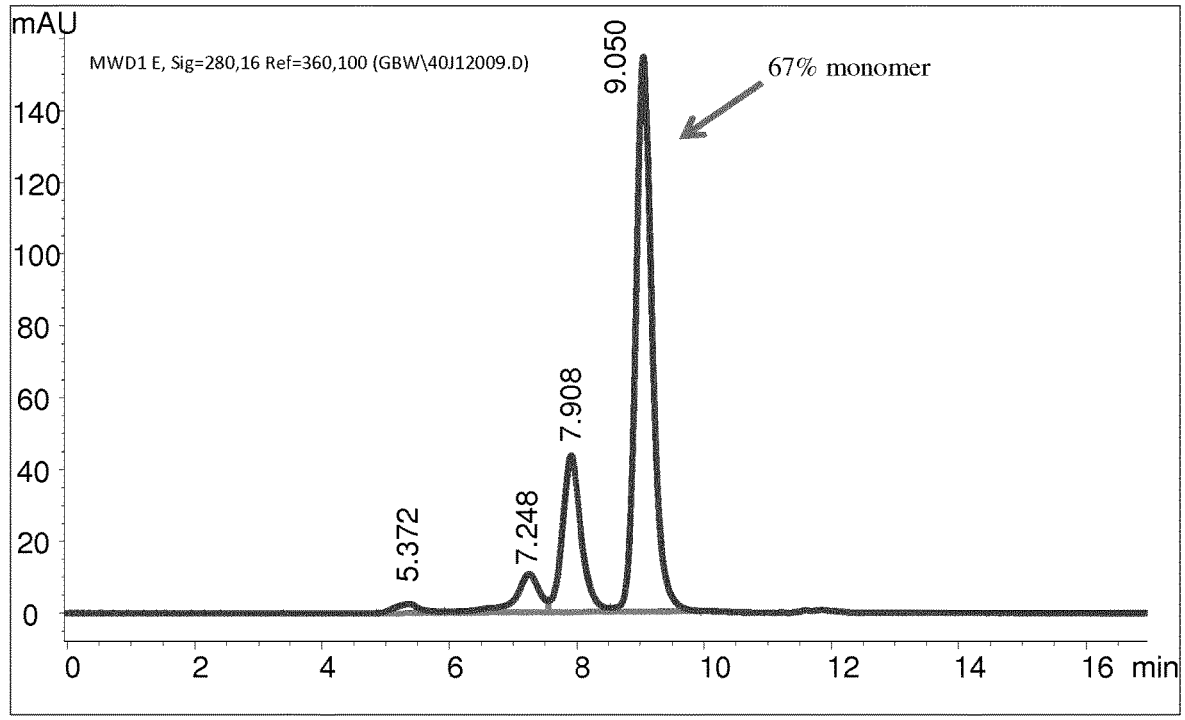
FIG. 10 shows SEC-HPLC chromatogram showing the protein-A purification of supernatant from expression of recombinant antibody A26 Fab-645dsFv, treated with 50 mM beta-mercaptanethanol at 50° C.

Thermal Conversion of Protein-A Purified A26Fab-645dsFv, at Constant Temperature Protein-A purified A26Fab-645dsFv at ~5 mg/ml was diluted 1:1 in a conversion buffer which was a 2× stock of the stated bMEA concentration (1, 5, 10, 20, & 50 mM) in PBS. Post dilution the samples were incubated at 50° C. Samples taken during the time course were put on ice to reduce the temperature and stop the conversion process prior to analysis. Analysis was by SEC-HPLC and monomer level and a yield prediction were determined. Data is summarised in FIGS. 6, 7, and 8 and Tables 4, 5, and 6.

Rate of conversion increased with increased concentrations of bMEA. Net recovery plateaued at ~65% monomer at ≥20 hours. Reduced concentrations of bMEA saw a more gradual increase in monomer levels with little or no increase observed at 1 mM bMEA over the time course.

| Table 4 | Total Monomer - Conversion at 50?+0C and stated bMEA concentration | | | | | |
|---|---|---|---|---|---|---|
| Time (hours) | | | | | | |
| 0 | 1.5 | 5 | 21 | 28 | 47 | |
| 1mM bMEA | 27.6 | 27.8 | 28.2 | 30.1 | 30.3 | 31.0 |
| 5mM bMEA | 27.6 | 29.7 | 33.4 | 40.0 | 41.4 | 42.8 |
| 10mM bMEA | 27.6 | 32.3 | 39.2 | 49.2 | 51.1 | 54.2 |
| 20mM bMEA | 27.6 | 35.3 | 44.0 | 59.1 | 61.7 | 66.1 |
| 50mM bMEA | 27.6 | 41.1 | 52.9 | 74.7 | 76.7 | 79.4 |

| Table 5 | Predicted Yield - Conversion at 50?+0C and stated bMEA concentration | | | | | |
|---|---|---|---|---|---|---|
| Time | (hours) | | | | | |
| 0 | 1.5 | 5 | 21 | 28 | 47 | |
| 1mM bMEA | 100.0 | 99.8 | 99.4 | 99.3 | 98.6 | 98.7 |
| 5mM bMEA | 100.0 | 99.8 | 98.9 | 97.8 | 98.4 | 100.4 |
| 10mM bMEA | 100.0 | 99.3 | 98.4 | 96.3 | 95.0 | 95.2 |
| 20mM bMEA | 100.0 | 97.6 | 95.8 | 93.3 | 92.3 | 91.0 |
| 50mM bMEA | 100.0 | 98.0 | 93.8 | 85.4 | 84.7 | 81.9 |

| Table 6 | Net Recovery - Conversion at 50?+0C and stated bMEA concentration | | | | | |
|---|---|---|---|---|---|---|
| Time (hours) | | | | | | |
| 0 | 1.5 | 5 | 21 | 28 | 47 | |
| 1mM bMEA | 27.6 | 27.7 | 28.0 | 29.9 | 29.9 | 30.6 |
| 5mM bMEA | 27.6 | 29.6 | 33.1 | 39.1 | 40.7 | 42.9 |
| 10mM bMEA | 27.6 | 32.1 | 38.6 | 47.4 | 48.6 | 51.6 |
| 20m1V1 bMEA | 27.6 | 34.5 | 42.2 | 55.1 | 57.0 | 60.2 |
| 50mM bMEA | 27.6 | 40.2 | 49.6 | 63.8 | 65.0 | 65.0 |

Example 2: Thermal Conversion of Fab-dsFv Multimeric Species in Clarified Mammalian Cell Culture Supernatant Thermal Conversion of A26Fab-645dsFv in Mammalian Cell Culture Supernatant Clarified cell culture supernatant was concentrated to half the original volume using 10 kDa molecular weight cut off centrifugation concentrators. The concentrated supernatant was then diluted to the original volume using PBS/100 mM bMEA, to give a final bMEA concentration of 50 mM. The supernatant was then incubated at 50° C. overnight (14.5 hours). Post incubation the supernatant was put on ice to reduce the temperature and stop the conversion process.

Figure 11:
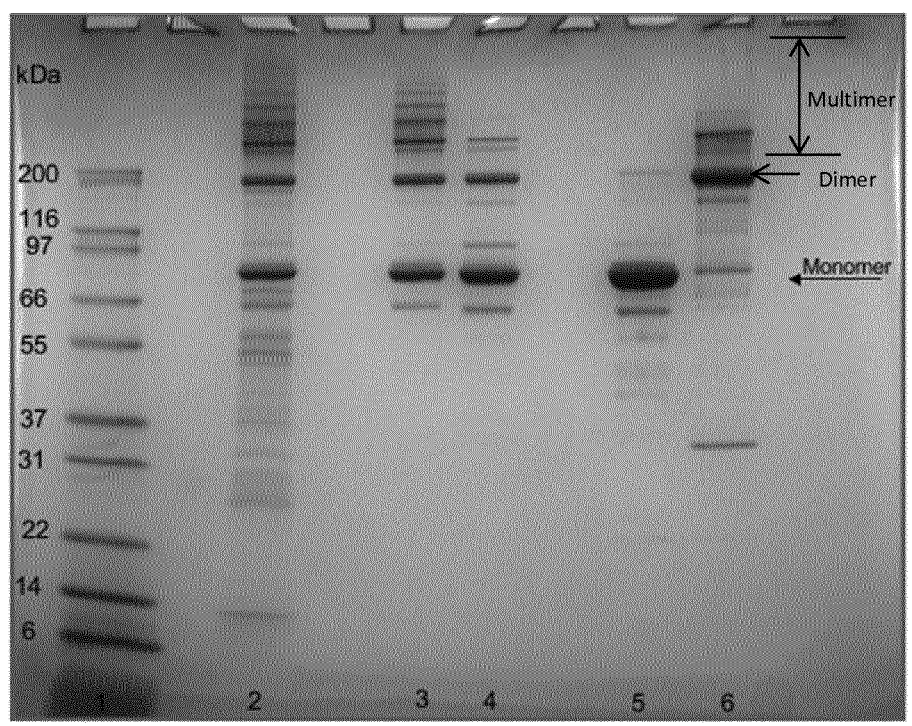
FIG. 11 shows non-reduced SDS-PAGE analysis of A26Fab-645dsFv wherein clarified supernatant was treated with 50 Mm bMEA at 50° before protein A purification.
Figure 12:
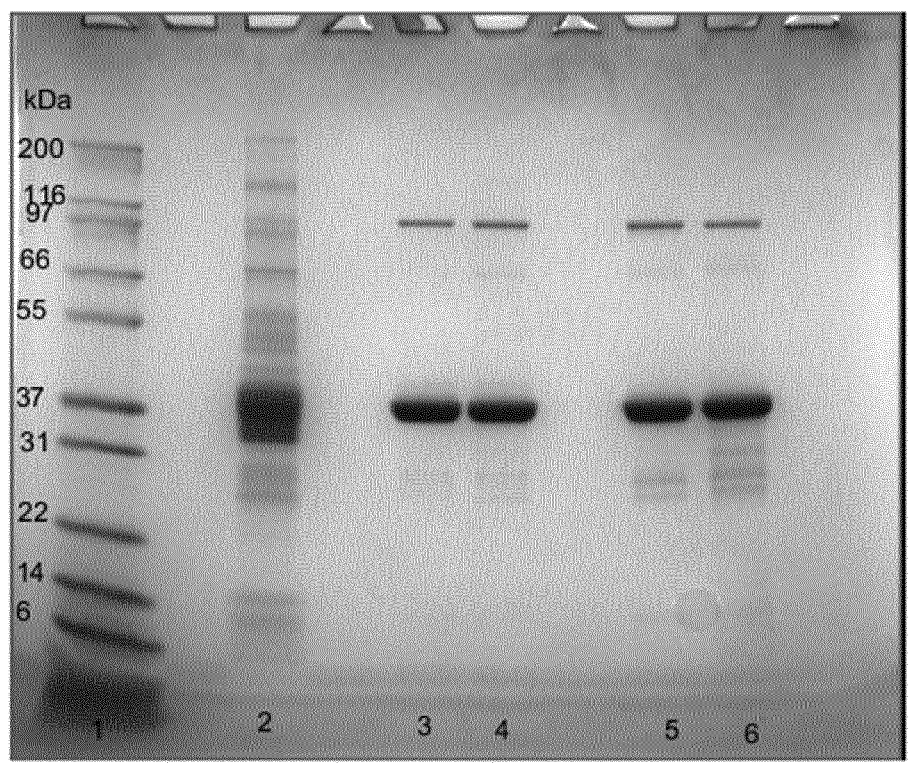
FIG. 12 shows reduced SDS-PAGE analysis of A26Fab-645dsFv wherein clarified supernatant was treated with 50 Mm bMEA at 50° followed by protein A purification.
Figure 13:
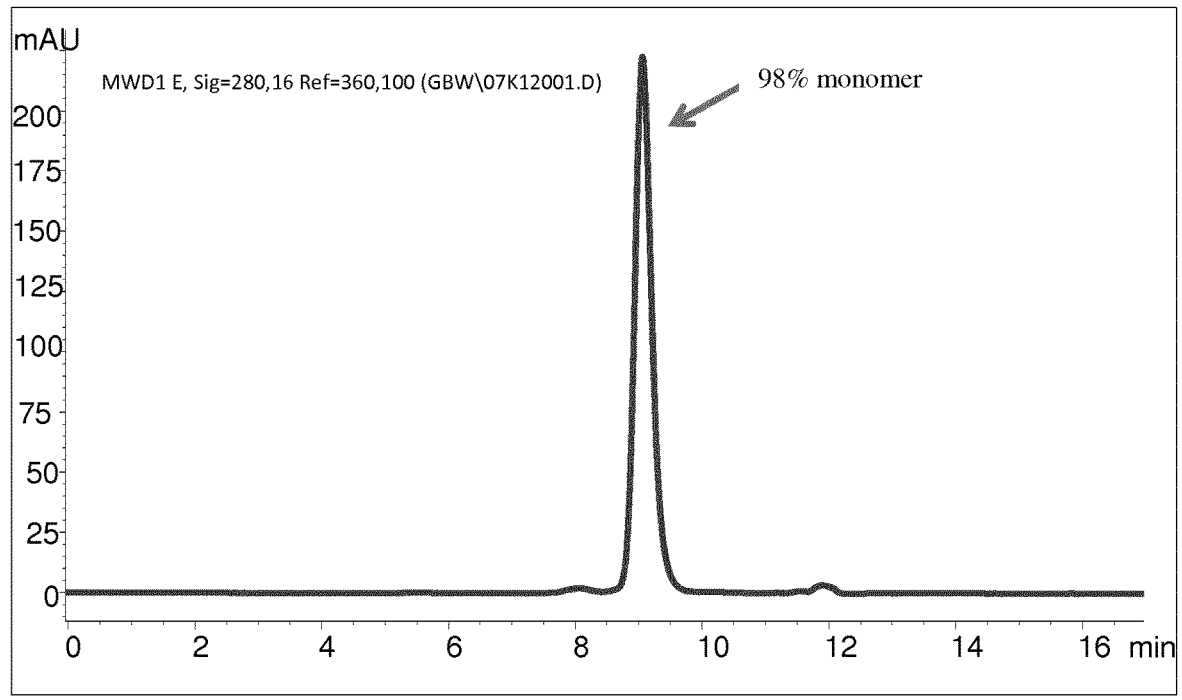
FIGS. 13 & 14 shows SEC-HPLC analysis for antibody material post downstream processing prepared with and without the methods disclosed herein. These figures show that the material obtained using the two processes provide comparable material.
Figure 14:
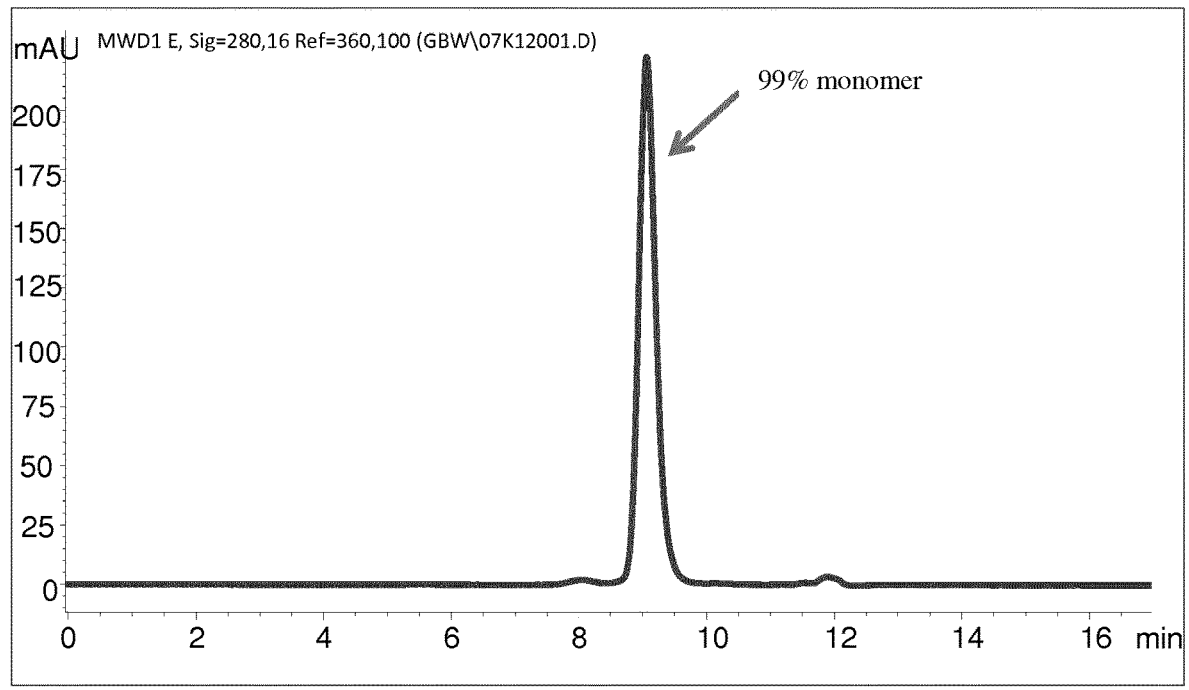

Protein-A Purification of A26Fab-645dsFv from Mammalian Cell Culture Supernatant Following Thermal Conversion Thermal converted CHO supernatant was applied to a 9.4 ml HiScreen (2 columns in series) MabSelect (GE Healthcare) column equilibrated in Delbeccos Phosphate Buffered Saline (PBS) pH7.4. The column was washed with PBS and the bound material eluted with 0.1M Citrate pH3.5. The elution peak was collected and pH adjusted to ~pH7 with 2M Tris/HCl pH 8.5. The purification was repeated as a control using unconverted CHO. The pH neutralised Protein-A eluates were analysed by G3000 SEC-HPLC (Table 7) and SDS-PAGE under non-reducing and reducing conditions (FIGS. 11 and 12). An elution pH was found that allowed for elution of FabFv monomer while multimeric species remained bound to the column. The supernatant conversion process was repeated and applied to the 9.4 ml HiScreen columns and was eluted using elution conditions (0.1M Citrate pH 3.8). A control run of unconverted supernatant loaded at identical loading capacity was also carried out. The elution peaks were collected and pH adjusted to ~pH7 with 2M Tris/HCl pH 8.5. The pH neutralised Protein-A eluates were analysed via G3000 SEC-HPLC (FIGS. 13 and 14) analysis and A280 (Table 8). Significantly higher monomer levels were observed from the converted material with comparable recovery when eluted at pH 3.5. Product quality from both the supernatant with and without the conversion were comparable from the pH3.8 elutions when analysed via SEC-HPLC however a significant increase in the amount of protein was observed post conversion.

TABLE 7

| Sample | % Monomer | Protein (mg) |
|---|---|---|
| Protein A Elution - Post Conversion | 67.1 | 14.1 |
| Protein A Elution - No Conversion | 38.6 | 14.9 |

TABLE 8

| Sample | % Monomer | Protein (mg) |
|---|---|---|
| Protein A Elution @ pH 3.8 - Post Conversion | 97.9 | 9.0 |
| Protein A Elution @ pH 3.8 - No Conversion | 98.5 | 4.9 |

Example 3: Investigation into the Effect of Various Parameters

The feed antibody used for this experiment was A26Fab-645dsFv. All experiments were performed on Protein A purified material. A26Fab-645dsFv cell culture fluid was purified using a protein A column (MabSelect, GE-Healthcare). The material was loaded at pH 7.4, with the majority of the impurities flowing through the column while the target molecules were bound. The column was then eluted at pH 3.4, using a sodium citrate buffer. This eluted the monomeric species along with the multimeric species. The elution pool was concentrated to 13 g/L and diafiltered into PBS buffer at pH 7.4. The feed antibody A26Fab-645dsFv contained around 15% monomer pre-conversion. The concentration of the antibody (Feed Cone g/L), the pH, the bMEA reductant concentration, the temperature of the conversion step and the mixing speed were all evaluated, as shown in Table 9 below.

The Monomer, Dimer, Trimer, Quatramer and HMWS % were measured at 0.5, 1, 1.5, 2, 3, 4, 5, 6, 7 and 23 hours by SE-UPLC using a machine manufactured by Walters using column BEH200 SEC 1.7 μm and are shown in Table 10 for 5 hours.

TABLE 9

Experimental parameters for Experiments N1 to N35

| Exp Name | Feed conc. (g/L) | pH | Reductant conc. (mM) | Temperature (° C.) | Mixing (rpm) |
|---|---|---|---|---|---|
| N1 | 0.50 | 5.4 | 5 | 40 | 100 |
| N2 | 5.00 | 5.4 | 5 | 40 | 100 |
| N3 | 0.50 | 8.6 | 5 | 40 | 100 |
| N4 | 5.00 | 8.6 | 5 | 40 | 100 |
| N5 | 0.50 | 5.4 | 100 | 40 | 100 |
| N6 | 5.00 | 5.4 | 100 | 40 | 100 |
| N7 | 0.50 | 8.6 | 100 | 40 | 100 |
| N8 | 5.00 | 8.6 | 100 | 40 | 100 |
| N9 | 0.50 | 5.4 | 5 | 55 | 100 |
| N10 | 5.00 | 5.4 | 5 | 55 | 100 |
| N11 | 0.50 | 8.6 | 5 | 55 | 100 |
| N12 | 5.00 | 8.6 | 5 | 55 | 100 |
| N13 | 0.50 | 5.4 | 100 | 55 | 100 |
| N14 | 5.00 | 5.4 | 100 | 55 | 100 |
| N15 | 0.50 | 8.6 | 100 | 55 | 100 |
| N16 | 5.00 | 8.6 | 100 | 55 | 100 |
| N17 | 0.50 | 5.4 | 5 | 40 | 1200 |
| N18 | 5.00 | 5.4 | 5 | 40 | 1200 |
| N19 | 0.50 | 8.6 | 5 | 40 | 1200 |
| N20 | 5.00 | 8.6 | 5 | 40 | 1200 |
| N21 | 0.50 | 5.4 | 100 | 40 | 1200 |
| N22 | 5.00 | 5.4 | 100 | 40 | 1200 |
| N23 | 0.50 | 8.6 | 100 | 40 | 1200 |
| N24 | 5.00 | 8.6 | 100 | 40 | 1200 |
| N25 | 0.50 | 5.4 | 5 | 55 | 1200 |
| N26 | 5.00 | 5.4 | 5 | 55 | 1200 |
| N27 | 0.50 | 8.6 | 5 | 55 | 1200 |
| N28 | 5.00 | 8.6 | 5 | 55 | 1200 |
| N29 | 0.50 | 5.4 | 100 | 55 | 1200 |
| N30 | 5.00 | 5.4 | 100 | 55 | 1200 |
| N31 | 0.50 | 8.6 | 100 | 55 | 1200 |
| N32 | 5.00 | 8.6 | 100 | 55 | 1200 |
| N33 | 2.75 | 6.9 | 52.5 | 47.5 | 650 |
| N34 | 2.75 | 6.9 | 52.5 | 47.5 | 650 |
| N35 | 2.75 | 6.9 | 52.5 | 47.5 | 650 |

Table 10 results of Table 9 above at 5 hours.

| Exp Name | Feed conc. (g/L) | pH | Reductant conc. (mM) | Temperature (°C) | Mixing (rpm) | HMWS | Quatramer | Trimer | Dimer | Monomer |
|---|---|---|---|---|---|---|---|---|---|---|
| N1 | 0.50 | 5.4 | 5 | 40 | 100 | 11.1 | 13.0 | 22.8 | 28.2 | 24.6 |
| N2 | 5.00 | 5.4 | 5 | 40 | 100 | 18.7 | 16.2 | 22.7 | 24.6 | 17.9 |
| N3 | 0.50 | 8.6 | 5 | 40 | 100 | 11.4 | 14.3 | 22.2 | 27.4 | 24.8 |
| N4 | 5.00 | 8 6 | 5 | 40 | 100 | 22.3 | 16.0 | 21.9 | 23.1 | 16.7 |
| N5 | 0.50 | 5.4 | 100 | 40 | 100 | 3.6 | 6.0 | 17.5 | 33.5 | 39.5 |
| N6 | 5.00 | 5.4 | 100 | 40 | 100 | 12.9 | 11.1 | 17.4 | 29.2 | 29.5 |
| N7 | 0.50 | 8.6 | 100 | 40 | 100 | 2.7 | 6.1 | 16.9 | 34.2 | 40.2 |
| N8 | 5.00 | 8.6 | 100 | 40 | 100 | 17.4 | 12.5 | 16.8 | 25.2 | 28.1 |
| N9 | 0.50 | 5.4 | 5 | 55 | 100 | 0.0 | 1.0 | 6.6 | 30.0 | 62.4 |
| N10 | 5.00 | 5.4 | 5 | 55 | 100 | 0.0 | 6.7 | 17.2 | 36.1 | 40.0 |
| N11 | 0.50 | 8.6 | 5 | 55 | 100 | 0.0 | 0.0 | 7.9 | 31.0 | 61.1 |
| N12 | 5.00 | 8.6 | 5 | 55 | 100 | 2.7 | 5.7 | 18.1 | 34.3 | 38.8 |
| N13 | 0.50 | 5.4 | 100 | 55 | 100 | 0.0 | 0.0 | 0.3 | 3.5 | 95.7 |
| N14 | 5.00 | 5.4 | 100 | 55 | 100 | 0.0 | 0.0 | 0.7 | 10.8 | 88.6 |
| N15 | 0.50 | 8.6 | 100 | 55 | 100 | 0.0 | 0.0 | 0.1 | 3.5 | 96.5 |
| N16 | 5.00 | 8.6 | 100 | 55 | 100 | 0.0 | 0.8 | 1.6 | 13.9 | 83.6 |
| N17 | 0.50 | 5.4 | 5 | 40 | 1200 | 7.7 | 10.0 | 19.2 | 31.2 | 32.0 |
| N18 | 5.00 | 5.4 | 5 | 40 | 1200 | 13.9 | 15.1 | 23.6 | 27.1 | 20.3 |
| N19 | 0.50 | 8.6 | 5 | 40 | 1200 | 8.4 | 11.1 | 21.3 | 30.8 | 28.5 |
| N20 | 5.00 | 8.6 | 5 | 40 | 1200 | 20.0 | 15.2 | 22.5 | 24.4 | 18.0 |
| N21 | 0.50 | 5.4 | 100 | 40 | 1200 | 0.0 | 5.6 | 15.9 | 36.2 | 42.3 |
| N22 | 5.00 | 5.4 | 100 | 40 | 1200 | 12.6 | 10.3 | 16.4 | 30.0 | 30.8 |
| N23 | 0.50 | 8.6 | 100 | 40 | 1200 | 2.2 | 5.5 | 17.3 | 35.1 | 39.9 |
| N24 | 5.00 | 8.6 | 100 | 40 | 1200 | 14.4 | 11.7 | 16.7 | 26.6 | 30.6 |
| N25 | 0.50 | 5.4 | 5 | 55 | 1200 | 0.0 | 0.0 | 6.7 | 32.0 | 61.3 |
| N26 | 5.00 | 5.4 | 5 | 55 | 1200 | 2.1 | 5.7 | 18.7 | 36.2 | 37.3 |
| N27 | 0.50 | 8.6 | 5 | 55 | 1200 | 0.0 | 1.1 | 8.1 | 31.6 | 59.2 |
| N28 | 5.00 | 8.6 | 5 | 55 | 1200 | 1.7 | 4.9 | 17.2 | 35.6 | 40.7 |
| N29 | 0.50 | 5.4 | 100 | 55 | 1200 | 0.0 | 0.0 | 2.4 | 11.6 | 86.0 |
| N30 | 5.00 | 5.4 | 100 | 55 | 1200 | 0.0 | 0.0 | 1.6 | 13.1 | 75.5 |
| N31 | 0.50 | 8.6 | 100 | 55 | 1200 | 0.0 | 0.0 | 0.0 | 3.9 | 96.1 |
| N32 | 5.00 | 8.6 | 100 | 55 | 1200 | 0.0 | 0.0 | 1.3 | 14.9 | 83.9 |
| N33 | 2.75 | 6.9 | 52.5 | 47.5 | 650 | 1.4 | 2.7 | 9.6 | 30.6 | 55 6 |
| N34 | 2.75 | 6.9 | 52.5 | 47.5 | 650 | 2.8 | 3.6 | 11.6 | 30 5 | 51.6 |
| N35 | 2.75 | 6.9 | 52.5 | 47.5 | 650 | 2.4 | 3.4 | 11.0 | 30.3 | 53.0 |

The aim of the conversion step is to maximise the % monomer percentage. Across the ranges investigated the most significant factors in the model on the % monomer are reductant concentration and temperature. At higher reductant concentrations and at higher temperatures the % monomer increased.

There was a trend observed that there was a correlation between increase in temperature and degree of precipitation.

Example 4: Investigation into the Effect of Various Excipients

The excipients and concentrations investigated in the experiment are provided in Table 11 below:

| Glycine mM | Serine mM | Proline mM v/v) | Alanine mM v/v) | Lysine M) | Arginine mM M) | Polysorbate 80 | Polysorbate (2% | AmmS te 20 2% ul | NaCl (4 t (1.5 |
|---|---|---|---|---|---|---|---|---|---|
| 0 | 0 | 0 | 0 | 0.0 | 0 | 0 | 0 | 0 | 0 |
| 11 | 11 | 11 | 17 | 11 | 17 | 0.4 | 0.4 | 667 | 167 |
| 22 | 22 | 22 | 33 | 22 | 33 | 0.7 | 0.7 | 778 | 250 |
| 56 | 56 | 56 | 83 | 56 | 83 | 0.9 | 0.9 | 889 | 333 |
| 111 | 111 | 111 | 167 | 111 | 167 | 0.1 | 0.1 | 1000 | 417 |
| 278 | 278 | 278 | 333 | 278 | 333 | 0.2 | 0.2 | 1111 | 500 |
| 556 | 556 | 556 | 583 | 556 | 583 | 0.6 | 0.6 | 1222 | 667 |
| 778 | 778 | 778 | 833 | 778 | 833 | 1.1 | 1.1 | 1556 | 833 |

Concentrations are shown in mM, except polysorbate 20 and 80, which are shown as percentage v/v. Experiments were performed in 2 mL deep well plates and were completed in duplicate. The conditions used were 0.5 g/L A26Fab-dsFv, 100 mM β-mea, the excipients listed in table 11 and a temperature of 55° C. 10 control samples were also performed using 0.5 g/L A26Fab-dsFv, 100 mM β-mea, 55° C. without excipients. A further 6 controls were performed with A26Fab-dsFv at 0.5 g/L, a temperature of 55° C. without reductant and without excipients.

Timecourse samples were taken at regular intervals. The Bradford assay was used to monitor the yield. The Bradford protein assay is an analytical procedure used to measure the concentration of protein in a solution. It was found that the β-mea did not absorb at 595 nm. Thus, this method was used to measure the total protein concentration and therefore to determine the step yield. Total protein concentration was determined by using the Bradford protein assay kit in a 96 well format with liquid transfer performed using a Tecan Freedom EVO 200 (Tecan, Reading, UK) liquid handling robot. The assay was calibrated with purified A26Fab-645dsFv material, tested orthogonally by A280 nm. Samples were prepared and analysed as per the manufacturer's instructions. Unknown concentrations were then determined by interpolation from the curve by linear regression.

Figure 15:
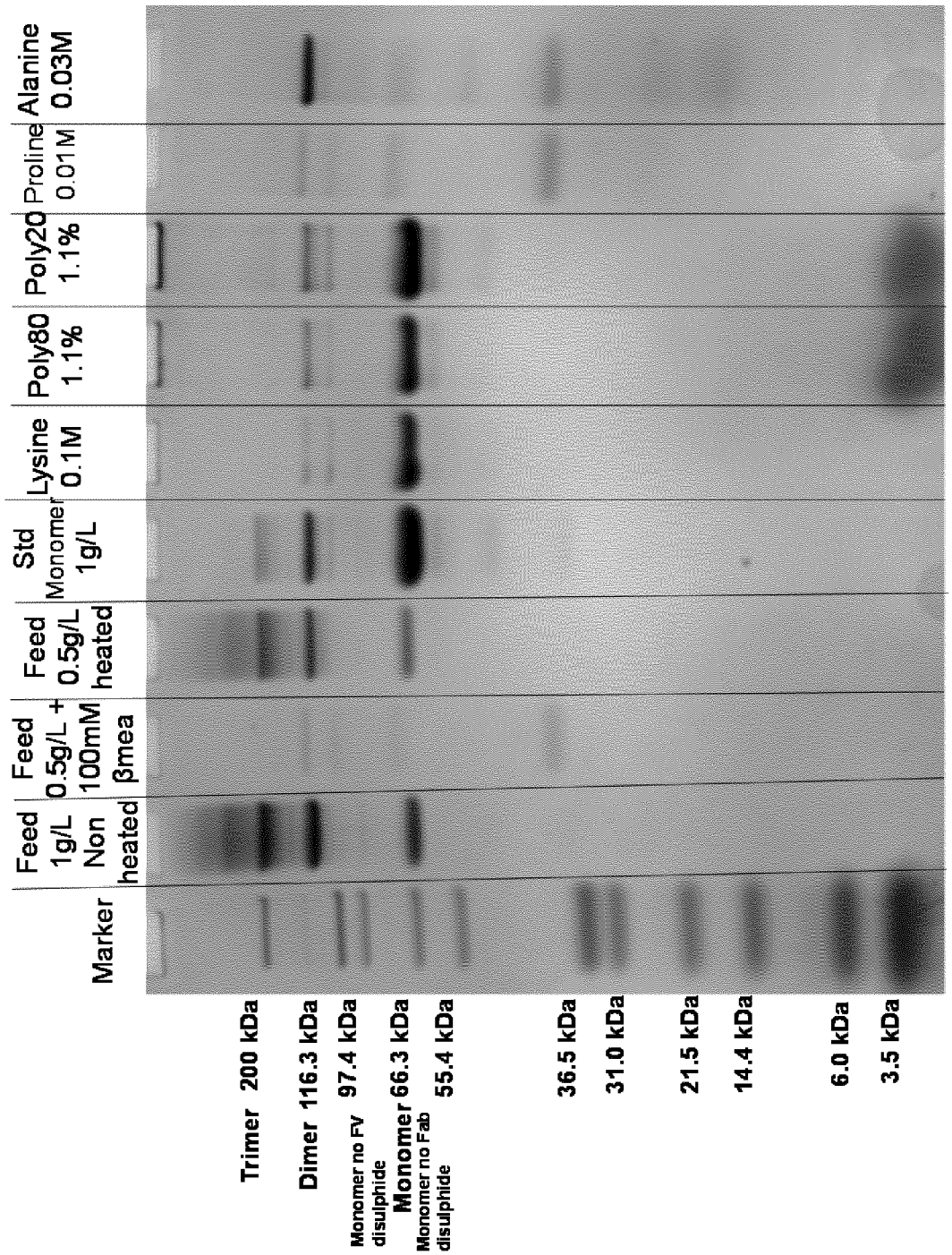
FIG. 15 shows a non-reducing SDS page for A26Fab-645dsFv antibody treated with various excipients.
Figure 16A:
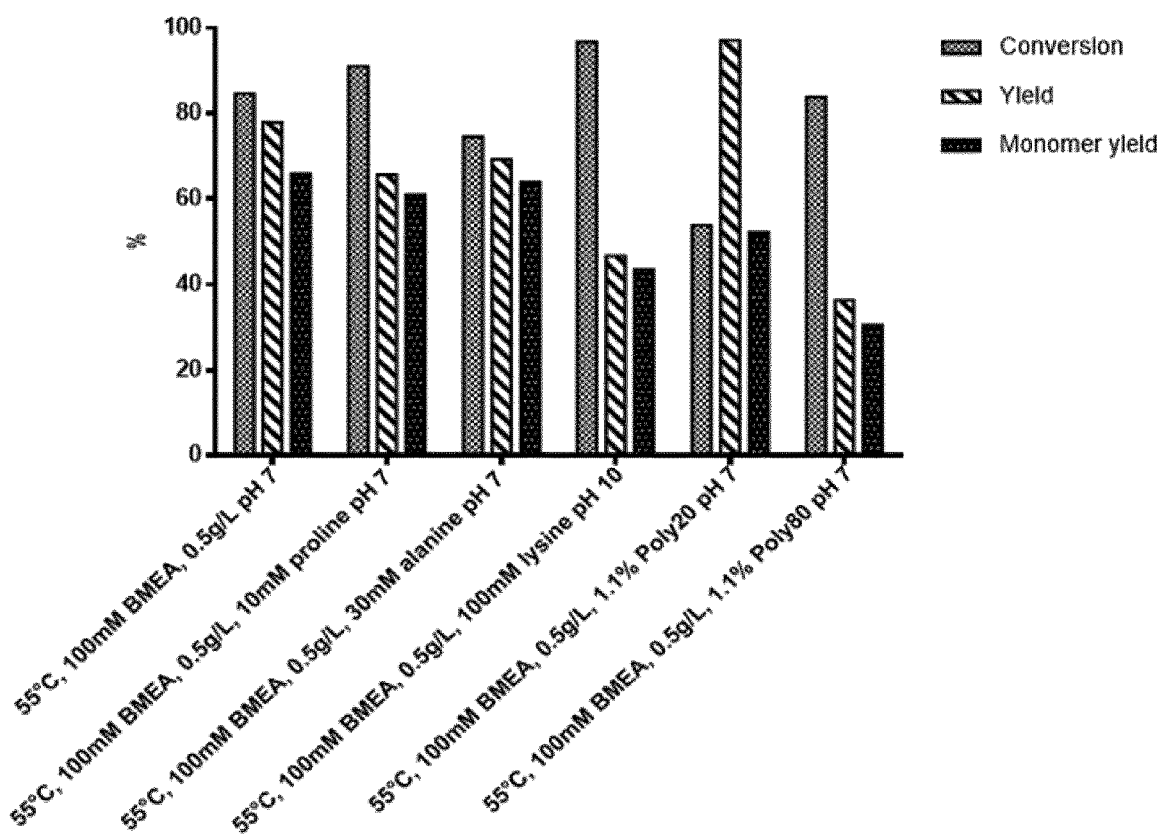
FIGS. 16a and 16b show size exclusion chromatography data for A26Fab-645dsFv after processing under different conditions.
Figure 16B:
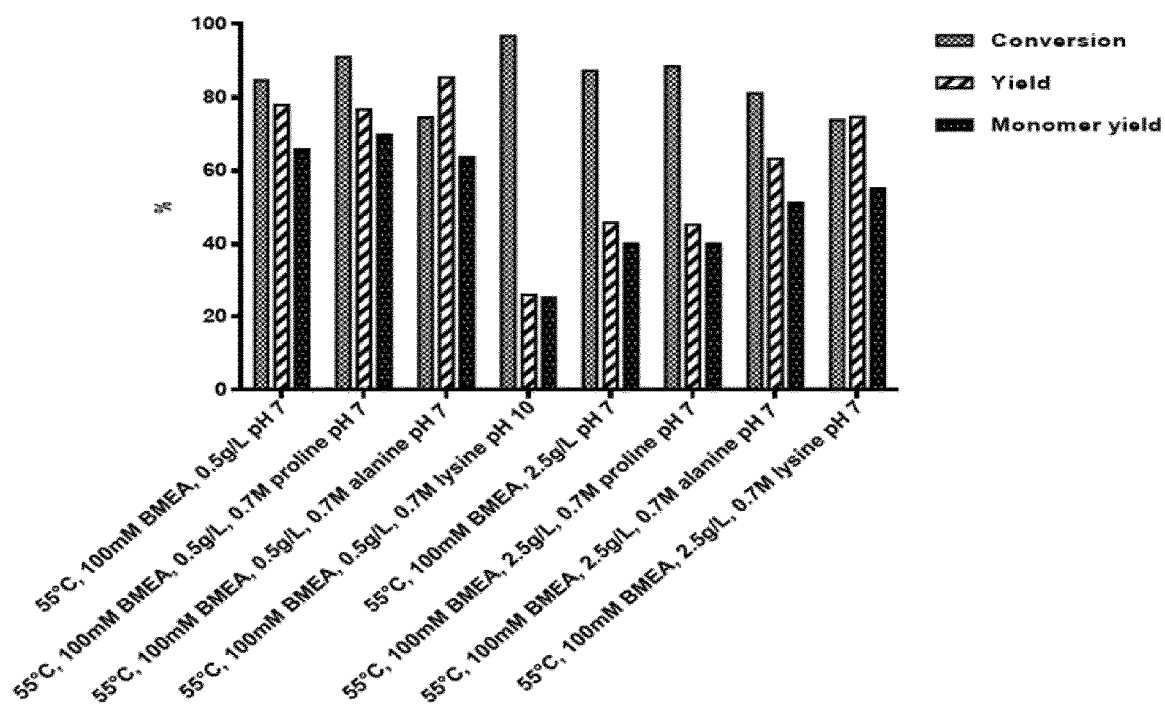

Any experiments with high yields were subsequently analysed by SE-UPLC and SDS PAGE. Amino acids seemed to reduce precipitation since they increased the yield compared to the control. For the polysorbates, further analysis by SDS PAGE was performed to analyse their effect (FIG. 15), samples were from the second screening, with 0.5 g/L feed, 100 mM βMEA at 55° C., after 5 h. FIGS. 16a and 16b show size exclusion data for various excipients under different conditions.

Example 5: Investigation of Parameters in Combination with Lysine

The antibody feed concentration g/L bMEA concentration and temperature parameters were investigate in the presence of 0.7M lysine and in the absence of lysine. Experiments were performed in 2 mL deep well plates and were completed in duplicate. 2 mL Eppendorf tubes were used and each conversion step was carried out for 5 hours in a water bath.

TABLE 12

Alternative experimental design to investigate factors, ranges and response

| Exp Name | Feed Conc. (g/L) | β-mea conc. (mM) | Temperature (° C.) |
|---|---|---|---|
| N1 | 0.50 | 50 | 50 |
| N2 | 5.00 | 50 | 50 |
| N3 | 0.50 | 100 | 50 |
| N4 | 5.00 | 100 | 50 |

TABLE 12-continued

Alternative experimental design to investigate factors, ranges and response

| Exp Name | Feed Conc. (g/L) | β-mea conc. (mM) | Temperature (° C.) |
|---|---|---|---|
| N5 | 0.50 | 50 | 55 |
| N6 | 5.00 | 50 | 55 |
| N7 | 0.50 | 100 | 55 |
| N8 | 5.00 | 100 | 55 |
| N9 | 0.50 | 75 | 53 |
| N10 | 5.00 | 75 | 53 |
| N11 | 2.75 | 50 | 53 |
| N12 | 2.75 | 100 | 53 |
| N13 | 2.75 | 75 | 50 |
| N14 | 2.75 | 75 | 55 |
| N15 | 2.75 | 75 | 53 |
| N16 | 2.75 | 75 | 53 |
| N17 | 2.75 | 75 | 53 |

TABLE 13 Results for Table 12 Above without Lysine

| Exp Name | Feed Conc. (g/L) | 13-mea conc. (mM) | Temperature (?+0C) | % Monomer | cyo Yield | cyo Monomer |
|---|---|---|---|---|---|---|
| Ni | 0.50 | 50 | 50.0 | 74.2 | 80.2 | 59.5 |
| N2 | 5.00 | 50 | 50.0 | 69.0 | 78.2 | 53.9 |
| N3 | 0.50 | 100 | 50.0 | 85.8 | 71.6 | 61.4 |
| N4 | 5.00 | 100 | 50.0 | 75.7 | 61.1 | 46.2 |
| N5 | 0.50 | 50 | 55.0 | 90.0 | 27.1 | 24.4 |
| N6 | 5.00 | 50 | 55.0 | 81.8 | 5.8 | 4.7 |
| N7 | 0.50 | 100 | 55.0 | 83.3 | 7.8 | 6.5 |
| N8 | 5.00 | 100 | 55.0 | 69.6 | 1.4 | 1.0 |
| N9 | 0.50 | 75 | 52.5 | 92.7 | 42.4 | 39.3 |
| N10 | 5.00 | 75 | 52.5 | 82.9 | 14.4 | 12.0 |
| N11 | 2.75 | 50 | 52.5 | 85.7 | 42.8 | 36.7 |
| N12 | 2.75 | 100 | 52.5 | 85.5 | 13.9 | 11.9 |
| N13 | 2.75 | 75 | 50.0 | 78.8 | 82.3 | 64.9 |
| N14 | 2.75 | 75 | 55.0 | 77.2 | 3.8 | 2.9 |
| N15 | 2.75 | 75 | 52.5 | 86.9 | 24.3 | 21.1 |
| N16 | 2.75 | 75 | 52.5 | 86.8 | 24.3 | 21.1 |
| N17 | 2.75 | 75 | 52.5 | 86.1 | 25.3 | 21.8 |

TABLE 14 Results for Table 12 Above with 0.7M Lysine

| Exp Name | Feed Conc. (g/L) | 13-mea conc. (mM) | Temperature (?+0C) | Yield Monomer | % Yield | cyo Monomer | cyo Yield |
|---|---|---|---|---|---|---|---|
| Ni | 0.50 | 50.00 | 50.00 | 47.7 | 86.0 | 41.0 | |
| N2 | 5.00 | 50.00 | 50.00 | 58.6 | 91.7 | 53.7 | |
| N3 | 0.50 | 100.00 | 50.00 | 59.7 | 82.6 | 49.3 | |
| N4 | 5.00 | 100.00 | 50.00 | 67.4 | 84.5 | 57.0 | |
| N5 | 0.50 | 50.00 | 55.00 | 87.9 | 50.4 | 44.3 | |
| N6 | 5.00 | 50.00 | 55.00 | 82.3 | 29.7 | 24.4 | |
| N7 | 0.50 | 100.00 | 55.00 | 92.7 | 23.5 | 21.8 | |
| N8 | 5.00 | 100.00 | 55.00 | 87.4 | 9.8 | 8.6 | |
| N9 | 0.50 | 75.00 | 52.50 | 80.6 | 64.3 | 51.8 | |
| N10 | 5.00 | 75.00 | 52.50 | 78.6 | 51.1 | 40.2 | |
| N11 | 2.75 | 50.00 | 52.50 | 76.2 | 76.5 | 58.3 | |
| N12 | 2.75 | 100.00 | 52.50 | 84.3 | 48.6 | 41.0 | |
| N13 | 2.75 | 75.00 | 50.00 | 63.9 | 99.0 | 63.2 | |
| N14 | 2.75 | 75.00 | 55.00 | 88.4 | 22.0 | 19.5 | |
| N15 | 2.75 | 75.00 | 52.50 | 81.5 | 61.9 | 50.5 | |
| N16 | 2.75 | 75.00 | 52.50 | 81.4 | 61.0 | 49.7 | |
| N17 | 2.75 | 75.00 | 52.50 | 82.4 | 60.3 | 49.7 | |

When 0.7M lysine was present, temperature had the strongest effect on % monomer, with more seen at higher temperatures.

Example 6: Investigation of Different Reducing Agents

For the initial reductant screening experiment we used a temperature of 50° C. to open up the molecule. The feed was purified A26Fab-dsFv, concentration 1 g/L and 15% monomer. The experiment was performed in Eppendorfs with a feed volume of 1 mL. The reductant concentrations screened were 10, 50 and 100 mM (Table 15).

The samples were heated and mixed using a Vortemp instrument from Thermo Scientific. Sampling was performed after the addition of the reductant but before heating, and after 2 h of heating at 50° C. β-mea was used as the control reductant for this experiment.

TABLE 15

Initial reductant and conditions investigated

| REDUCTANT | CONC. TESTED mM | TEMP ° C. | FEED CONC. | MIXING SPEED |
|---|---|---|---|---|
| TCEP | 10, 50 and 100 | 50 | 1 g/L | 1200 rpm |
| DTT | 10, 50 and 100 | 50 | 1 g/L | 1200 rpm |
| Phosphorous acid | 10, 50 and 100 | 50 | 1 g/L | 1200 rpm |
| Ascorbic acid | 10, 50 and 100 | 50 | 1 g/L | 1200 rpm |
| Methyl Sulfate sodium | 10, 50 and 100 | 50 | 1 g/L | 1200 rpm |
| Ethylene sulfite | 10, 50 and 100 | 50 | 1 g/L | 1200 rpm |

Figure 17A:
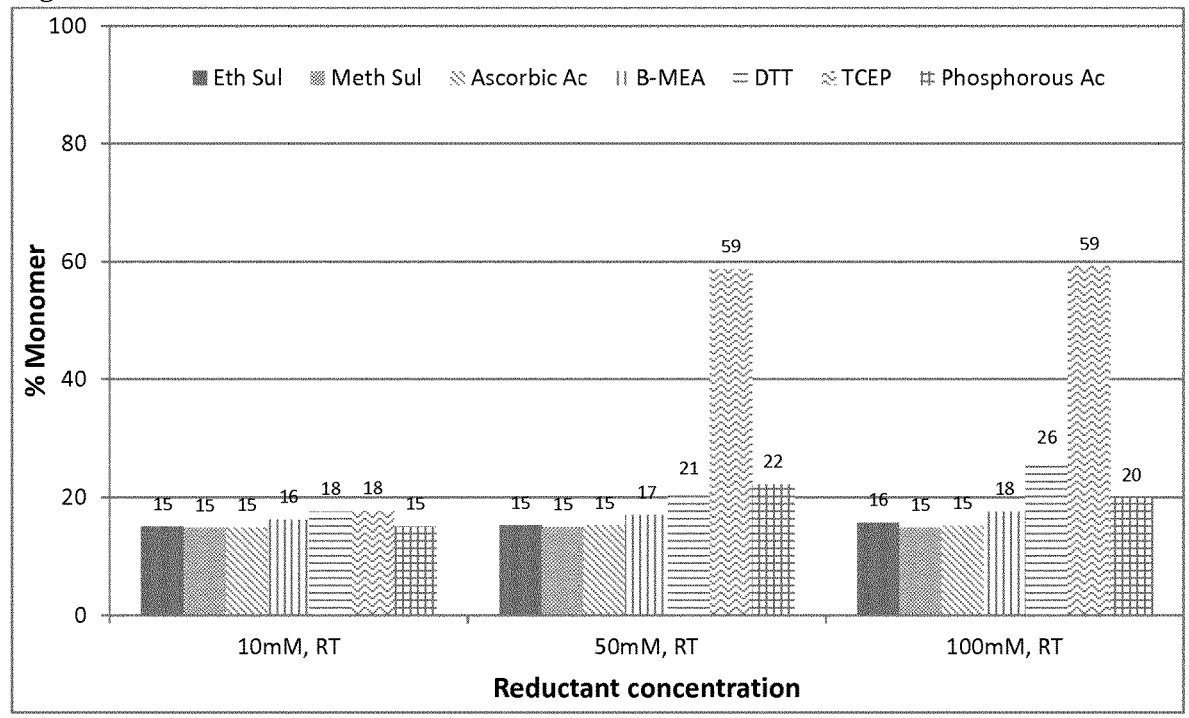
FIG. 17a show the percentage monomer after treatment with a reducing agent at room temperature.
Figure 17B:
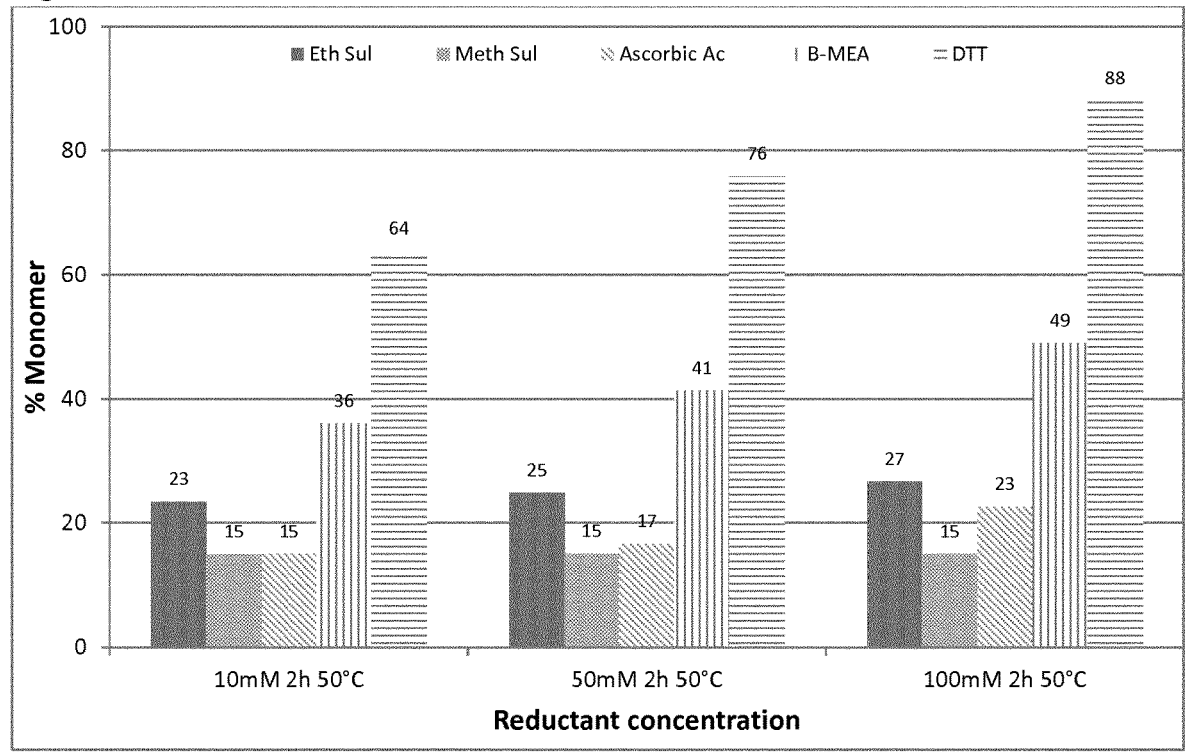
FIG. 17b shows the percentage monomer after treatment with a reducing agent for 2 hours at 50° C.

The yield was calculated using the peak area on the SE UPLC assay. The total peak area of the sample was divided by the total peak area of the feed material. The monomer yield was calculated by multiplying the percentage monomer by the total yield. FIG. 17a show the % monomer when the treatment was performed at room temperature and the FIG. 17b shows the results after 2 hours for corresponding experiments performed at 50° C.

Figure 18A:
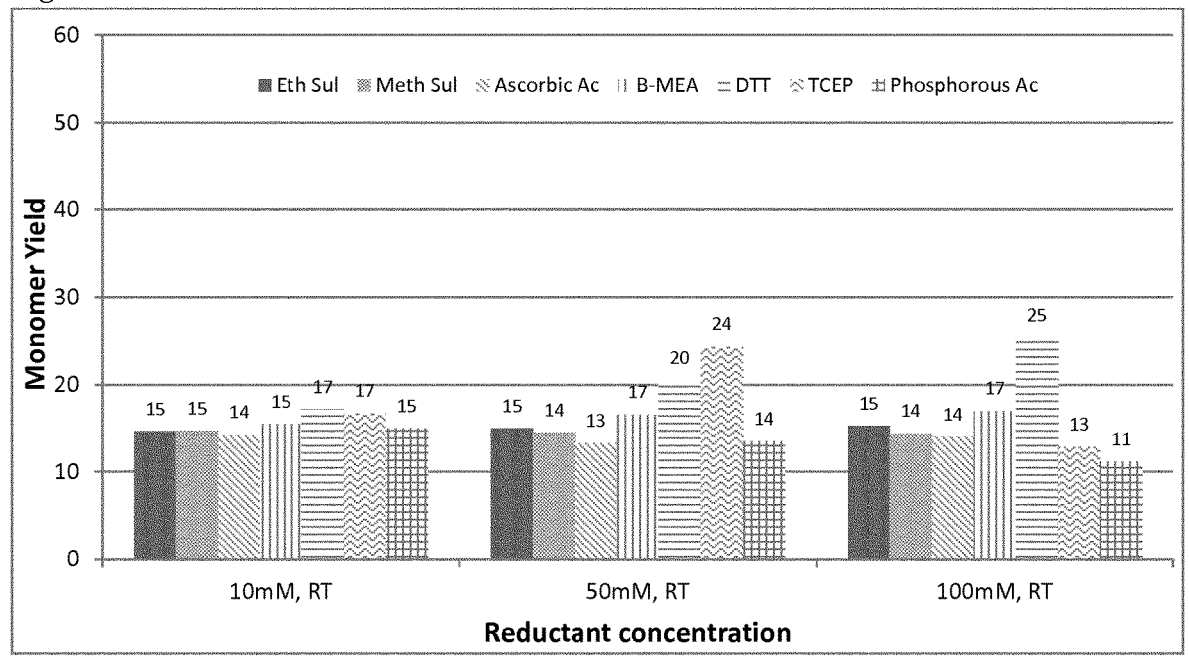
FIG. 18a shows the percentage monomer as analysed by SE-HPLC after treatment with a reducing agent at room temperature.
Figure 18B:
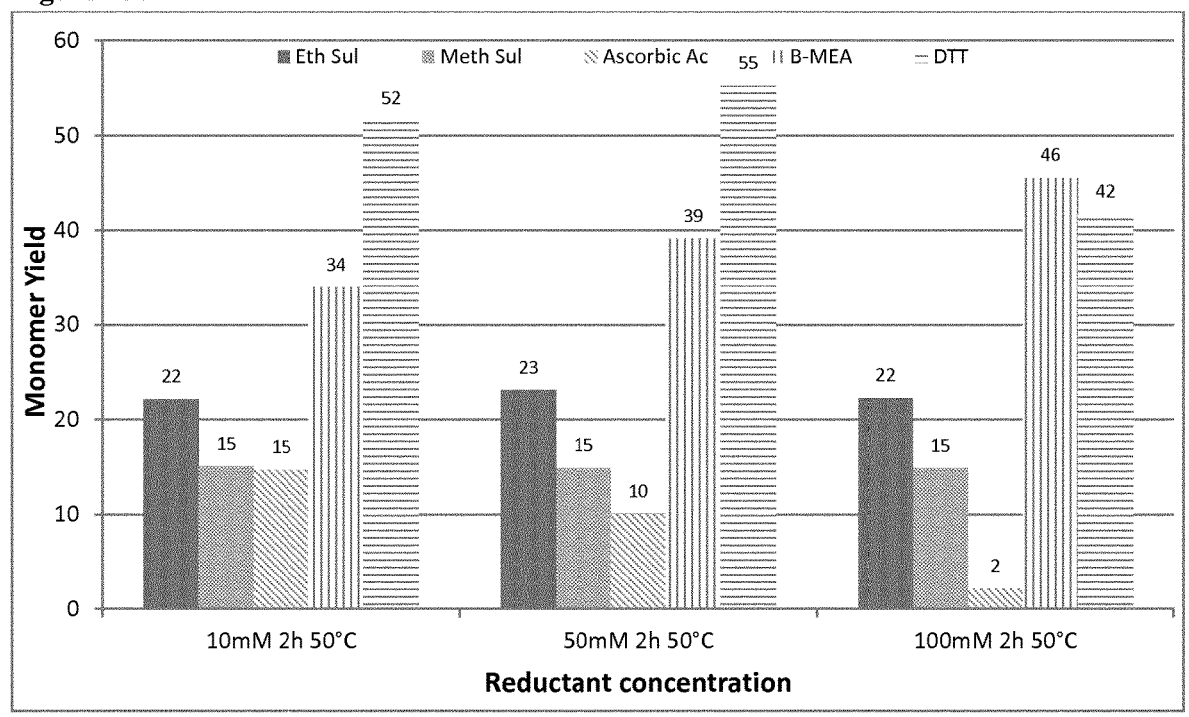
FIG. 18b shows the percentage monomer as analysed by SE-HPLC after treatment with a reducing agent for 2 hours at 50° C.

FIGS. 18a and 18b show the results of a corresponding analysis performed by SE-HPLC.

Example 7: Conversion at 2 L Scale

CHO expression and clarification of A26Fab-645dsFv was carried out as in Example 1 to provide clarified culture fluid as the feed for the 2 L scale experiment. A thermal conversion experiment was performed in 2 L fermentation vessels, using a conversion volume of 2 L. The feed for the experiment was clarified cell culture fluid (CCF), the concentration of product was 2.2 g/L, of which 30% was monomer. The experimental conditions are shown in table 16, the conversion step was performed for 17 h in all experiments. The samples were analyzed by SE UPLC.

TABLE 16

Experimental conditions for 2 L conversion experiments

| pH | Heat (° C.) | β-mea conc. (mM) |
|---|---|---|
| 7 | 50 | 50 |

Table 17: Experimental results for 2L conversion experiments

| CCF Titre (g/L) | Load Ab load (g) | Pre Conversion % Monomer (g) | CCF Monomer load (g) | Post Titre (g/L) | Conversion Ab recovered (g) | Ab Yield recover | % Monomer | Monomer recover | Monomer yield (%) |
|---|---|---|---|---|---|---|---|---|---|
| 2.04 | 4.4 | 30.2 | 1.33 | 1.73 | 3.73 | 84.8 | 50.9 | 1.90 | 142.9 |

It was possible to scale up the conversion step to 2 L scale, in vessels representative of those used at manufacturing scale. It was possible to significantly increase the amount of monomer across the step.

The invention claimed is:

1. A method for increasing the percentage of Fab-dsFv monomer in a composition of recombinantly expressed antibody wherein the Fab-dsFv monomer comprises at least one Fv with specificity for an antigen of interest comprising one VH and one VL wherein said VH and VL are connected directly or indirectly via one or more linkers and are stabilised by a disulfide bond therebetween, said method comprising a thermal conversion step of holding the composition comprising the recombinantly expressed antibody at a temperature in the range 45 to 55° C. for a period of at least 1 hour in the presence of a reducing agent or after treatment with a reducing agent, wherein the reducing agent is selected from 2-mercaptoethanol (BME) and 2-mercaptoethylamine (BMEA) and the reducing agent is present at a concentration of 1 mM to 100 mM and wherein the intra-chain disulfide bonds in the Fab and the Fv of Fab-dsFv are not reduced.

2. The method according to claim 1, wherein the temperature is 50° C.

3. The method according to claim 1, wherein the period is in the range 1 to 70 hours.

4. The method according to claim 1, wherein the method is performed at a temperature in the range 45 to 55° C. for a period of 4 to 6 hours and the reducing agent is at a concentration in the range 60 to 90 mM.

5. The method according to claim 1, wherein the method is performed at a temperature of 50° ° C. for a period of 5 hours and the reducing agent is at a concentration 70 to 80 mM.

6. The method according to claim 1, wherein the reducing agent is employed in the presence of lysine.

7. The method according claim 6, wherein the concentration of amino acid is in the range 0.01 to 1.0 M.

8. The method according to claim 1, wherein the antibody is at a concentration in the range 0.5 g/L to 5 g/L in the composition.

9. The method according to claim 1, wherein the thermal step is performed in the presence of concomitant stirring.

10. The method according to claim 9, wherein the stirring in the range 100 to 1200 rpm.

11. The method according to claim 1, wherein reducing agent is added to the recombinant antibody composition before the temperature is raised to 45 to 55° C.

12. The method according to claim 1, wherein reducing agent is added to the recombinant antibody composition after the temperature is raised to 45 to 55° C.

13. The method according to claim 1, comprising a further step of downstream purification.

14. The method according to claim 13, wherein said downstream purification comprises chromatography.

15. The method according to claim 14, wherein the chromatography is hydrophobic interaction chromatography.

16. The method according to claim 14, wherein the chromatography is ion exchange chromatography.

17. The method according to claim 1, wherein the VH and VL which are connected directly or indirectly via one or more linkers and are stabilised by a disulfide bond therebetween are a complementary VH/VL pair which form an antigen binding site.

18. The method according to claim 1, wherein the VH and VL are connected directly via a linker or each VH and VL comprise a linker which indirectly connects the VH and VL via a second antibody.

19. The method according to claim 18, wherein each VH and VL comprise a linker which indirectly connects the VH and VL via a second antibody.

20. The method according to claim 1, wherein the recombinantly expressed antibody is a bispecific antibody fusion protein which binds human OX40 and human serum albumin comprising:
- a heavy chain comprising, in sequence from the N-terminal, a first heavy chain variable domain ($V_H1$), a $C_H1$ domain and a second heavy chain variable domain ($V_H2$),
- a light chain comprising, in sequence from the N-terminal, a first light chain variable domain ($V_L1$), a $C_L$ domain and a second light chain variable domain ($V_L2$),
- wherein said heavy and light chains are aligned such that $V_H1$ and $V_L1$ form a first antigen binding site and $V_H2$ and $V_L2$ form a second antigen binding site,
- wherein the antigen bound by the first antigen binding site is human OX40 and the antigen bound by the second antigen binding site is human serum albumin; and
- wherein the first heavy chain variable domain ($V_H1$) comprises the sequence given in SEQ ID NO:1 for CDR-H1, the sequence given in SEQ ID NO:2 for CDR-H2 and the sequence given in SEQ ID NO:3 for CDR-H3 and the first light chain variable domain ($V_L1$) comprises the sequence given in SEQ ID NO:4 for CDR-L1, the sequence given in SEQ ID NO:5 for CDR-L2 and the sequence given in SEQ ID NO:6 for CDR-L3,
- wherein the second heavy chain variable domain ($V_H2$) has the sequence given in SEQ ID NO:11 and the second light chain variable domain ($V_L2$) has the sequence given in SEQ ID NO: 12 and
- the second heavy chain variable domain ($V_H2$) and second light chain variable domain ($V_L2$) are linked by a disulfide bond.

21. The method according to claim 1, wherein the composition of recombinantly expressed antibody molecules is a clarified supernatant.

22. The method according to claim 1, wherein, prior to the thermal conversion step, the method further comprises a step of protein A chromatography to remove impurities from the composition.

* * * * *

UNITED STATES PATENT AND TRADEMARK OFFICE
CERTIFICATE OF CORRECTION

PATENT NO.         : 10,829,565 B2
APPLICATION NO.    : 15/568018
DATED              : November 10, 2020
INVENTOR(S)        : Sam Philip Heywood et al.

It is certified that error appears in the above-identified patent and that said Letters Patent is hereby corrected as shown below:

In the Specification

Column 14,
Line 24, "or a dsseFv dsscFv" should read --or a dsscFv;--.

Column 18,
Line 4, "131 integrins" should read --β1 integrins--.

Column 28,
Line 40, "50l of Novex" should read --50µl of Novex--.

Column 29,
Lines 19-26,

"
| Table 1 Time | Total Monomer (hours) | - Conversion | with | 50mM | bMEA | | | |
|---|---|---|---|---|---|---|---|---|
| 0 | 0.5 | 1 | 2 | 3 | 4 | 5 | 20 | 44 |
| 37?+0C | 27.6 | 28.37 | 29.49 | 30.85 | 31.98 | 32.86 | 33.63 | 40.09 |
| 45?+0C | 27.6 | 29.46 | 31.12 | 33.51 | 35.62 | 37.39 | 39.11 | 53.00 | 61.01 |
| 50?+0C | 27.6 | 31.48 | 35.95 | 42.18 | 47.2 | 50.6 | 52.98 | 70.84 | 74.29 |
| 55?+0C | 27.6 | 35.94 | 44.49 | 56.76 | 64.04 | 68.71 | 72.68 | 85.74 | |
| 60?+0C | 27.6 | 72.03 | 78.79 | 81.92 | | | | | |
"

should read

Signed and Sealed this
Twenty-fourth Day of August, 2021

Drew Hirshfeld
*Performing the Functions and Duties of the*
*Under Secretary of Commerce for Intellectual Property and*
*Director of the United States Patent and Trademark Office*

Table 1  Total Monomer - Conversion with 50mM bMEA

|  | Time (hours) | | | | | | | | |
| --- | --- | --- | --- | --- | --- | --- | --- | --- | --- |
|  | 0 | 0.5 | 1 | 2 | 3 | 4 | 5 | 20 | 44 |
| 37°C | 27.6 | 28.37 | 29.49 | 30.85 | 31.98 | 32.86 | 33.63 | 40.09 |  |
| 45°C | 27.6 | 29.46 | 31.12 | 33.51 | 35.62 | 37.39 | 39.11 | 53.00 | 61.01 |
| 50°C | 27.6 | 31.48 | 35.95 | 42.18 | 47.2 | 50.6 | 52.98 | 70.84 | 74.29 |
| 55°C | 27.6 | 35.94 | 44.49 | 56.76 | 64.04 | 68.71 | 72.68 | 85.74 |  |
| 60°C | 27.6 | 72.03 | 78.79 | 81.92 |  |  |  |  |  |

--.

Column 29,
Lines 30-37,

"
Table 2  Predicted Yield - Conversion with 50mM  bMEA
Time     (hours)
0        0.5                    1        2      3      4      5      20     44
37?+0C   100.0                  100.1    100.3  100.0  99.3   99.4   99.9   100.8
45?+0C   100.0                  99.5     99.4   100.7  100.1  99.7   101.0  99.6   99.3
50?+0C   100.0                  99.8     98.5   97.5   95.7   94.7   95.4   86.8   87.0
55?+0C   100.0                  100.4    95.6   86.3   80.0   76.1   72.9   55.8
60?+0C   100.0                  57.3     50.6   44.1
"

should read

Table 2  Predicted Yield – Conversion with 50mM bMEA

|  | Time (hours) | | | | | | | | |
| --- | --- | --- | --- | --- | --- | --- | --- | --- | --- |
|  | 0 | 0.5 | 1 | 2 | 3 | 4 | 5 | 20 | 44 |
| 37°C | 100.0 | 100.1 | 100.3 | 100.0 | 99.3 | 99.4 | 99.9 | 100.8 |  |
| 45°C | 100.0 | 99.5 | 99.4 | 100.7 | 100.1 | 99.7 | 101.0 | 99.6 | 99.3 |
| 50°C | 100.0 | 99.8 | 98.5 | 97.5 | 95.7 | 94.7 | 95.4 | 86.8 | 87.0 |
| 55°C | 100.0 | 100.4 | 95.6 | 86.3 | 80.0 | 76.1 | 72.9 | 55.8 |  |
| 60°C | 100.0 | 57.3 | 50.6 | 44.1 |  |  |  |  |  |

--.

Column 29,
Lines 42-48,

"
Table 3  Net Recovery -        Conversion with 50mM  bMEA
Time     (hours)
0        0.5           1        2        3        4      5       20     44
37?+0C   27.6          28.4     29.6     30.9     31.8   32.7    33.6   40.4
45?+0C   27.6          29.3     30.9     33.7     35.7   37.3    39.5   52.8   60.6
50?+0C   27.6          31.41    35.41    41.14    45.16  47.94   50.52  61.5   64.7
55?+0C   27.6          36.08    42.52    48.97    51.3   52.27   52.99  47.86
60?+0C   27.6          41.3     39.85    36.14
"

should read

Table 3   Net Recovery – Conversion with 50mM bMEA

|       | Time (hours) | | | | | | | | |
|-------|---|-----|-----|-----|-----|-----|-----|-----|------|
|       | 0 | 0.5 | 1 | 2 | 3 | 4 | 5 | 20 | 44 |
| 37°C | 27.6 | 28.4 | 29.6 | 30.9 | 31.8 | 32.7 | 33.6 | 40.4 | |
| 45°C | 27.6 | 29.3 | 30.9 | 33.7 | 35.7 | 37.3 | 39.5 | 52.8 | 60.6 |
| 50°C | 27.6 | 31.41 | 35.41 | 41.14 | 45.16 | 47.94 | 50.52 | 61.5 | 64.7 |
| 55°C | 27.6 | 36.08 | 42.52 | 48.97 | 51.3 | 52.27 | 52.99 | 47.86 | |
| 60°C | 27.6 | 41.3 | 39.85 | 36.14 | | | | | |

Column 31,
Lines 1-9,

```
Table 4      Total
Monomer      - Conversion at 50?+0C and stated
bMEA         concentration
Time (hours)
0            1.5                5        21      28       47
1mM bMEA  27.6                 27.8     28.2    30.1    30.3    31.0
5mM bMEA  27.6                 29.7     33.4    40.0    41.4    42.8
10mM bMEA 27.6                 32.3     39.2    49.2    51.1    54.2
20mM bMEA 27.6                 35.3     44.0    59.1    61.7    66.1
50mM bMEA 27.6                 41.1     52.9    74.7    76.7    79.4
```
"

should read

Table 4   Total Monomer - Conversion at 50°C and stated bMEA concentration

|            | Time (hours) | | | | | |
|------------|------|------|------|------|------|------|
|            | 0 | 1.5 | 5 | 21 | 28 | 47 |
| 1mM bMEA  | 27.6 | 27.8 | 28.2 | 30.1 | 30.3 | 31.0 |
| 5mM bMEA  | 27.6 | 29.7 | 33.4 | 40.0 | 41.4 | 42.8 |
| 10mM bMEA | 27.6 | 32.3 | 39.2 | 49.2 | 51.1 | 54.2 |
| 20mM bMEA | 27.6 | 35.3 | 44.0 | 59.1 | 61.7 | 66.1 |
| 50mM bMEA | 27.6 | 41.1 | 52.9 | 74.7 | 76.7 | 79.4 |

Column 31,
Lines 11-20,

```
Table 5      Predicted   Yield - Conversion at 50?+0C and stated bMEA concentration
Time         (hours)
0            1.5         5                   21              28      47
1mM bMEA  100.0         99.8                99.4            99.3    98.6    98.7
5mM bMEA  100.0         99.8                98.9            97.8    98.4   100.4
10mM bMEA 100.0         99.3                98.4            96.3    95.0    95.2
20mM bMEA 100.0         97.6                95.8            93.3    92.3    91.0
50mM bMEA 100.0         98.0                93.8            85.4    84.7    81.9
```
"

should read

Table 5    Predicted Yield - Conversion at 50°C and stated bMEA concentration

|  | Time (hours) | | | | | |
| --- | --- | --- | --- | --- | --- | --- |
|  | 0 | 1.5 | 5 | 21 | 28 | 47 |
| 1mM bMEA | 100.0 | 99.8 | 99.4 | 99.3 | 98.6 | 98.7 |
| 5mM bMEA | 100.0 | 99.8 | 98.9 | 97.8 | 98.4 | 100.4 |
| 10mM bMEA | 100.0 | 99.3 | 98.4 | 96.3 | 95.0 | 95.2 |
| 20mM bMEA | 100.0 | 97.6 | 95.8 | 93.3 | 92.3 | 91.0 |
| 50mM bMEA | 100.0 | 98.0 | 93.8 | 85.4 | 84.7 | 81.9 |

Column 31,
Lines 23-31,

"Table 6    Net Recovery - Conversion at 50?+0C and stated bMEA concentration
Time (hours)
0             1.5        5           21       28                47
1mM bMEA    27.6    27.7       28.0    29.9            29.9    30.6
5mM bMEA    27.6    29.6       33.1    39.1            40.7    42.9
10mM bMEA   27.6    32.1       38.6    47.4            48.6    51.6
20m1V1 bMEA 27.6    34.5       42.2    55.1            57.0    60.2
50mM bMEA   27.6    40.2       49.6    63.8            65.0    65.0
"

should read

Table 6    Net Recovery - Conversion at 50°C and stated bMEA concentration

|  | Time (hours) | | | | | |
| --- | --- | --- | --- | --- | --- | --- |
|  | 0 | 1.5 | 5 | 21 | 28 | 47 |
| 1mM bMEA | 27.6 | 27.7 | 28.0 | 29.9 | 29.9 | 30.6 |
| 5mM bMEA | 27.6 | 29.6 | 33.1 | 39.1 | 40.7 | 42.9 |
| 10mM bMEA | 27.6 | 32.1 | 38.6 | 47.4 | 48.6 | 51.6 |
| 20mM bMEA | 27.6 | 34.5 | 42.2 | 55.1 | 57.0 | 60.2 |
| 50mM bMEA | 27.6 | 40.2 | 49.6 | 63.8 | 65.0 | 65.0 |

Column 35,
Lines 16-18,

"Glycin   Serin  Prolin  Alanin  Lysin  Argini  Polysorba  Polysorba  AmmS   NaCi
e mM     e      e mM    e mM    e      ne mM   te 80      (2%        te 20 2%  ul   (4   t (1.5
"mM      mM     v/v)    v/v)    M)     M)
"

should read

| Glycine mM | Serine mM | Proline mM | Alanine mM | Lysine mM | Arginine mM | Polysorbate 80 (2% v/v) | Polysorbate 20 2% v/v) | AmmSul (4 M) | NaCit (1.5 M) |
| --- | --- | --- | --- | --- | --- | --- | --- | --- | --- |

Column 36,
Line 52, "Ni" should read --N1--.

Column 37,
Line 6, "Ni" should read --N1--.

Column 38,
Lines 55-66,

"
Table 17: Experimental results for 2L conversion experiments

| CCF Load Pre Conversion | | | | CCF Post Conversion | | | | | |
|---|---|---|---|---|---|---|---|---|---|
| Titre (g/L) | Ab load (g) | % Monomer | Monomer load (g) | Titre (g/L) | Ab recovered (g) | Ab Yield (%) | % Monomer | Monomer recovered (g) | Monomer yield (%) |
| 2.04 | 4.4 | 30.2 | 1.33 | 1.73 | 3.73 | 84.8 | 50.9 | 1.90 | 142.9 |

"

should read

Table 17: Experimental results for 2L conversion experiments

| CCF Load Pre Conversion | | | | CCF Post Conversion | | | | | |
|---|---|---|---|---|---|---|---|---|---|
| Titre (g/L) | Ab load (g) | % Monomer | Monomer load (g) | Titre (g/L) | Ab Recovered (g) | Ab Yield (%) | % Monomer | Monomer recovered (g) | Monomer yield (%) |
| 2.04 | 4.40 | 30.2 | 1.33 | 1.73 | 3.73 | 84.8 | 50.9 | 1.90 | 142.9 |

--.